United States Patent
Watanabe et al.

(10) Patent No.: US 9,947,482 B2
(45) Date of Patent: Apr. 17, 2018

(54) PHOTOELECTRIC CONVERSION ELEMENT, DYE-SENSITIZED SOLAR CELL, AND METAL COMPLEX DYE USED IN SAME

(71) Applicant: FUJIFILM Corporation, Tokyo (JP)

(72) Inventors: Kohsuke Watanabe, Ashigarakami-gun (JP); Hirotaka Sato, Ashigarakami-gun (JP); Yukio Tani, Ashigarakami-gun (JP); Ryo Fujiwara, Ashigarakami-gun (JP); Kazuhiro Tsuna, Ashigarakami-gun (JP); Katsumi Kobayashi, Ashigarakami-gun (JP)

(73) Assignee: FUJIFILM Corporation, Tokoyo (JP)

( * ) Notice: Subject to any disclaimer, the term of this patent is extended or adjusted under 35 U.S.C. 154(b) by 187 days.

(21) Appl. No.: 14/879,822

(22) Filed: Oct. 9, 2015

(65) Prior Publication Data

US 2016/0042875 A1 Feb. 11, 2016

Related U.S. Application Data

(63) Continuation of application No. PCT/JP2014/060108, filed on Apr. 7, 2014.

(30) Foreign Application Priority Data

| Apr. 12, 2013 | (JP) | 2013-084416 |
| Dec. 27, 2013 | (JP) | 2013-273192 |
| Dec. 27, 2013 | (JP) | 2013-273193 |

(51) Int. Cl.
*H01G 9/20* (2006.01)
*C07F 15/00* (2006.01)
(Continued)

(52) U.S. Cl.
CPC ....... *H01G 9/2059* (2013.01); *C07F 15/0053* (2013.01); *C09B 57/008* (2013.01);
(Continued)

(58) Field of Classification Search
None
See application file for complete search history.

(56) References Cited

U.S. PATENT DOCUMENTS

| 5,463,057 A | 10/1995 | Graetzel et al. |
| 6,291,763 B1 * | 9/2001 | Nakamura ........... H01G 9/2009 136/252 |

(Continued)

FOREIGN PATENT DOCUMENTS

| JP | 2000-311723 A | 11/2000 |
| JP | 2001-236999 A | 8/2001 |

(Continued)

OTHER PUBLICATIONS

International Preliminary Report on Patentability and English translation of the Written Opinion of the International Searching Authority (forms PCT/IB/373 and PCT/ISA/237), dated Oct. 13, 2015, for International Application No. PCT/JP2014/060108.

(Continued)

*Primary Examiner* — Katie L Hammer
(74) *Attorney, Agent, or Firm* — Birch, Stewart, Kolasch & Birch, LLP

(57) ABSTRACT

A photoelectric conversion element has a conductive support, a photoreceptor layer containing an electrolyte, a charge carrier layer containing an electrolyte and a counter electrode, and the photoreceptor layer has semiconductor particles on which a metal complex dye represented by Formula (I) is carried.

$$M^1(LA)(LD)(Z^1).CI \qquad \text{Formula (I)}$$

(Continued)

$M^1$ represents a metal atom; $Z^1$ represents a monodentate ligand; LA represents a tridentate ligand represented by Formula (AL-1); LD represents a bidentate ligand represented by Formula (DL-1); and CI represents a counterion necessary for neutralizing the charge.

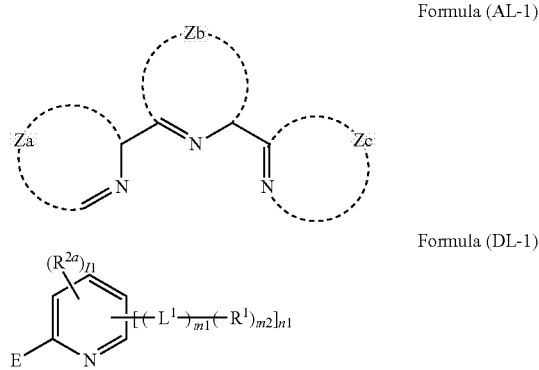

Formula (AL-1)

Formula (DL-1)

35 Claims, 4 Drawing Sheets

(51) Int. Cl.
    *C09B 57/10*     (2006.01)
    *H01L 51/00*     (2006.01)
    *C09B 57/00*     (2006.01)
(52) U.S. Cl.
    CPC .......... *C09B 57/10* (2013.01); *H01L 51/0086* (2013.01); *H01G 9/2031* (2013.01); *Y02E 10/542* (2013.01); *Y02E 10/549* (2013.01)

(56) References Cited

U.S. PATENT DOCUMENTS

| | | | | |
|---|---|---|---|---|
| 2002/0015881 A1* | 2/2002 | Nakamura | ........... | H01G 9/2009 429/111 |
| 2006/0188798 A1* | 8/2006 | Tokutake | ............... | G03G 5/144 430/60 |
| 2009/0114283 A1* | 5/2009 | Lee | ....................... | H01G 9/2013 136/260 |
| 2010/0258175 A1 | 10/2010 | Chi et al. | | |
| 2012/0073660 A1* | 3/2012 | Chi | .................... | C07F 15/0046 136/263 |
| 2014/0209172 A1 | 7/2014 | Tani et al. | | |

FOREIGN PATENT DOCUMENTS

| | | |
|---|---|---|
| JP | 2002-280587 A | 9/2002 |
| JP | 2003-100357 A | 4/2003 |
| JP | 2012-119195 A | 6/2012 |
| WO | WO 2013/047238 A1 | 4/2013 |
| WO | WO 2013/047615 A1 | 4/2013 |

OTHER PUBLICATIONS

Japanese Notification of Reasons for Refusal for Japanese Application No. 2013-273192, dated Oct. 4, 2016, with machine translation.
Taiwanese Office Action and Search Report, dated Feb. 16, 2017, for corresponding Taiwanese Application No. 103113201, with an English translation of the Office Action.
International Search Report, issued in PCT/JP2014/060108, dated, Jul. 8, 2014.
Written Opinion of the International Searching Authority, issued in PCT/JP2014/060108, dated, Jul. 8, 2014.
Chinese Office Action and Search Report, dated Mar. 31, 2017, for corresponding Chinese Application No. 201480020029.4, with an English translation of the Chinese Office Action.

* cited by examiner

PHOTOELECTRIC CONVERSION ELEMENT, DYE-SENSITIZED SOLAR CELL, AND METAL COMPLEX DYE USED IN SAME

CROSS-REFERENCE TO RELATED APPLICATIONS

This application is a Continuation of PCT International Application No. PCT/JP2014/60108, filed on Apr. 7, 2014, which claims priority under 35 U.S.C. § 119(a) to Japanese Patent Application No. 2013-084416, filed on Apr. 12, 2013, Japanese Patent Application No. 2013-273192, filed on Dec. 27, 2013 and Japanese Patent Application No. 2013-273193, filed on Dec. 27, 2013. Each of the above application(s) is hereby expressly incorporated by reference, in its entirety, into the present application.

BACKGROUND OF THE INVENTION

1. Field of the Invention

The present invention relates to a photoelectric conversion element, a dye-sensitized solar cell, and a metal complex dye used in the same.

2. Description of the Related Art

Photoelectric conversion elements are used in various photosensors, copy machines, solar cells, and the like. The photoelectric conversion elements have been put to practical use in the form of photoelectric conversion elements adopting various modes, such as photoelectric conversion elements using metals, photoelectric conversion elements using semiconductors, photoelectric conversion elements using organic pigments or dyes, or photoelectric conversion elements as a combination of these. Particularly, because solar cells using inexhaustible solar energy do not require fuel and use inexhaustible clean energy, full-scale commercialization of solar cells is highly anticipated. Among solar cells, silicon-based solar cells have been researched and developed for a long period of time, and are becoming increasingly popular by the political support of each country. However, because silicon is an inorganic material, the throughput and molecular modification thereof are inevitably limited.

For this reason, dye-sensitized solar cells are being strenuously researched. Particularly, the research was fueled by the results of research conducted by Graetzel et al. of EPFL of Switzerland. By adopting a structure in which a dye composed of a ruthenium complex is fixed to the surface of a thin film of porous titanium oxide, Graetzel et al. realized photoelectric conversion efficiency equivalent to that of amorphous silicon. As a result, dye-sensitized solar cells instantly drew the attention of researchers all over the world.

U.S. Pat. No. 5,463,057A describes a dye sensitized photoelectric conversion element using semiconductor particles sensitized by a ruthenium complex dye by applying the aforementioned technique. Since then, in order to improve the photoelectric conversion efficiency, ruthenium complex-based sensitizing dyes have been continuously developed (see US2010/0258175A).

SUMMARY OF THE INVENTION

Numerous research and development using N749 as a terpyridyl-based metal complex dye are being conducted, and US2010/0258175A relates to a dye that is obtained by improving the aforementioned dye. These metal complex dyes have insufficient durability, and further improvement of the photoelectric conversion efficiency thereof is also required.

However, under the current circumstances, it is difficult to accomplish both durability and photoelectric conversion efficiency simultaneously.

The present invention has been made in consideration of the current circumstances, and an object thereof is to provide a photoelectric conversion element, a dye-sensitized solar cell, and a metal complex dye used in the same, all of which are excellent in both durability and photoelectric conversion efficiency.

The above object was achieved by the following means.

<1> A photoelectric conversion element including a conductive support, a photoreceptor layer containing an electrolyte, and a charge carrier layer containing an electrolyte, and a counter electrode, in which the photoreceptor layer has semiconductor particles on which a metal complex dye represented by the following Formula (I) is carried.

$$M^1(LA)(LD)(Z^1) \cdot CI \quad \text{Formula (I)}$$

In Formula (I), $M^1$ represents a metal atom, and $Z^1$ represents a monodentate ligand. LA represents a tridentate ligand represented by the following Formula (AL-1). LD represents a bidentate ligand represented by the following Formula (DL-1). CI represents a counterion necessary for neutralizing the charge.

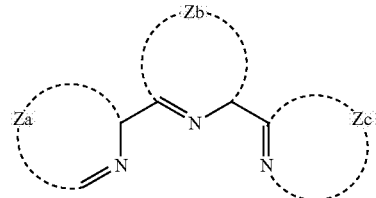

Formula (AL-1)

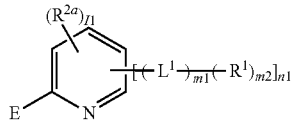

Formula (DL-1)

In Formula (AL-1), each of Za, Zb, and Zc represents a group of non-metal atoms necessary for forming a 5-membered ring or a 6-membered ring. Here, at least one of the rings formed by Za, Zb, and Zc has an acidic group.

in Formula (DL-1), m1 represents an integer of 0 to 3, m2 represents an integer of 1 to 4, and n1 represents an integer of 1 to 4. $L^1$ represents an arylene group, an alkynylene group, or an alkynylenearylene group, and $R^1$ represents an amino group, an alkylamino group, an arylamino group, a heteroarylamino group, a halogen atom, an alkyl group, an alkynyl group, an alkoxy group, an aryloxy group, an alkylthio group, or an arylthio group. l1 represents an integer of 0 to 3, and $R^{2a}$ represents a substituent different from -[($L^1$)m1-($R^1$)m2]. E represents a group represented by one of the following Formulae (E-1) to (E-6), (E-21), and (E-22).

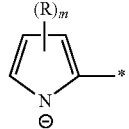

Formula (E-1)

Formula (E-2)

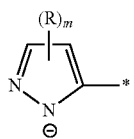

Formula (E-3)

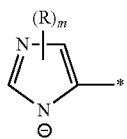

Formula (E-4)

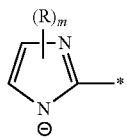

Formula (E-5)

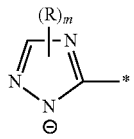

Formula (E-6)

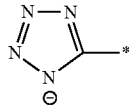

In Formulae (E-1) to (E-6), R represents a halogen atom, an alkyl group, an alkoxy group, an aryl group, or a heteroaryl group. m represents an integer of equal to or greater than 0. Herein, * represents a binding position in which the group is bonded to the 2-position of a pyridine ring, Formula (E-21)

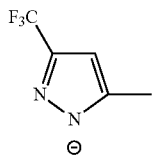

Formula (E-22)

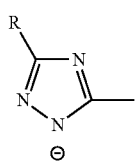

In Formula (E-22), R represents a hydrogen atom, an alkyl group, a phenyl group, or an aryloxy group.

<2> The photoelectric conversion element described in <1>, in which the bidentate ligand represented by Formula (DL-1) is represented by the following Formula (DL-2).

Formula (DL-2)

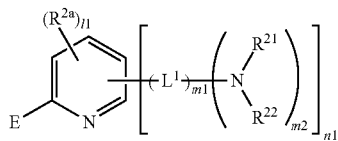

In Formula (DL-2), E, $L^1$, m1, m2, n1, $R^{2a}$, and 11 have the same definition as that of E, $L^1$, m1, m2, n1, $R^{2a}$, and 11 in Formula (DL-1). Each of $R^{21}$ and $R^{22}$ independently represents a hydrogen atom, an alkyl group, an aryl group, or a heteroaryl group. $R^{21}$ and $R^{22}$ may form a ring by being bonded to each other.

<3> The photoelectric conversion element described in <1> or <2>, in which $L^1$ represents an arylene group.

<4> The photoelectric conversion element described in <1> or <2>, in which the bidentate ligand represented by Formula (DL-1) is represented by the following Formula (DL-3).

Formula (DL-3)

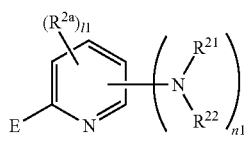

In Formula (DL-3), E, $R^{21}$, $R^{22}$, n1, $R^{2a}$ and 11 have the same definition as that of E, $R^{21}$, $R^{22}$, n1, $R^{2a}$, and 11 in Formula (DL-2).

<5> The photoelectric conversion element described in any one of <1> to <4>, in which $M^1$ represents Ru.

<6> The photoelectric conversion element described in any one of <1> to <5>, in which LA is represented by the following Formula (AL-3).

Formula (AL-3)

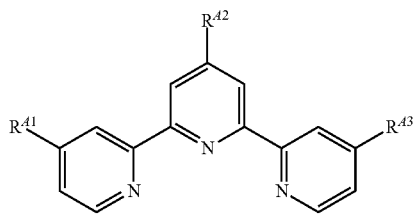

In Formula (AL-3), each of $R^{41}$, $R^{42}$, and R represents a hydrogen atom, an alkyl group, an aryl group, a heteroaryl group, or an acidic group. Here, at least one of $R^{41}$, $R^{42}$, and $R^{43}$ represents an acidic group.

<7> The photoelectric conversion element described in any one of <1> to <6>, in which E is represented by Formula (E-2) or Formula (E-5).

<8> The photoelectric conversion element described in any one of <1> to <7>, in which the metal complex dye is represented by the following Formula (II).

Formula (II)

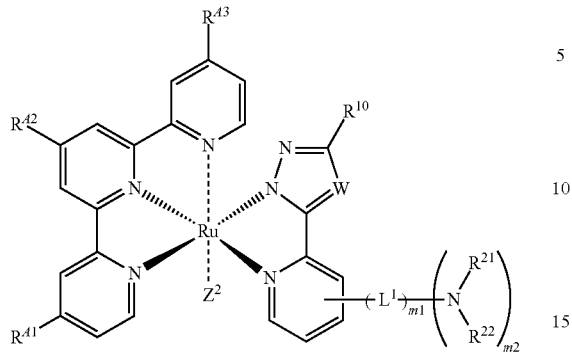

In Formula (II), $R^{41}$ to $R^{43}$ the same definition as that of $R^{41}$ to $R^{43}$ in Formula (AL-3). $R^{21}$, $R^{22}$, $L^1$, m1, and m2 have the same definition as that of $R^{21}$, $R^{22}$, $L^1$, m1, and m2 in Formula (DL-2). W represents a nitrogen atom or CH. $R^{10}$ represents a hydrogen atom, an alkyl group, a perfluoroalkyl group, an aryl group, or a heteroaryl group. $Z^2$ represents an isothiocyanate group, an isoselenocyanate group, an isocyanate group, a halogen atom, or a cyano group.

<9> The photoelectric conversion element described in any one of <1> to <8>, in which the metal complex dye is represented by the following Formula (III).

Formula (III)

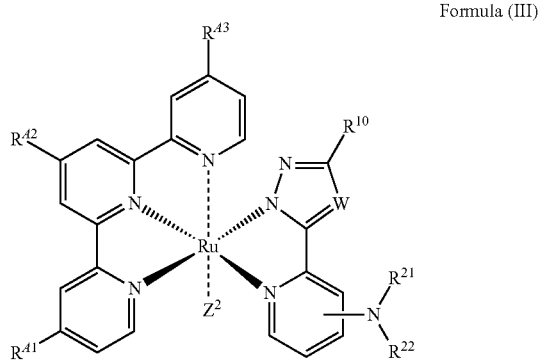

In Formula (III), $R^{41}$ to $R^{43}$ have the same definition as that of $R^{41}$ to $R^{43}$ in Formula (AL-3). W, $R^{21}$, $R^{22}$, $R^{10}$, and $Z^2$ have the same definition as that of W, $R^{21}$, $R^{22}$, $R^{10}$, and $Z^2$ in Formula (II).

<10> The photoelectric conversion element described in any one of <2> to <9>, in which each of $R^{21}$ and $R^{22}$ is selected from an alkyl group and an aryl group.

<11> The photoelectric conversion element described in any one of <2> to <10>, in which $R^{21}$ represents an alkyl group or an aryl group, and $R^{22}$ represents an aryl group.

<12> The photoelectric conversion element described in <1>, in which Formula (DL-1) satisfies the following conditions. In Formula (DL-1), l1 represents 0. $L^1$ represents an arylene group, and $R^1$ represents a halogen atom, an alkyl group, an alkynyl group, an alkoxy group, an aryloxy group, an alkylthio group, or an arylthio group. E represents a group represented by Formula (E-21) or (E-22).

<13> The photoelectric conversion element described in <12>, in which LD is represented by any of the following Formulae (DL-22) to (DL-24).

Formula (DL-22)

Formula (DL-23)

Formula (DL-24)

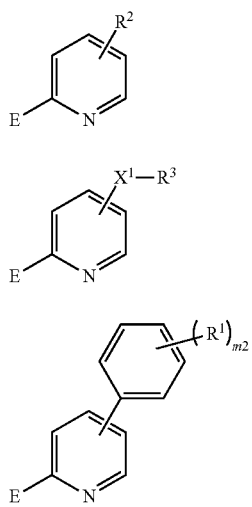

In Formulae (DL-22) to (DL-24), E, $R^1$, and m2 have the same definition as that of E, $R^1$, and m2 in Formula (DL-1). $X^1$ represents —C(Ra)(Rb)—, an ethynylene group, —S—, or —O—. Each of Ra and Rb independently represents a hydrogen atom or an alkyl group. $R^2$ represents a halogen atom. When $X^1$ represents —C(Ra)(Rb)—, $R^3$ represents a hydrogen atom or an alkyl group; when $X^1$ represents an ethynylene group, $R^3$ represents a hydrogen atom, an alkyl group, an aryl group, or a heteroaryl group; and when $X^1$ represents —S— or —O—, $R^3$ represents an alkyl group or an aryl group. When m2 is equal to or greater than 2, a plurality of $R^1$s may be the same as or different from each other.

<14> The photoelectric conversion element described in <12> or <13>, in which LD is represented by any of the following Formulae (DL-23a) to (DL-23d) or represented by any of the following Formulae (DL-24a) to (DL-24c).

Formula (DL-23a)

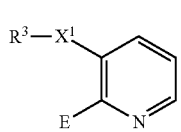

Formula (DL-23b)

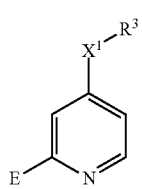

Formula (DL-23c)

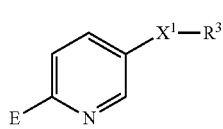

Formula (DL-23d)

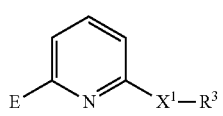

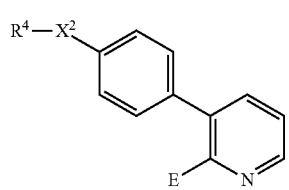

Formula (DL-24a)

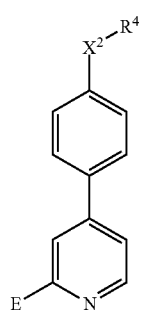

Formula (DL-24b)

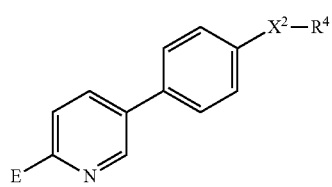

Formula (DL-24c)

In Formulae (DL-23a) to (DL-23d) and (DL-24a) to (DL-24c), E has the same definition as that of E in Formula (DL-1). $X^1$ and $R^3$ have the same definition as that of $X^1$ and $R^3$ in Formula (DL-3). $X^2$ represents —C(Ra)(Rb)—, an ethynylene group, —S—, or —O—. Each of Ra and Rb represents a hydrogen atom or an alkyl group. When $X^2$ represents —C(Ra)(Rb)—, $R^4$ represents a hydrogen atom or an alkyl group; when $X^2$ represents an ethynylene group, $R^4$ represents a hydrogen atom, an alkyl group, an aryl group, or a heteroaryl group; and when $X^2$ represents —S— or —O—, $R^4$ represents an alkyl group or an aryl group.

<15> The photoelectric conversion element described in <13>, in which $X^1$ or $X^2$ represents —C(Ra)(Rb)—, an ethynylene group, or —O—.

<16> The photoelectric conversion element described in <14>, in which $X^1$ or $X^2$ represents —C(Ra)(Rb)—, an ethynylene group, or —O—.

<17> The photoelectric conversion element described in any one of <13> to <16>, in which $R^3$ represents an alkyl group having 5 or more carbon atoms.

<18> The photoelectric conversion element described in any one of <14> to <16>, in which $R^3$ or $R^4$ represents an alkyl group having 5 or more carbon atoms.

<19> The photoelectric conversion element described in any one of <13> to <18>, in which $R^3$ represents a linear alkyl group having 5 or more carbon atoms.

<20> The photoelectric conversion element described in any one of <14> to <18>, in which $R^3$ or $R^4$ represents a linear alkyl group having 5 or more carbon atoms.

<21> The photoelectric conversion element described in any one of <12> to <20>, in which the metal complex dye is represented by the following Formula (XXII).

Formula (XXII)

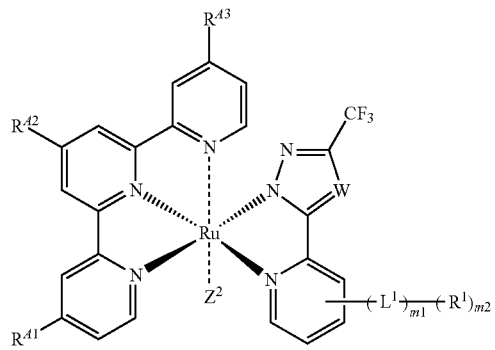

In Formula (XXII), $R^{A1}$ to $R^{A3}$ have the same definition as that of $R^{A1}$ to $R^{A3}$ in Formula (AL-3). $R^1$, $L^1$, m1, and m2 have the same definition as that of $R^1$, $L^1$, m1, and m2 in Formula (DL-1). W represents CH. $Z^2$ represents an isothiocyanate group, an isoselenocyanate group, an isocyanate group, a halogen atom, or a cyano group.

<22> The photoelectric conversion element described in any one of <12> to <21>, in which the metal complex dye is represented by the following Formula (XXIII)

Formula (XXIII)

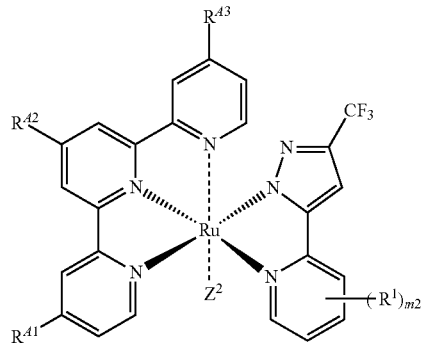

In Formula (XXIII), $R^{A1}$ to $R^{A3}$ have the same definition as that of $R^{A1}$ to $R^{A3}$ in Formula (AL-3). $R^1$ and m2 have the same definition as that of $R^1$ and m2 in Formula (DL-1). $Z^2$ has the same definition as that of $Z^2$ in Formula (XXII).

<23> The photoelectric conversion element described in any one of <1> to <22>, in which a coadsorbent having 1 or more acidic groups is further carried on the semiconductor particles.

<24> The photoelectric conversion element described in <23>, in which the coadsorbent is represented by the following Formula (CA).

Formula (CA)

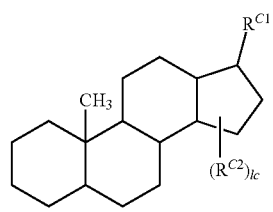

In Formula (CA), $R^{C1}$ represents a substituent having an acidic group. $R^{C2}$ represents a substituent. lc represents an integer of equal to or greater than 0.

<25> A dye-sensitized solar cell including the photoelectric conversion element described in any one of <1> to <24>.

<26> A metal complex dye represented by the following Formula (I).

$$M^1(LA)(LD)(Z^1)\cdot CI \qquad \text{Formula (I)}$$

In Formula (I), $M^1$ represents a metal atom, and $Z^1$ represents a monodentate ligand. LA represents a tridentate ligand represented by the following Formula (AL-1). LD represents a bidentate ligand represented by the following Formula (DL-1). CI represents a counterion necessary for neutralizing the charge.

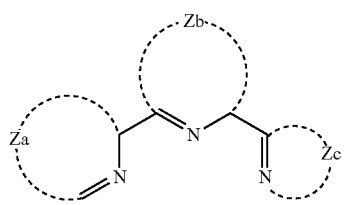

Formula (AL-1)

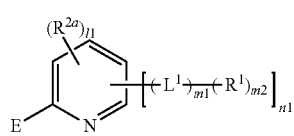

Formula (DL-1)

In Formula (AL-1), each of Za, Zb, and Zc represents a group of non-metal atoms necessary for forming a 5-membered ring or a 6-membered ring. Here, at least one of the rings formed by Za, Zb, and Zc has an acidic group.

In Formula (DL-1), m1 represents an integer of 0 to 3, m2 represents an integer of 1 to 4, and n1 represents an integer of 1 to 4. $L^1$ represents an arylene group, an alkynylene group, or an alkynylenearylene group, and $R^1$ represents an amino group, an alkylamino group, an arylamino group, a heteroarylamino group, a halogen atom, an alkyl group, an alkynyl group, an alkoxy group, an aryloxy group, an alkylthio group, or an arylthio group. l1 represents an integer of 0 to 3, and $R^{2a}$ represents a substituent different from -[($L^1$)m1-($R^1$)m2]. E represents a group represented by one of the following Formulae (E-1) to (E-6), (E-21), and (E-22).

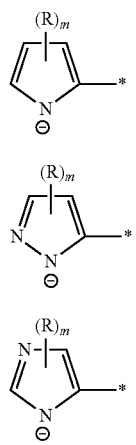

Formula (E-1)

Formula (E-2)

Formula (E-3)

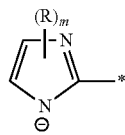

Formula (E-4)

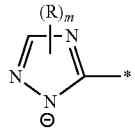

Formula (E-5)

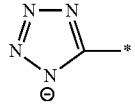

Formula (E-6)

In Formulae (E-1) to (E-6), R represents a halogen atom, an alkyl group, an alkoxy group, an aryl group, or a heteroaryl group. m represents an integer of equal to or greater than 0. Herein, * represents a binding position in which the group is bonded to the 2-position of a pyridine ring.

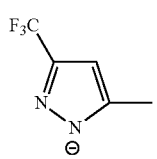

Formula (E-21)

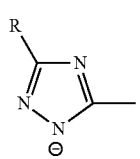

Formula (E-22)

In Formula (E-22), R represents a hydrogen atom, an alkyl group, a phenyl group, or an aryloxy group.

<27> The metal complex dye described in <26> that is represented by the following Formula (II).

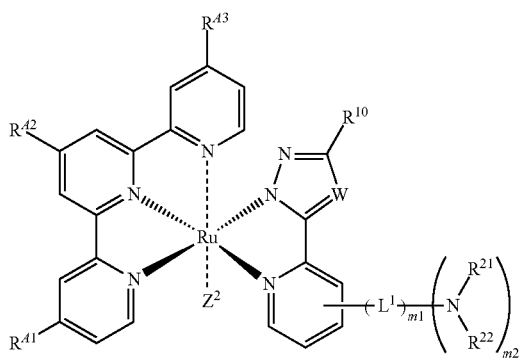

Formula (II)

In Formula (II), $R^{41}$ to $R^{43}$ have the same definition as that of $R^{41}$ to $R^{43}$ in Formula (AL-3). $R^{21}$, $R^{22}$, $L^1$, m1, and m2 have the same definition as that of $R^{21}$, $R^{22}$, $L^1$, m1, and m2 in Formula (DL-2). W represents a nitrogen atom or CH.

$R^{10}$ represents a hydrogen atom, an alkyl group, a perfluoroalkyl group, an aryl group, or a heteroaryl group. $Z^2$ represents an isothiocyanate group, an isoselenocyanate group, an isocyanate group, a halogen atom, or a cyano group.

<28> The metal complex dye described in <26> or <27> that is represented by the following Formula (III).

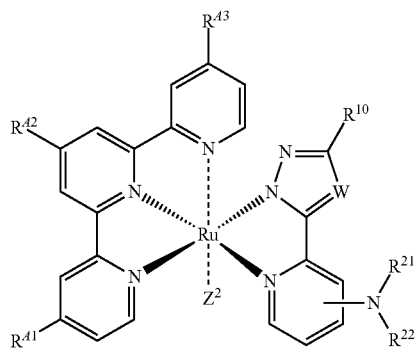

Formula (III)

In Formula (III), $R^{41}$ to $R^{43}$ have the same definition as that of $R^{41}$ to $R^{43}$ in Formula (AL-3). W, $R^{21}$, $R^{22}$, $R^{10}$ and $Z^2$ have the same definition as that of W, $R^{21}$, $R^{22}$, $R^{10}$ and $Z^2$ in Formula (II).

<29> The metal complex dye described in <26>, in which Formula (DL-1) satisfies the following conditions. In Formula (DL-1), l1 represents 0. $L^1$ represents an arylene group, and $R^1$ represents a halogen atom, an alkyl group, an alkynyl group, an alkoxy group, an aryloxy group, an alkylthio group, or an arylthio group. E represents a group represented by the following Formula (E-21) or (E-22).

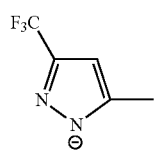

Formula (E-21)

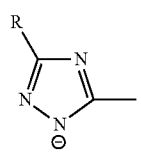

Formula (E-22)

In Formula (E-22), R represents a hydrogen atom, an alkyl group, a phenyl group, or an aryloxy group.

In the present specification, unless otherwise specified, regarding a carbon-carbon double bond, when an E-isomer and a Z-isomer are present in a molecule, the double bond may be either the E-isomer or the Z-isomer or may be a mixture of these. Furthermore, when there are a plurality of substituents, linking groups, ligands, and the like (hereinafter, referred to as "substituents and the like) marked with a specific sign, or when the plurality of substituents and the like are specified collectively or selectively, unless otherwise specified, the substituents and the like may be the same as or different from each other. The same will be applied to the case in which the number of the substituents and the like is specified. In addition, when the plurality of substituents are close to each other (particularly, when they are adjacent to each other), unless otherwise specified, the substituents may form a ring by being linked to each other. Moreover, rings, for example, an alicyclic ring, an aromatic ring, or a heterocyclic ring may form a fused ring by being further fused.

In the present invention, unless otherwise specified, each of the substituents may be further substituted with a substituent.

According to the present invention, it is possible to provide a photoelectric conversion element, a dye-sensitized solar cell, and a metal complex dye used in the same, all of which are excellent in both durability and photoelectric conversion efficiency.

DESCRIPTION OF THE PREFERRED EMBODIMENTS

<<Photoelectric Conversion Element and Dye-sensitized Solar Cell>>

Figure 1:
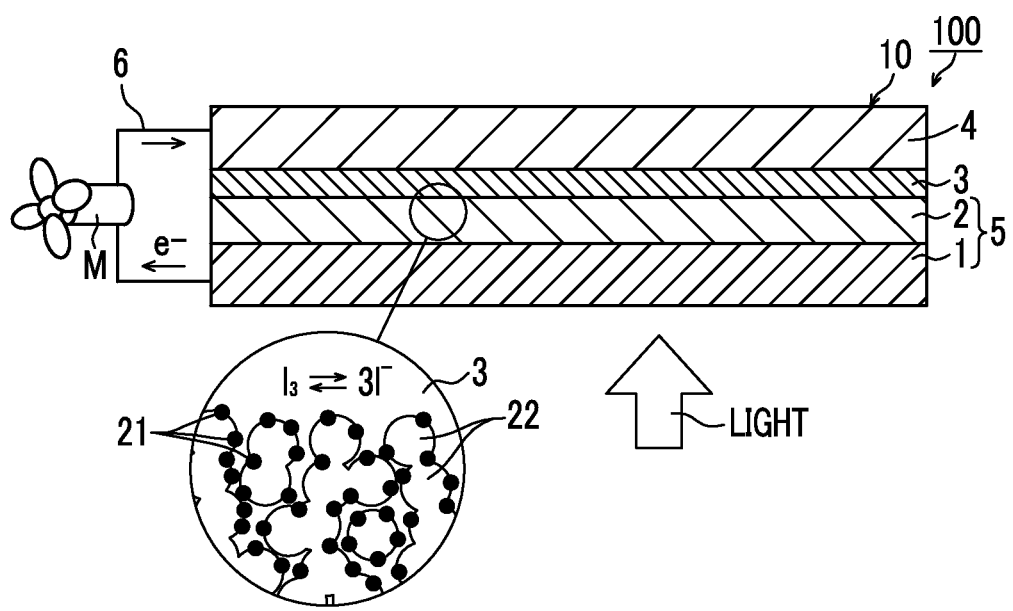
FIG. 1 is a cross-sectional view schematically showing an embodiment of a photoelectric conversion element of the present invention, including an enlarged view of a portion marked with a circle in a layer.

As shown in FIG. 1, a photoelectric conversion element 10 of an embodiment of the present invention has a conductive support 1, a photoreceptor layer 2 which contains semiconductor particles 22 sensitized by a dye (metal complex dye) 21, a charge carrier layer 3 which is a hole transport layer, and a counter electrode 4. The conductive support 1 on which the photoreceptor layer 2 is installed functions as a working electrode in the photoelectric conversion element 10. In the present embodiment, the photoelectric conversion element 10 is included in a system 100 using a dye-sensitized solar cell. In the system 100 using a dye-sensitized solar cell, the photoelectric conversion element 10 can be used as a battery for operating an electric motor (electric fan) M as operating means through an external circuit 6.

In the present embodiment, a light-receiving electrode 5 is composed of the conductive support 1 and the photoreceptor layer 2 which contains semiconductor particles 22 onto which the dye (metal complex dye) 21 is adsorbed. The photoreceptor layer 2 is designed according to the purpose, and may be constituted with a single layer or multiple layers. A single photoreceptor layer may contain one kind of the dye (metal complex dye) 21 or a mixture of plural kinds of the dye 21. However, as at least one kind among the dyes, the metal complex dye of the present invention that will be described later is used. The light that enters the photoreceptor layer 2 excites the dye (metal complex dye) 21. The excited dye has electrons with high energy. The electrons are transferred to the conduction band of the semiconductor particles 22 from the dye (metal complex dye) 21 and then reach the conductive support 1 by diffusion. At this time, the dye (metal complex dye) 21 becomes an oxidized dye.

While working in the external circuit 6, the electrons on the electrode pass through the counter electrode 4 and return to the photoreceptor layer 2 where the oxidized dye (metal complex dye) 21 and an electrolyte are present. In this way, the photoelectric conversion element functions as a solar cell.

In the present invention, regarding the materials used in the photoelectric conversion element or in the dye-sensitized solar cell and the preparation methods of respective members, the preparation methods that are generally used in such photoelectric conversion element and dye-sensitized solar cell may be adopted. Regarding the preparation methods, for example, U.S. Pat. Nos. 4,927,721, 4,684,537, 5,084,365, 5,350,644, 5,463,057, 5,525,440, JP1995-249790A (JP-H07-249790A), JP2004-220974A, and JP2008-135197A can be referred to.

Hereinafter, main members will be schematically described.

<Photoreceptor Layer>

The photoreceptor layer is a layer that contains an electrolyte, which will be described later, and semiconductor particles on which a sensitizing dye containing the following metal complex dye of the present invention is supported.

<<Metal Complex Dye>>

[Metal Complex Dye of First Embodiment]

A metal complex dye of a first embodiment is represented by the following Formula (I).

    Formula (I)

In Formula (I), $M^1$ represents a metal atom, and $Z^1$ represents a monodentate ligand. LA represents a tridentate ligand represented by the following Formula (AL-1). LD represents a bidentate ligand represented by the following Formula (DL-1). CI represents a counterion necessary for neutralizing the charge.

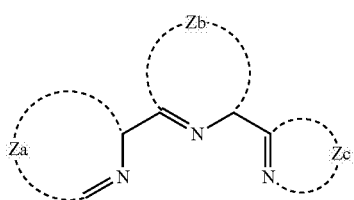    Formula (AL-1)

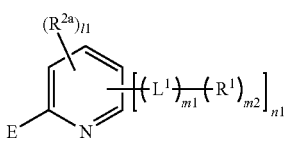    Formula (DL-1)

In Formula (AL-1), each of Za, Zb, and Zc represents a group of non-metal atoms necessary for forming a 5-membered ring or a 6-membered ring. Here, at least one of the rings formed by Za, Zb, and Zc has an acidic group.

In Formula (DL-1), m1 represents an integer of 0 to 3, m2 represents an integer of 1 to 4, and n1 represents an integer of 1 to 4. $L^1$ represents an arylene group, an alkynylene group, or an alkynylenearylene group, and $R^1$ represents an amino group, an alkylamino group, an arylamino group, or a heteroarylamino group. l1 represents an integer of 0 to 3, and $R^{2a}$ represents a substituent different from $-[(L^1)m1-(R^1)m2]$. E represents a group represented by any of the following Formulae (E-1) to (E-6).

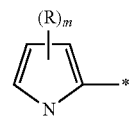    Formula (E-1)

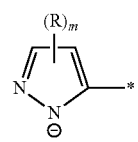    Formula (E-2)

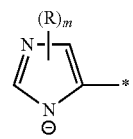    Formula (E-3)

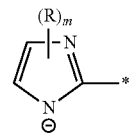    Formula (E-4)

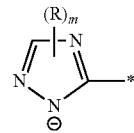    Formula (E-5)

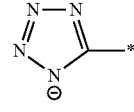    Formula (E-6)

In Formulae (E-1) to (E-5), R represents a halogen atom, an alkyl group, an alkoxy group, an aryl group, or a heteroaryl group. m represents an integer of equal to or greater than 0. Herein, * represents a binding position in which the group is bonded to the 2-position of a pyridine ring.

—Metal Atom $M^1$—

$M^1$ represents a metal atom. $M^1$ is preferably a metal that can form a coordinate bond at 4 sites or 6 sites, and examples thereof include the elements of group 6 to group 12 in the long-form periodic table. $M^1$ is more preferably Ru, Os, Zn, Cu, Rh, Re, Mn, or Zn, particularly preferably Ru, Os, Zn, or Cu, and most preferably Ru.

—Ligand LA—

In the first embodiment, the ligand LA is represented by Formula (AL-1).

Each of Za, Zb, and Zc represents a group of non-metal atoms necessary for forming a 5-membered ring or a 6-membered ring.

The 5-membered ring or 6-membered ring formed by Za, Zb, and Zc may be substituted or unsubstituted or may be a monocyclic ring or a fused ring. The ring-constituting atom of Za, Zb, and Zc is preferably an atom selected from a carbon atom, a nitrogen atom, an oxygen atom, a sulfur atom, and a phosphorus atom. The ring-constituting atom may be substituted with a substituent including a hydrogen atom or a halogen atom.

The ring formed by Za, Zb, and Zc is more preferably an aromatic ring, that is, a nitrogen-containing aromatic ring.

When forming a 5-membered ring, Za, Zb, and Zc preferably form an imidazole ring, an oxazole ring, a thiazole ring, or a triazole ring. When forming a 6-membered ring, Za, Zb, and Zc preferably form a pyridine ring, a pyrimidine ring, a pyridazine ring, or a pyrazine ring. Among these, an imidazole ring or a pyridine ring is more preferable.

In the metal complex dye of the first embodiment, at least one of the rings formed by Za, Zb, and Zc has an acidic group.

Acidic Group Ac

In the present invention, an acidic group is a substituent having a dissociative proton. Examples of the acidic group include a carboxy group, a phosphonyl group, a phosphoryl group, a sulfo group, a boric acid group, and the like, and among these, a carboxy group is preferable. The acidic group may be in a dissociated state by releasing a proton or may be a salt. Examples of the counterion which is necessary when the acidic group becomes a salt is not particularly limited but include the examples of positive ions in the following counterion CI. Herein, the acidic group exemplified above and groups in a preferred range thereof are referred to as an acidic group Ac in some cases.

Examples of the counterion CI include an alkali metal ion and an onium ion. Examples of the alkali metal ion include a K ion, a Na ion, a Li ion, and a cesium ion. Among these, a K ion, a Na ion, and cesium ion are preferable, and a K ion is more preferable.

Examples of the onium ion include an ammonium ion and a pyridinium ion. Examples of the ammonium ion include a tetraalkyl ammonium ion, a benzyltrialkyl ammonium ion, and a quaternary ammonium ion in which an aryl group and an alkyl group are mixed with each other. Among these, a tetraalkyl ammonium ion is preferable. In the tetraalkyl ammonium ion, the alkyl group preferably has 1 to 12 carbon atoms, more preferably has 1 to 8 carbon atoms, and even more preferably has 2 to 6 carbon atoms. Particularly, a tetrabutyl ammonium ion is preferable.

The ligand LA is preferably a ligand represented by the following Formula (AL-2).

Formula (AL-2)

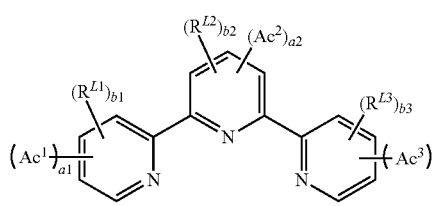

In Formula (AL-2), each of $Ac^1$, $Ac^2$, and $Ac^3$ independently represents an acidic group.

As the acidic group, the groups exemplified as the acidic group Ac are preferable.

Each of $R^{L1}$, $R^{L2}$, and $R^{L3}$ independently represents a substituent. Examples of the substituent include substituents T which will be described later. Each of $R^{L1}$, $R^{L2}$, and $R^{L3}$ is preferably an alkyl group, an alkenyl group, an alkynyl group, an aryl group, a heteroaryl group, an alkoxy group, an amino group, an alkylamino group, or an arylamino group, more preferably an alkyl group, an aryl group, or a heteroaryl group, and particularly preferably a heteroaryl group.

Each of a1, a3, b1, and b3 independently represents an integer of 0 to 4, and each of a2 and b2 independently represents an integer of 0 to 3. Here, a1 to a3 do not represent 0 at the same time.

The ligand LA is preferably a ligand represented by the following Formula (AL-3).

Formula (AL-3)

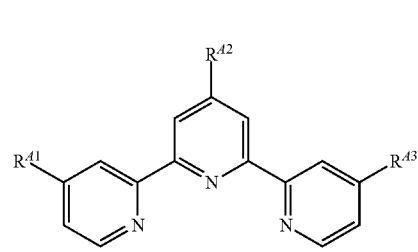

In Formula (AL-3), each of $R^{A1}$, $R^{A2}$, and $R^{A3}$ indepentaly represents a hydrogen atom, an alkyl group, an aryl group, a heteroaryl group, an acidic group, or a group containing an acidic group. Here, at least one of $R^{A1}$, $R^{A2}$, and $R^{A3}$ is an acidic group or a group containing an acidic group. The acidic group is preferably the acidic group Ac.

In the first embodiment, at least two out of $R^{A1}$, $R^{A2}$, and $R^{A3}$ preferably represent an acidic group, and all three of $R^{A1}$, $R^{A2}$, and $R^{A3}$ more preferably represent an acidic group. Particularly, all of $R^{A1}$, $R^{A2}$, and $R^{A3}$ preferably represent a carboxy group or a salt thereof.

Specific examples of the ligand LA in the first embodiment will be shown below, but the present invention is not limited thereto.

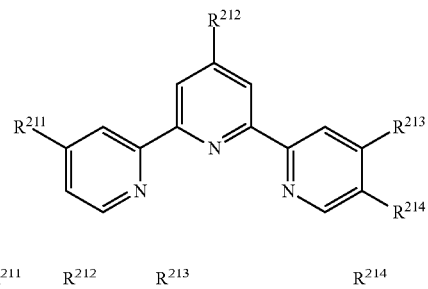

| | $R^{211}$ | $R^{212}$ | $R^{213}$ | $R^{214}$ |
|---|---|---|---|---|
| B-1-1 | —H | —$CO_2H$ | —H | —H |
| B-1-2 | —$CO_2H$ | —$CO_2H$ | —$CO_2H$ | —H |
| B-1-3 | —H | —$CO_2H$ | —H | —H |
| B-1-4 | —$CO_2H$ | —$CO_2H$ | —H | 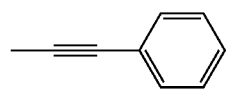 |
| B-1-5 | —$CO_2H$ | —$CO_2H$ | —H | 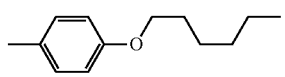 |
| B-1-6 | —H | —$PO_3H_2$ | —H | —H |
| B-1-7 | —H | —$CO_2H$ | —$CO_2H$ | —H |

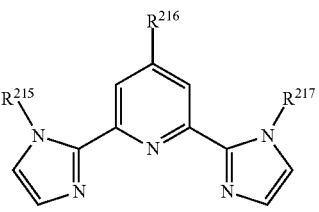

| | $R^{215}$ | $R^{216}$ | $R^{217}$ |
|---|---|---|---|
| B-2-1 | —H | —CO$_2$H | —H |
| B-2-2 | —$^nC_6H_{13}$ | —CO$_2$H | —H |
| B-2-3 | —$^nC_6H_{13}$ | —CO$_2$H | —$^nC_6H_{13}$ |
| B-2-4 | —H | —PO$_3$H$_2$ | —H |

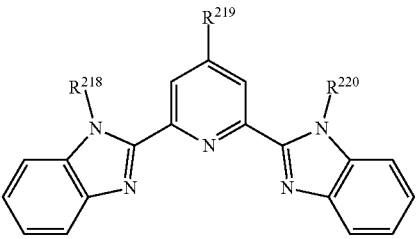

| | $R^{218}$ | $R^{219}$ | $R^{220}$ |
|---|---|---|---|
| B-3-1 | —H | —CO$_2$H | —H |
| B-3-2 | —$^nC_6H_{13}$ | —CO$_2$H | —H |
| B-3-3 | —$^nC_6H_{13}$ | —CO$_2$H | —$^nC_6H_{13}$ |
| B-3-4 | —H | —PO$_3$H$_2$ | —H |

—Ligand LD—

In the first embodiment, the ligand LD is represented by Formula (DL-1).

$L^1$ represents an arylene group, an alkynylene group, or an alkynylenearylene group, and among these, an arylene group is preferable.

Examples of the arylene group represented by $L^1$ include phenylene and naphthylene, and among these, phenylene is preferable. Examples of the phenylene include 1,4-phenylene, 1,3-phenylene, and 1,2-phenylene, and among these, 1,4-phenylene is preferable.

The arylene group may have a substituent. Examples of the substituent include the substituent T which will be described later. As the substituent, a halogen atom, an alkyl group, an aryl group, a heterocyclic group, an alkoxy group, an alkylthio group, an amino group, an alkylamino group, an arylamino group, and a heteroarylamino group are preferable. Among these, an amino group, an alkylamino group, an arylamino group, and a heteroarylamino group are more preferable.

The substituent and $R^1$ may form a ring by being bonded to each other. Furthermore, when the arylene group further has a plurality of substituents, the substituents may form a ring by being bonded to each other.

Each of the alkynylene group and the alkynylenearylene group represented by $L^1$ is preferably a group represented by the following Formula (LT).

$$*-C\equiv C-L^x-\qquad\text{Formula (LT)}$$

In Formula (LT), $L^x$ represents a single bond or an arylene group. * represents a position in which the group is bonded to a pyridine ring.

Examples of the arylene group represented by $L^x$ include the arylene group represented by $L^1$, and a preferred range thereof is also the same.

The arylene group represented by $L^x$ may have a substituent, and examples of the substituent include the substituents T which will be described later. Herein, the substituent for the arylene group is preferably the substituent exemplified in a case in which $L^1$ represents an arylene group.

In Formula (DL-1), $R^1$ represents an amino group, an alkylamino group, an arylamino group, or a heteroarylamino group.

Herein, the amino group is —NH$_2$. The alkylamino group includes an N-alkylamino group and an N,N-dialkylamino group. The arylamino group includes an N-arylamino group, an N-alkyl-N-arylamino group, and an N,N-diarylamino group. The heteroarylamino group includes an N-heteroarylamino group, an N-alkyl-N-heteroarylamino group, and an N-aryl-N-heteroarylamino group.

The alkyl group substituted with a nitrogen atom in each of the aforementioned amino groups preferably has 1 to 18 carbon atoms, and more preferably has 4 to 12 carbon atoms. Furthermore, the alkyl group may be linear or branched. Examples of the alkyl group include methyl, ethyl, isopropyl, n-butyl, t-butyl, isobutyl, n-hexyl, n-octyl, 2-ethylhexyl, n-dodecyl, and n-hexadecyl.

The aryl group substituted with a nitrogen atom in each of the aforementioned amino groups preferably has 6 to 24 carbon atoms, and more preferably has 6 to 18 carbon atoms. Examples of the aryl group include phenyl and naphthyl, and among these, a phenyl group is preferable. Furthermore, the aryl ring may be fused with an aromatic carbon ring, an aliphatic carbon ring, a heterocyclic ring, or the like.

The heteroaryl group substituted with a nitrogen atom in each of the aforementioned amino groups preferably has 0 to 24 carbon atoms, and more preferably has 1 to 18 carbon atoms. The heterocyclic ring in the heteroaryl group is preferably a 5-membered ring or a 6-membered ring. The heteroatom constituting the heterocyclic ring is preferably a nitrogen atom, an oxygen atom, or a sulfur atom. Examples of the heteroaryl ring include a thiophene ring, a furan ring, a pyrrole ring, a pyrazole ring, an imidazole ring, a triazole ring, an oxazole ring, a thiazole ring, a pyridine ring, a pyrazine ring, a pyrimidine ring, a pyridazine ring, and the like. The heteroaryl ring may be fused with an aromatic carbon ring, an aliphatic carbon ring, a heterocyclic ring, or the like.

The alkyl group, the aryl group, and the heteroaryl group substituted with a nitrogen atom in each of the aforementioned amino groups may have a substituent, and examples of the substituent include the substituents T which will be described later.

Among the substituents, a halogen atom, an alkyl group, an aryl group, a heterocyclic group, an alkoxy group, an alkylthio group, an amino group, an alkylamino group, an arylamino group, and a heteroarylamino group are preferable, and an alkyl group, an aryl group, and alkoxy group, and an alkylthio group are more preferable.

When a nitrogen atom in each of the aforementioned amino groups is an N,N-di-substituted amino group, two substituents may form a ring by being bonded to each other.

Examples of the amino group, alkylamino group, arylamino group, and heteroarylamino group include amino (—NH$_2$), methylamino, ethylamino, n-hexylamino, 2-ethylhexylamino, n-octadecylamino, N,N-dimethylamino, N,N-diethylamino, N,N-bis(n-hexyl)amino, N-methyl-N-n-hexylamino, N,N-bis(2-ethylhexyl)amino, phenylamino, N,N-diphenylamino, N-naphthylamino, N-methyl-N-phenylamino, N-imidazolylamino, pyrrolylamino, and thienylamino.

Among the amino group, alkylamino group, arylamino group, and heteroarylamino group, the alkylamino group and arylamino group are preferable, and the arylamino group is more preferable. —NR$^{21}$R$^{22}$ in Formula (DL-2) which will be described later is preferably a group represented by the following Formula (AM).

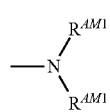

Formula (AM)

In the formula, each of R$^{AM1}$ and R$^{AM2}$ independently represents an alkyl group or an aryl group. R$^{AM1}$ and R$^{AM2}$ may form a ring by being bonded to each other. It is preferable that either R$^{AM1}$ or R$^{AM2}$ represents an aryl group. It is more preferable that R$^{AM1}$ and R$^{AM2}$ both represent an aryl group.

The group formed as a result of bonding of R$^{AM1}$ to R$^{AM2}$ is preferably the following group.

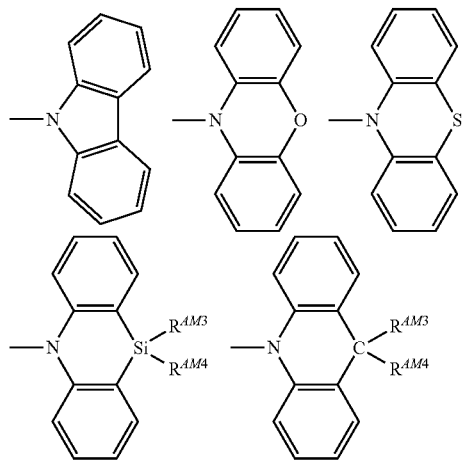

Herein, each of R$^{AM3}$ and R$^{AM4}$ independently represents an alkyl group or an aryl group.

The above ring may have a substituent, and examples of the substituent include the substituents T.

In Formula (DL-1), m1 represents an integer of 0 to 3. m1 is preferably 0 or 1, and more preferably 0.

m2 represents an integer of 1 to 4. m2 is preferably 1 or 2, and more preferably 1.

n1 represents an integer of 1 to 4. n1 is preferably 1 or 2, and more preferably 1.

When n1 is equal to or greater than 2, a plurality of -[(L$^1$)m1-(R$^1$)m2]s may form a ring by being bonded to each other.

In Formula (DL-1), -[(L$^1$)m1-(R$^1$)m2] is preferably in a p (para) position with respect to a nitrogen atom of a pyridine ring or in a p (para) position with respect to E.

In Formula (DL-1), R$^{2a}$ represents a substituent different from -[(L$^1$)m1-(R$^1$)m2], and examples of such a substituent include the substituents T which will be described later. Among the substituents, a halogen atom, an alkyl group, an aryl group, a heterocyclic group, an alkoxy group, and an alkylthio group are preferable, and an alkyl group, an aryl group, a heterocyclic group, an alkoxy group, and an alkylthio group are more preferable. R$^{2a}$ may form a ring by being bonded to -[(L$^1$)m1-(R$^1$)m2].

In Formula (DL-1), l1 represents an integer of 0 to 3. l1 is preferably 0 or 1, and more preferably 0.

When there is a plurality of R$^{2a}$s, the plurality of R$^{2a}$s may form a ring by being bonded to each other.

The bidentate ligand represented by Formula (DL-1) is preferably a bidentate ligand represented by the following Formula (DL-2), and more preferably a bidentate ligand represented by the following Formula (DL-3).

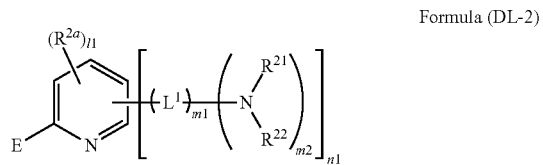

Formula (DL-2)

In Formula (DL-2), E, L$^1$, m1, m2, n1, R$^{2a}$, and l1 have the same definition as that of E, L$^1$, m1, m2, n1, R$^{2a}$, and l1 in Formula (DL-1), and a preferred range thereof is also the same. Each of R$^{21}$ and R$^{22}$ independently represents a hydrogen atom, an alkyl group, an aryl group, or a heteroaryl group. R$^{21}$ and R$^{22}$ may form a ring by being bonded to each other.

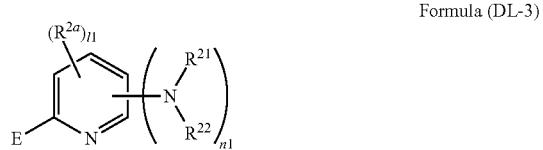

Formula (DL-3)

In Formula (DL-3), E, R$^{21}$, R$^{22}$, n1, R$^{2a}$, and l1 have the same definition as that of E, R$^{21}$, R$^{22}$, n1, R$^{2a}$, and l1 in Formula (DL-2), and a preferred range thereof is also the same.

E represents a group represented by any of Formulae (E-1) to (E-6).

In Formula (DL-3), R in Formulae (E-1) to (E-5) represents a halogen atom, an alkyl group, an alkoxy group, an aryl group, or a heteroaryl group.

Examples of the halogen atom represented by R in Formulae (E-1) to (E-5) include a fluorine atom, a chlorine atom, a bromine atom, and an iodine atom. Among these, a fluorine atom, a chlorine atom, and a bromine atom are preferable, and a fluorine atom is more preferable.

The alkyl group represented by R in Formulae (E-1) to (E-5) is a linear or branched alkyl group. The alkyl group preferably has 1 to 20 carbon atoms, and more preferably has 1 to 18 carbon atoms. Examples of such an alkyl group include methyl, ethyl, isopropyl, n-butyl, t-butyl, n-hexyl, n-octyl, 2-ethylhexyl, n-dodecyl, and n-hexadecyl. Herein, the alkyl group is preferably an alkyl group substituted with a halogen atom, and more preferably an alkyl group substituted with a fluorine atom. Among these, a perfluoroalkyl group, and particularly, perfluoromethyl is preferable.

The alkoxy group represented by R in Formulae (E-1) to (E-5) is a linear or branched alkoxy group. The alkoxy group preferably has 1 to 20 carbon atoms, and more preferably has 1 to 18 carbon atoms. Examples of such an alkoxy group include methoxy, ethoxy, isopropyloxy, n-butyloxy, s-butyloxy, n-hexyloxy, n-octyloxy, 2-ethylhexyloxy, n-dodecyloxy, and n-hexadecyloxy.

The aryl group represented by R in Formulae (E-1) to (E-5) is preferably an aryl group having 6 to 20 carbon atoms, and examples thereof include phenyl and naphthyl. As the aryl group, a phenyl group which may have a substituent is preferable.

The heteroaryl group represented by R in Formulae (E-1) to (E-5) is preferably a heteroaryl group as a 5-membered ring or a 6-membered ring. The heteroaryl ring in the heteroaryl group may be fused with an aryl ring, an alicyclic ring, or a heterocyclic ring and may have a substituent. Examples of the substituent include the substituents T which will be described later.

As the ring-constituting heteroatom of the heteroaryl ring, an oxygen atom, a sulfur atom, a nitrogen atom, and a selenium atom are preferable.

Examples of the heteroaryl ring in the heteroaryl group include a furan ring, a thiophene ring, and a pyrrole ring. Among these, a thiophene ring is preferable.

m in Formulae (E-1) to (E-6) represents an integer of equal to or greater than 0. m is preferably 1 or 2, and more preferably 1.

Among Formulae (E-1) to (E-6), Formulae (E-1), (E-2), (E-4), (E-5), and (E-6) are preferable as E; Formulae (E-2), (E-4), and (E-5) are more preferable as E; Formulae (E-2) and (E-5) are even more preferable as E; and Formula (E-2) is particularly preferable as E.

Specific examples of the ligand LD of the first embodiment will be shown below, but the present invention is not limited thereto.

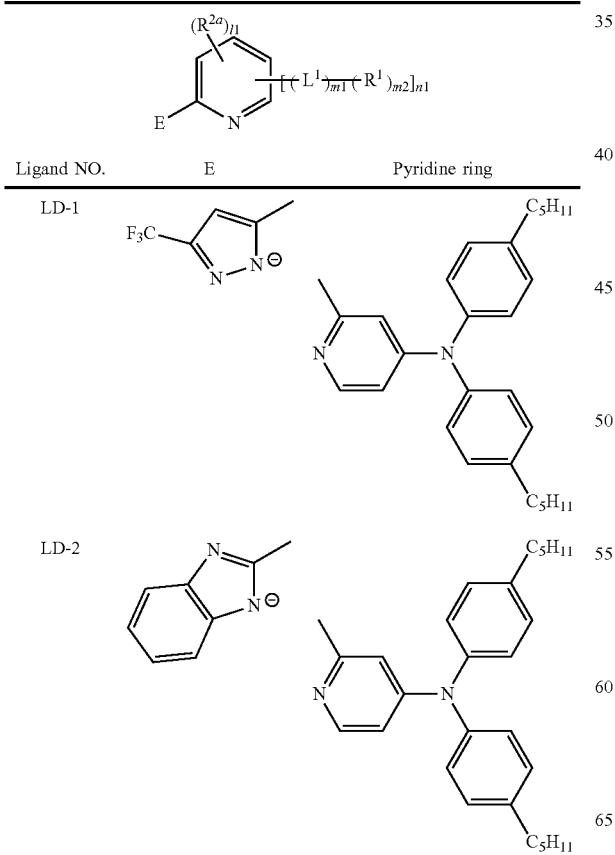

-continued

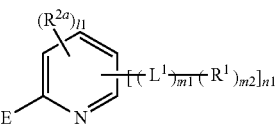

| Ligand NO. | E | Pyridine ring |
|---|---|---|
| LD-3 | 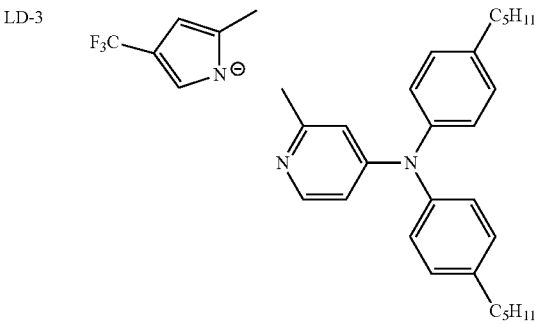 | |
| LD-4 | 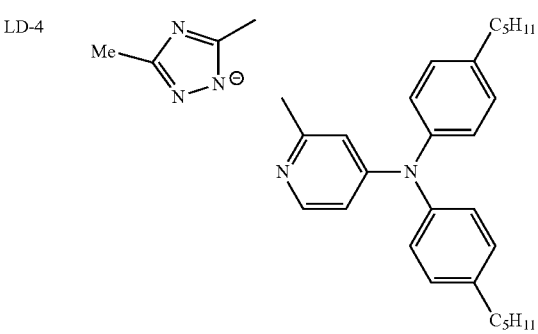 | |
| LD-5 | 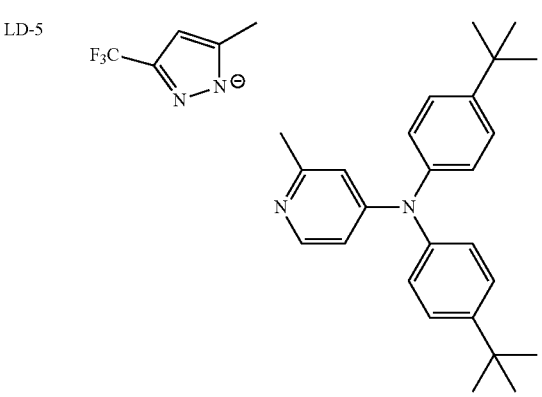 | |

-continued
| Ligand NO. | E | Pyridine ring |
|---|---|---|
| LD-6 | | |
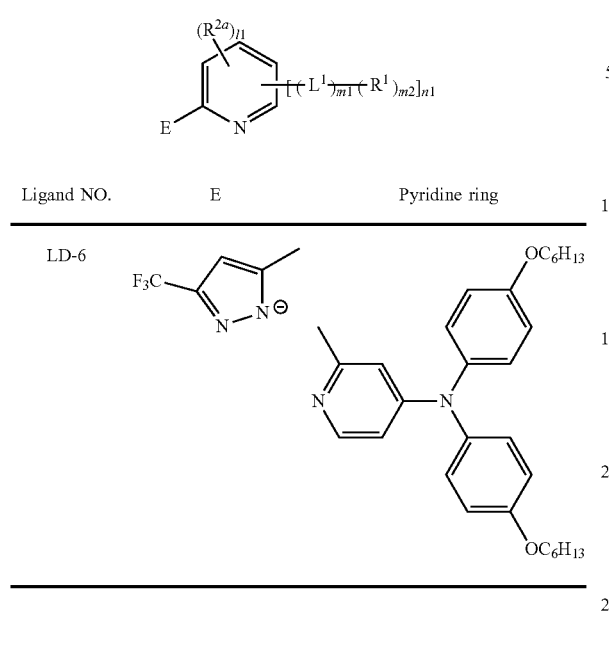
| Ligand NO. | E | Pyridine ring |
|---|---|---|
| LD-7 | | |
| LD-8 | | |
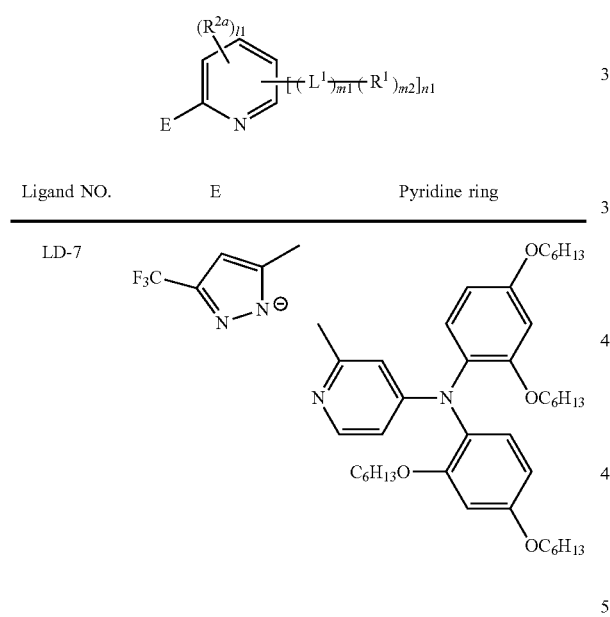
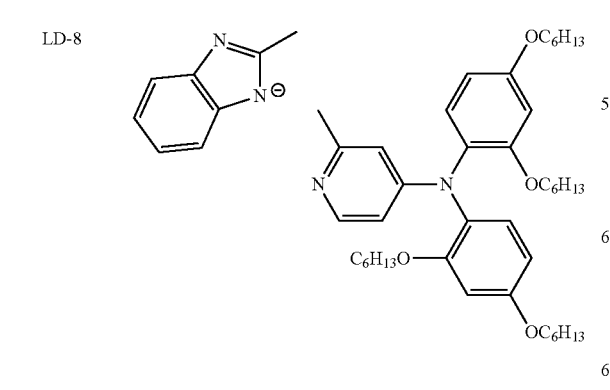
-continued
| Ligand NO. | E | Pyridine ring |
|---|---|---|
| LD-9 | | |
| LD-10 | | |
| LD-11 | | |
| LD-12 | | |
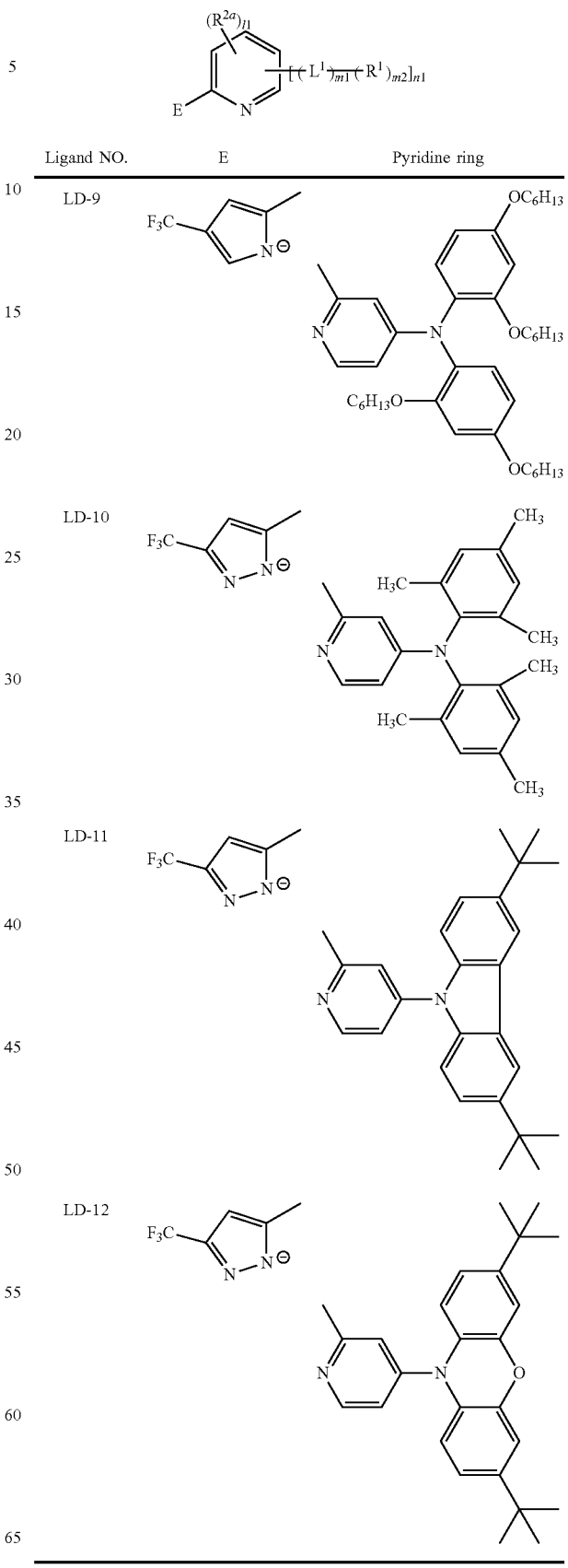

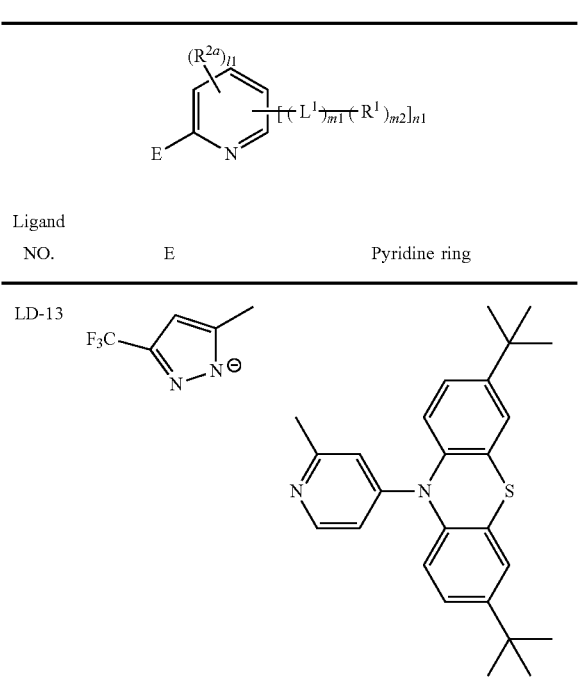
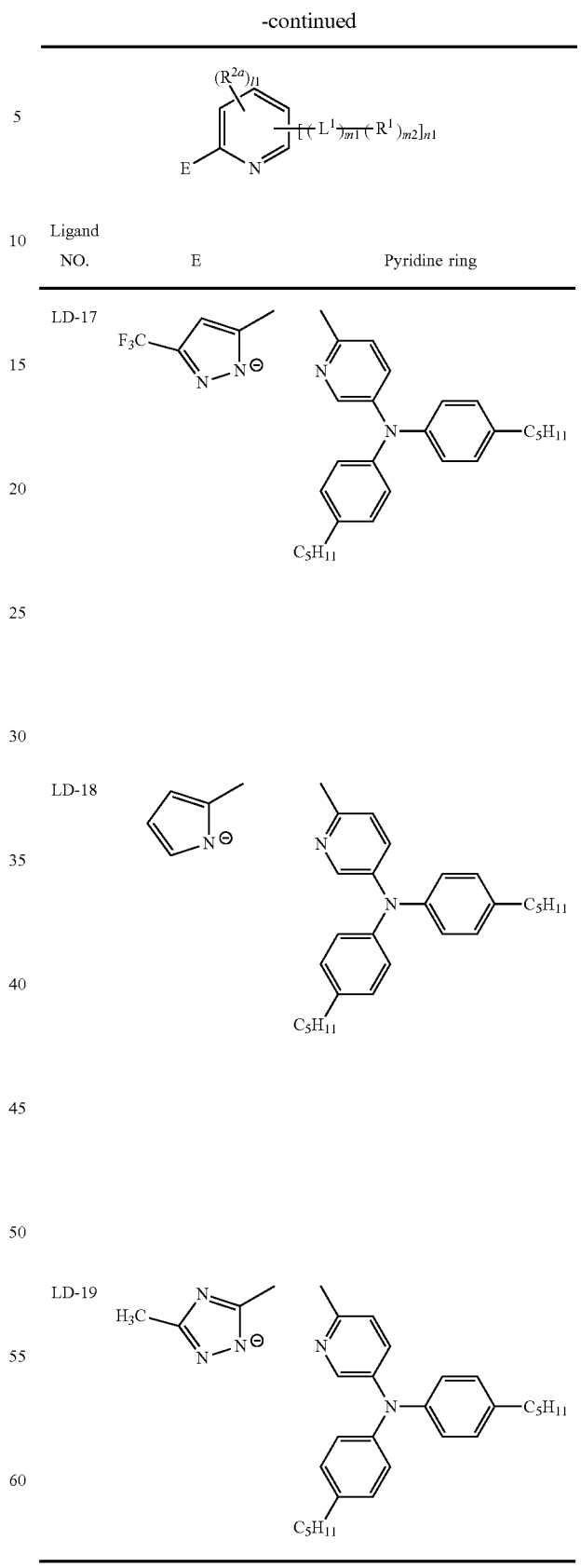

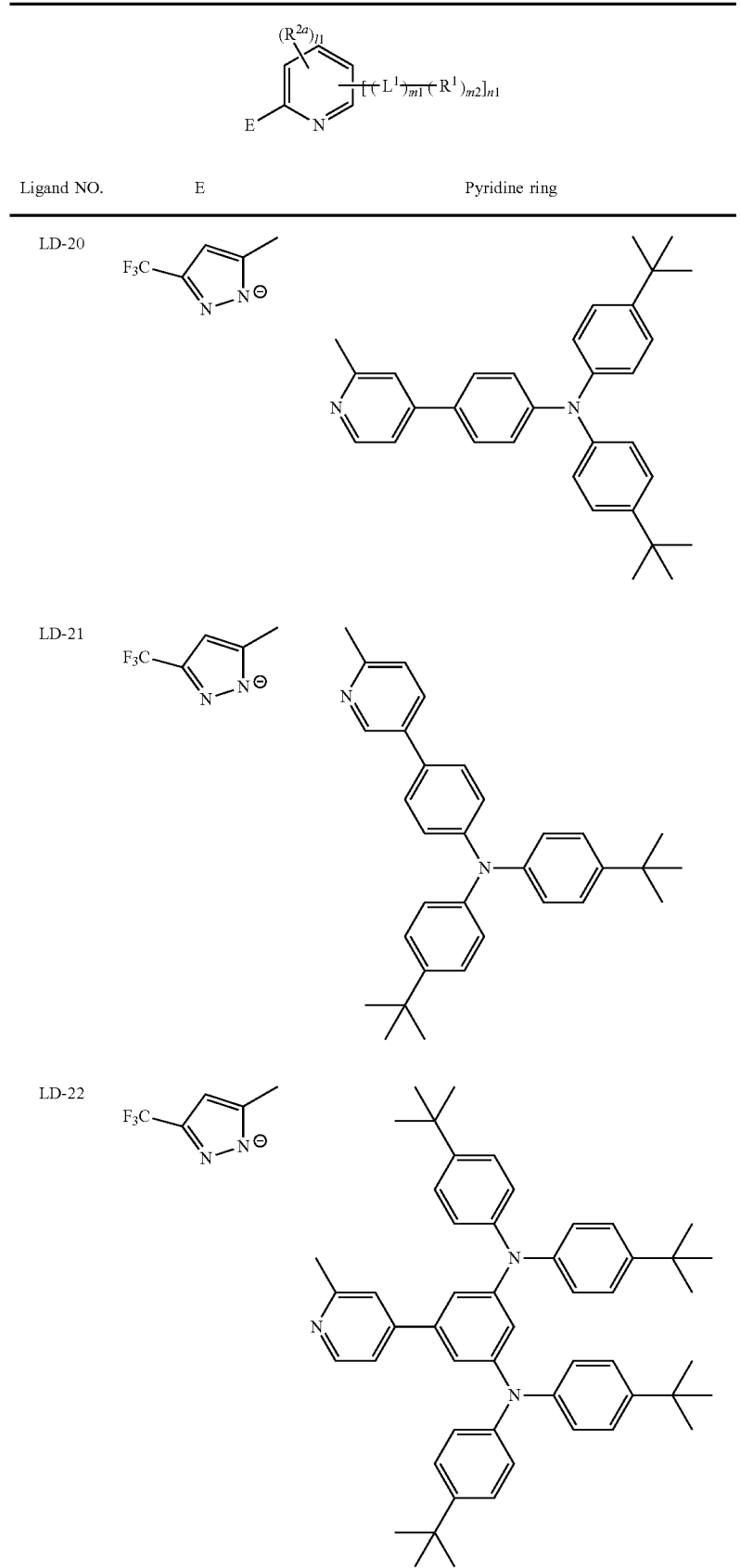

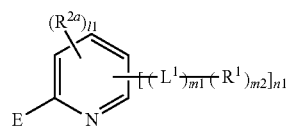
| Ligand NO. | E | Pyridine ring |
|---|---|---|
| LD-23 | 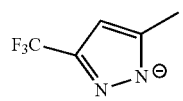 | 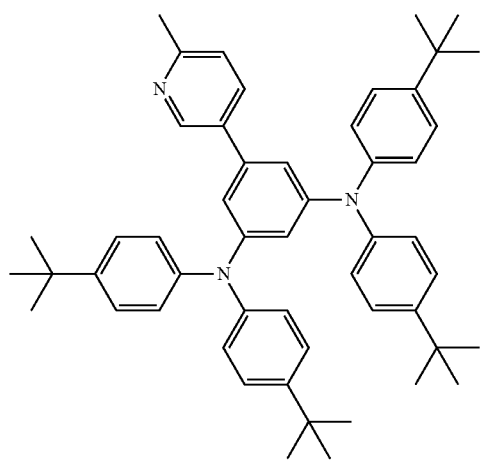 [SMILES: Cc1ccc(-c2cc(N(c3ccc(C(C)(C)C)cc3)c3ccc(C(C)(C)C)cc3)cc(N(c3ccc(C(C)(C)C)cc3)c3ccc(C(C)(C)C)cc3)c2)cn1] |
| LD-24 | 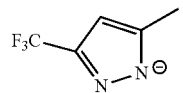 | 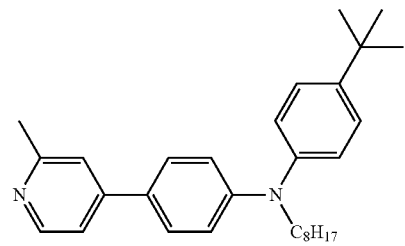 |
| LD-25 | 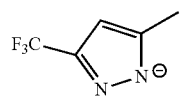 | 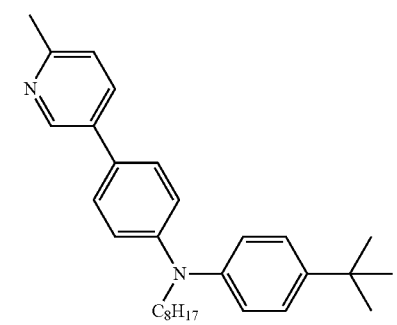 |

| Ligand NO. | E | Pyridine ring |
|---|---|---|
| LD-26 | 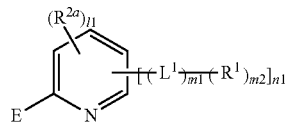 | 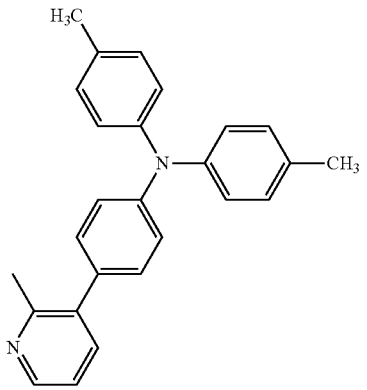 [SMILES: Cc1ccc(N(c2ccc(C)cc2)c2ccc(-c3cccnc3C)cc2)cc1] |
| LD-27 |  | 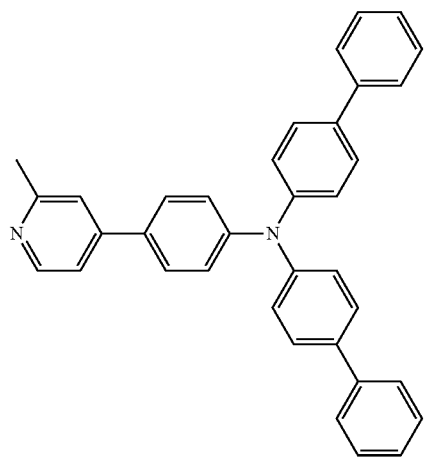 [SMILES: Cc1cc(-c2ccc(N(c3ccc(-c4ccccc4)cc3)c3ccc(-c4ccccc4)cc3)cc2)ccn1] |
| LD-28 | 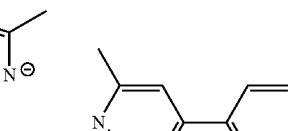 | 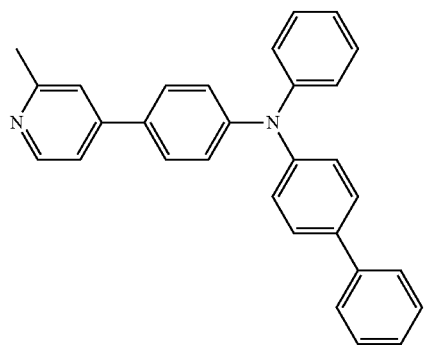 [SMILES: Cc1cc(-c2ccc(N(c3ccccc3)c3ccc(-c4ccccc4)cc3)cc2)ccn1] |
| LD-29 | 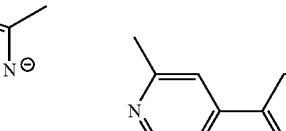 | 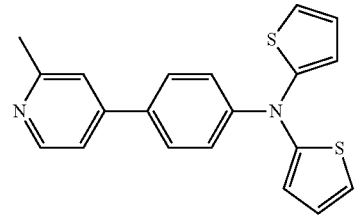 [SMILES: Cc1cc(-c2ccc(N(c3cccs3)c3cccs3)cc2)ccn1] |

-continued
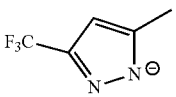
| Ligand NO. | E | Pyridine ring |
|---|---|---|
| LD-30 | 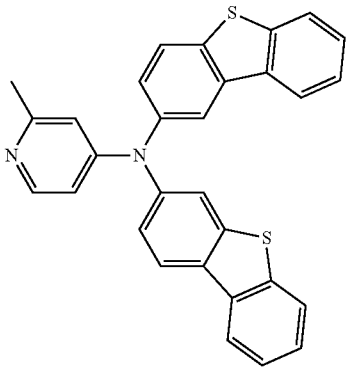 | 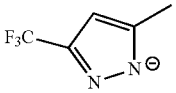 |
| LD-31 | 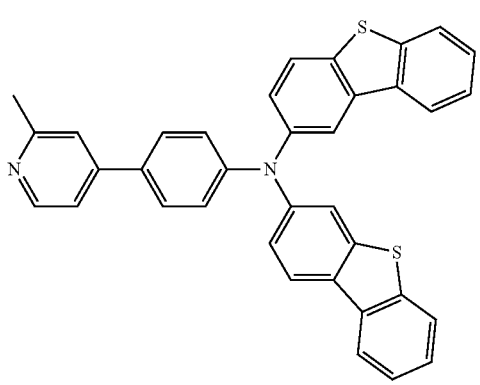 | 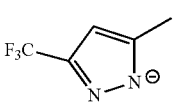 |
| LD-32 | 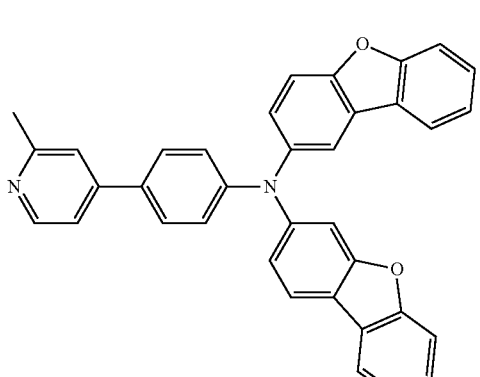 | |

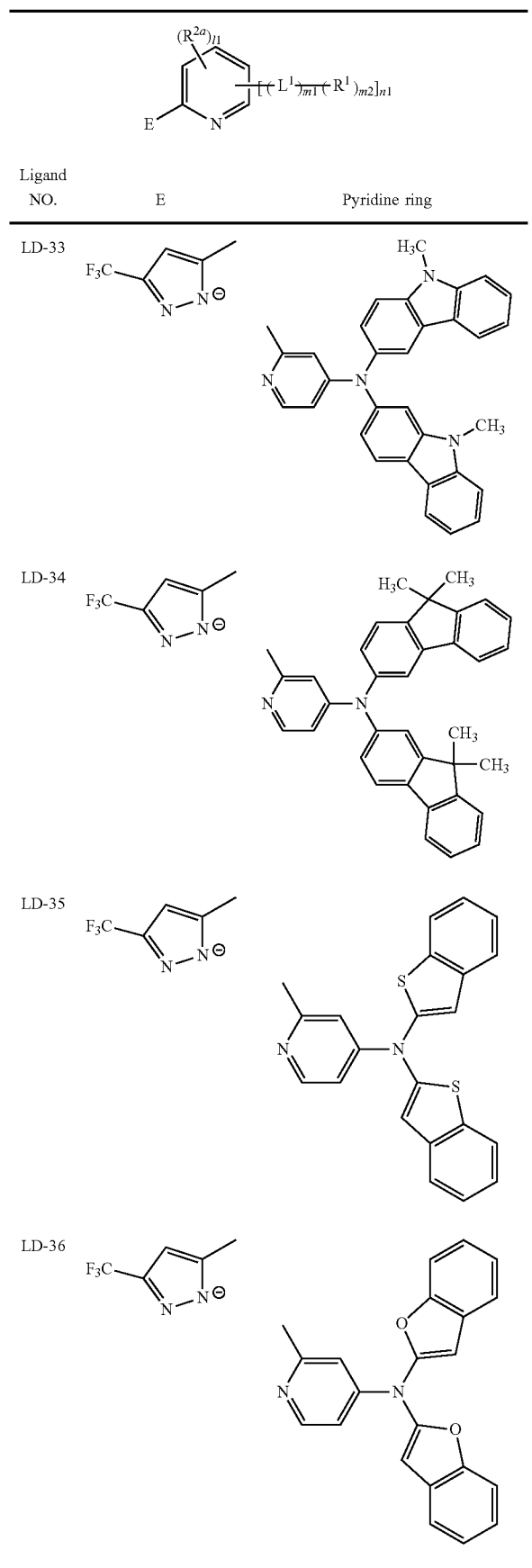
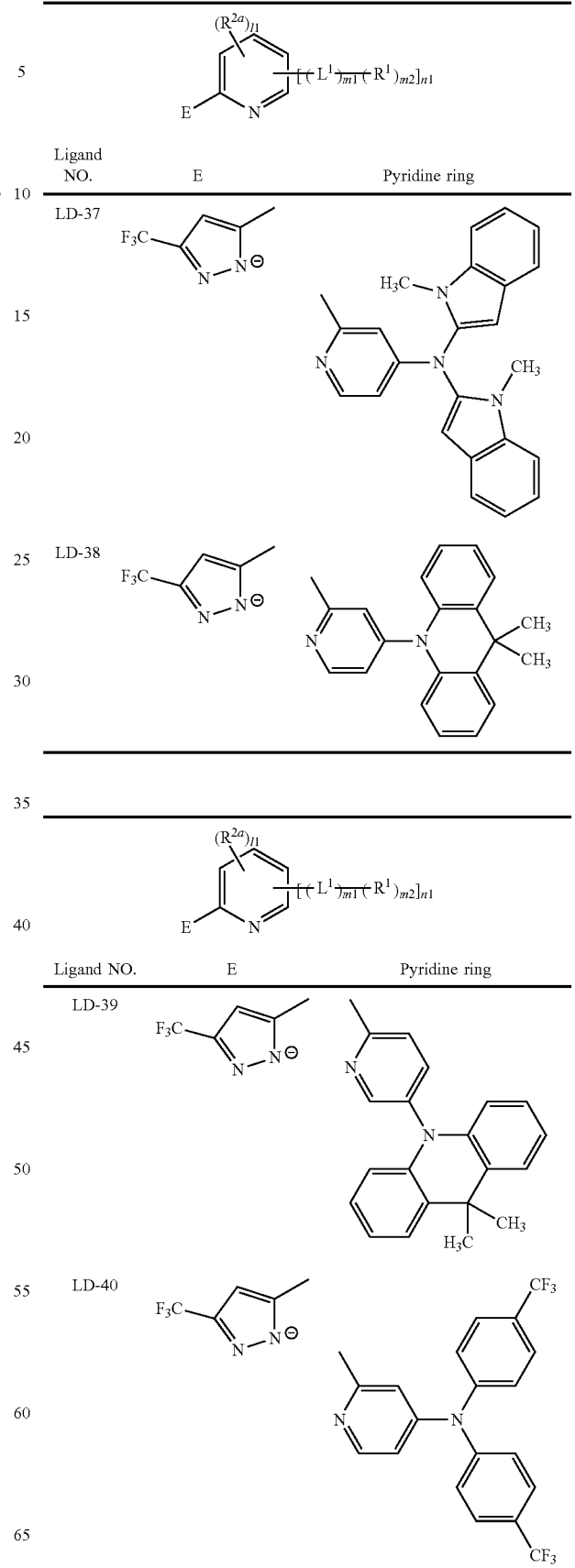

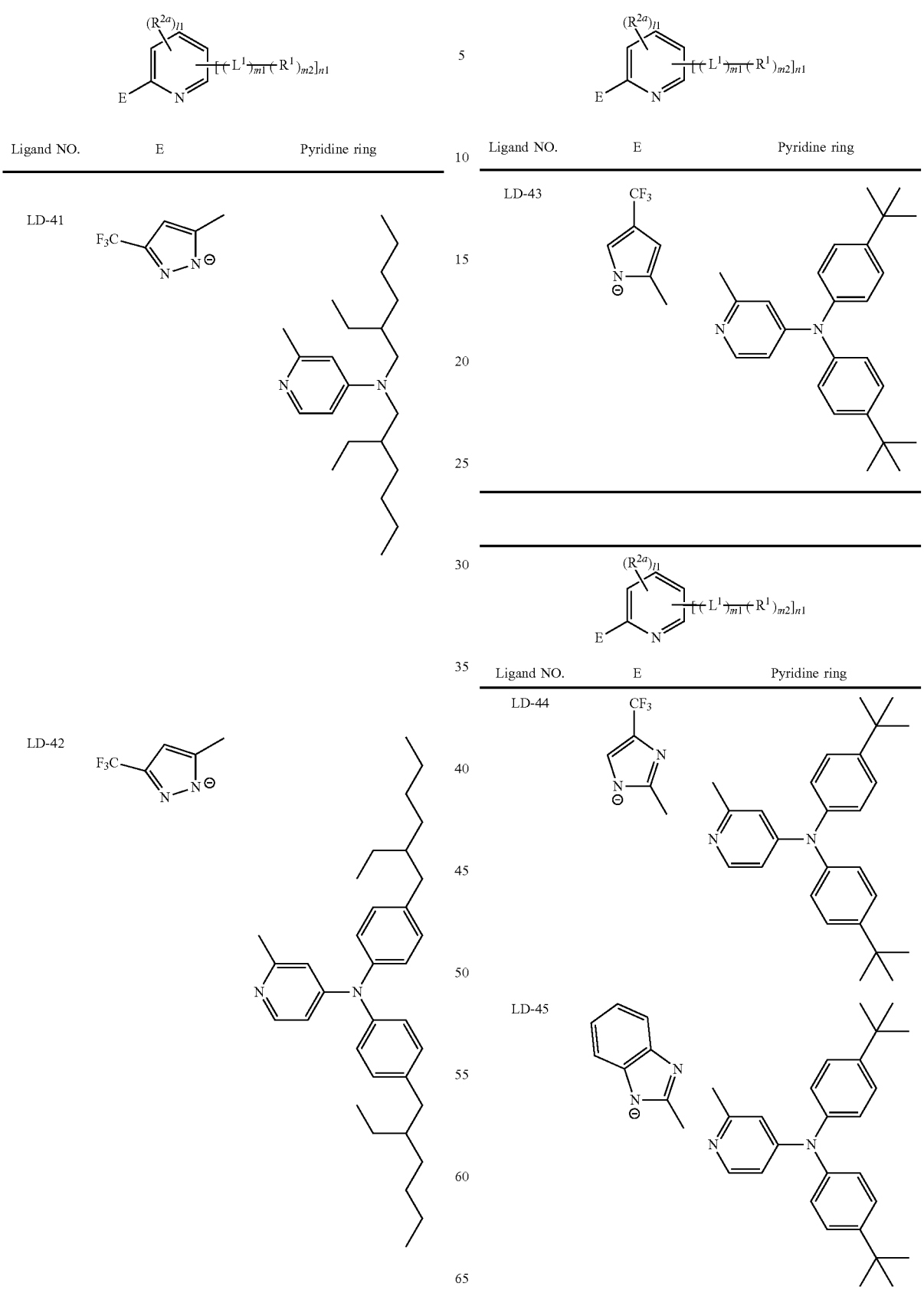

-continued

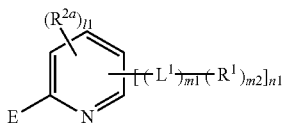

| Ligand NO. | E | Pyridine ring |
|---|---|---|
| LD-46 | NC | |

—Ligand $Z^1$—

$Z^1$ represents a monodentate ligand. Examples of $Z^1$ include a monodentate ligand, which forms a coordinate bond through a group selected from the group consisting of an acyloxy group, an acylthio group, a thioacyloxy group, a thioacylthio group, an acylaminooxy group, a thiocarbamate group, a dithiocarbamate group, a thiocarbonate group, a dithiocarbonate group, a trithiocarbonate group, an acyl group, a thiocyanate group, an isothiocyanate group, a cyanate group, an isocyanate group, a selenate group, an isoselenate group, an isoselenocyanate group, a cyano group, an alkylthio group, an arylthio group, an alkoxy group, and an aryloxy group, and a monodentate ligand which is selected from the group consisting of a halogen atom, a phosphine ligand, carbonyl, dialkyl ketone, carbonamide, thiocarbonamide, and thiourea. $Z^1$ is preferably an isothiocyanate group, an isoselenocyanate group, an isocyanate group, a halogen atom, or a cyano group. When the ligand $Z^1$ includes an alkyl moiety, an alkenyl moiety, an alkynyl moiety, an alkylene moiety, and the like, these may be linear or branched or may be substituted or unsubstituted. Furthermore, when the ligand $Z^1$ includes an aryl moiety, a heterocyclic ring moiety, a cycloalkyl moiety, and the like, these may be substituted or unsubstituted or may form a monocyclic ring or a fused ring.

—Counterion CI for Neutralizing Charge—

CI represents a counterion used when a counterion is necessary for neutralizing the charge. Generally, whether a dye is a cation or an anion or whether a dye carries a net ionic charge depends on the metal, ligand, and substituent in the metal complex dye.

Because the substituent has a dissociative group or the like, the metal complex dye may be dissociated and carry a negative charge. In this case, due to CI, the overall charge of the metal complex dye becomes electrically neutral.

When the counterion CI is a positive counterion, the counterion CI is, for example, an inorganic or organic ammonium ion (such as a tetraalkylammonium ion or a pyridinium ion), a phosphonium ion (such as a tetraalkylphosphonium ion or an alkyltriphenyl phosphonium ion), an alkali metal ion, a metal complex ion, or a proton. As the positive counterion, an inorganic or organic ammonium ion (a triethylammonium ion, a tetrabutylammonium ion, or the like) and a proton are preferable.

When the counterion CI is a negative counterion, for example, the counterion CI may be an inorganic anion or an organic anion. Examples thereof include a hydroxide ion, a halogen anion (such as a fluoride ion, a chloride ion, a bromide ion, or an iodide ion), a substituted or unsubstituted alkylcarboxylate ion (an acetate ion, a trifluoroacetate ion, or the like), a substituted or unsubstituted arylcarboxylate ion (a benzoate ion or the like), a substituted or unsubstituted alkylsulfonate ion (a methanesulfonate ion, a trifluoromethanesulfonate ion, or the like), a substituted or unsubstituted arylsulfonate ion (such as a p-toluenesulfonate ion or a p-chlorobenzenesulfonate ion), an aryldisulfonate ion (such as a 1,3-benzene disulfonate ion, a 1,5-naphthalene disulfonate ion, or a 2,6-naphthalene disulfonate ion), an alkylsulfate ion (such as a methyl sulfate ion), a sulfate ion, a thiocyanate ion, a perchlorate ion, a tetrafluoroborate ion, a hexafluorophosphate ion, and a picrate ion. Furthermore, as a charge balancing counterion, either an ionic polymer or other dyes carrying a charge opposite to the charge of the dye may be used. In addition, it is possible to use a metal complex ion [such as bis(benzene-1,2-dithiolato)nickel (III)]. As the negative counterion, a halogen anion, a substituted or unsubstituted alkylcarboxylate ion, a substituted or unsubstituted alkylsulfonate ion, a substituted or unsubstituted arylsulfonate ion, an aryldisulfonate ion, a perchlorate ion, and a hexafluorophosphate ion are preferable, and a halogen anion and a hexafluorophosphate ion are more preferable.

In the first embodiment, the metal complex dye represented by Formula (I) is preferably a metal complex dye represented by the following Formula (II), and more preferably a metal complex dye represented by the following Formula (III).

Formula (II)

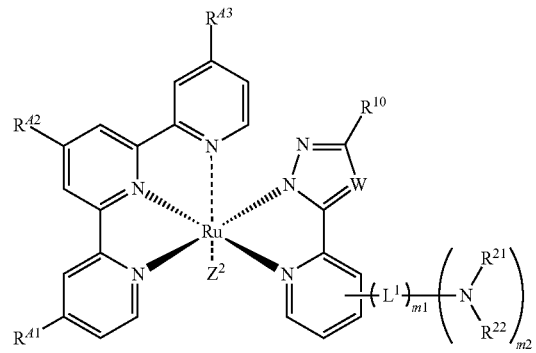

In Formula (II), $R^{41}$ to $R^{43}$ have the same definition as that of $R^{41}$ to $R^{43}$ in Formula (AL-3). $R^{21}$, $R^{22}$, $L^1$, m1, and $m^2$ have the same definition as that of $R^{21}$, $R^{22}$, $L^1$, m1, and m2 in Formula (DL-2), and a preferred range thereof is also the same. W represents a nitrogen atom or CH. $R^{10}$ represents a hydrogen atom, an alkyl group, a perfluoroalkyl group, an aryl group, or a heteroaryl group. $Z^2$ represents an isothiocyanate group, an isoselenocyanate group, an isocyanate group, a halogen atom, or a cyano group.

Formula (III)

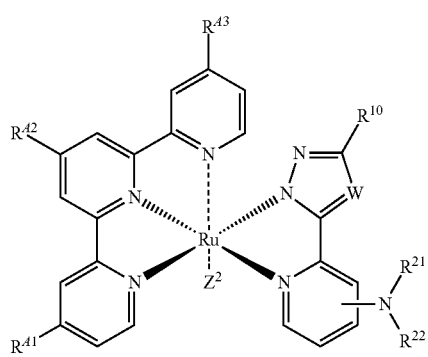

In Formula (III), $R^{A1}$ to $R^{A3}$ have the same definition as that of $R^{A1}$ to $R^{A3}$ in Formula (AL-3). W, $R^{21}$, $R^{22}$, $R^{10}$, and $Z^2$ have the same definition as that of W, $R^{21}$, $R^{22}$, $R^{10}$, and $Z^2$ in Formula (II), and a preferred range thereof is also the same.

Specific examples of the metal complex dye represented by Formula (I) of the first embodiment will be shown below, but the present invention is not limited thereto.

The ligand is in a state of forming a coordinate bond with a metal atom. That is, the atom forming a coordinate bond through an anion is represented by an anion, but the ligand does not need to form a coordinate bond through an anion.

Furthermore, although the counterion is not shown in the metal complex dye, the counterion is not unnecessary, and the metal complex dye can retain a certain counterion. Examples of the counterion include the aforementioned CI.

DN-1

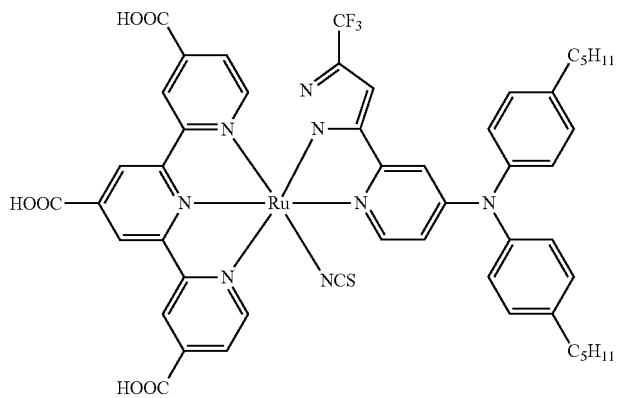

DN-2

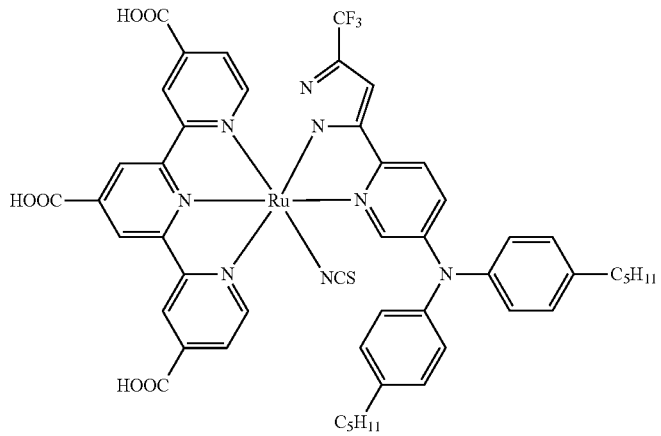

DN-3

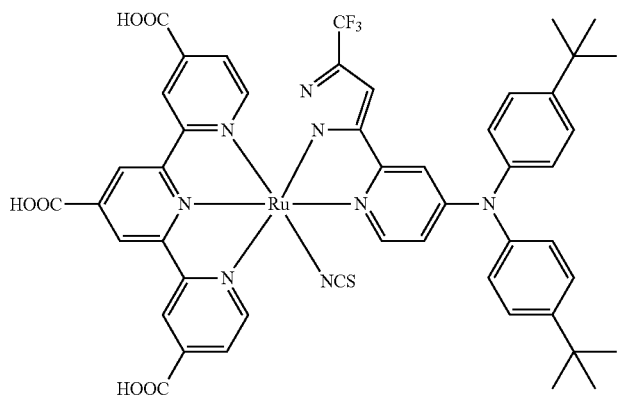

-continued
DN-4
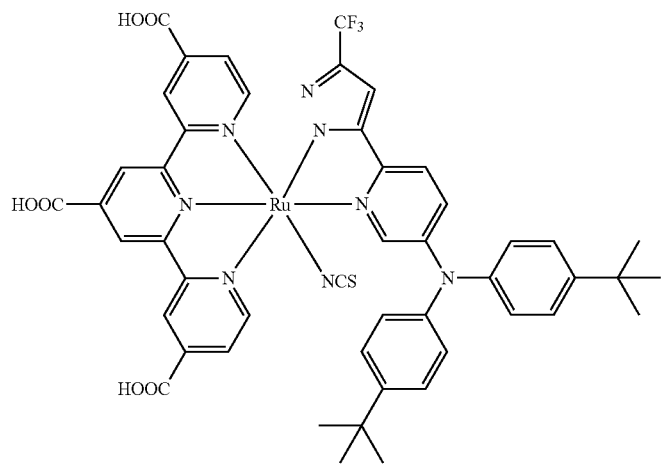
DN-5
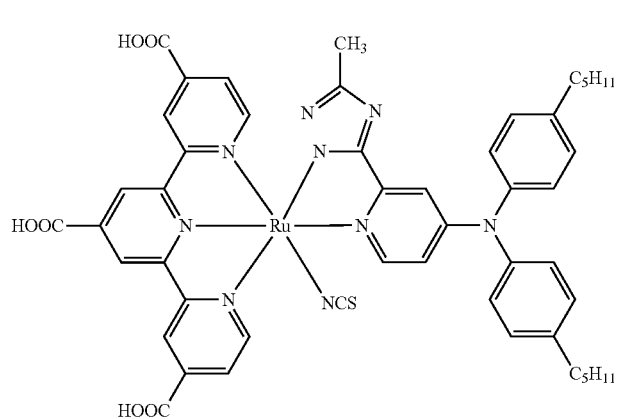
DN-6
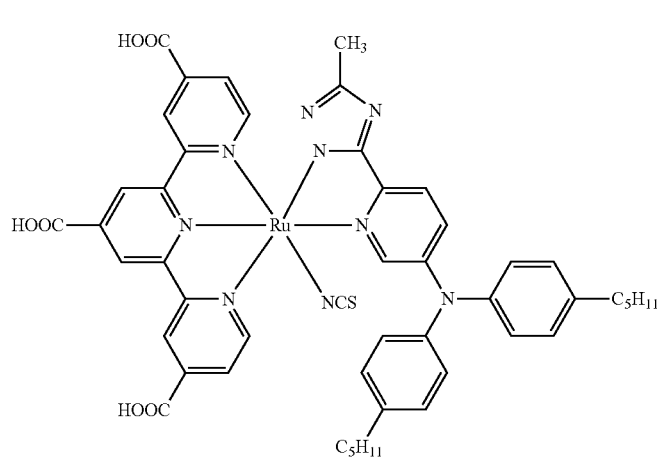

-continued
DN-7
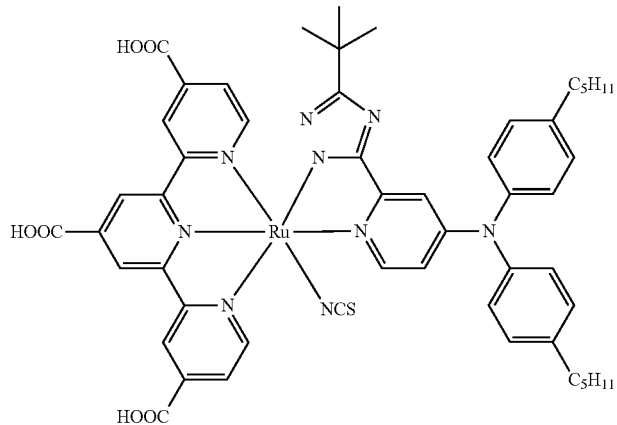
DN-8
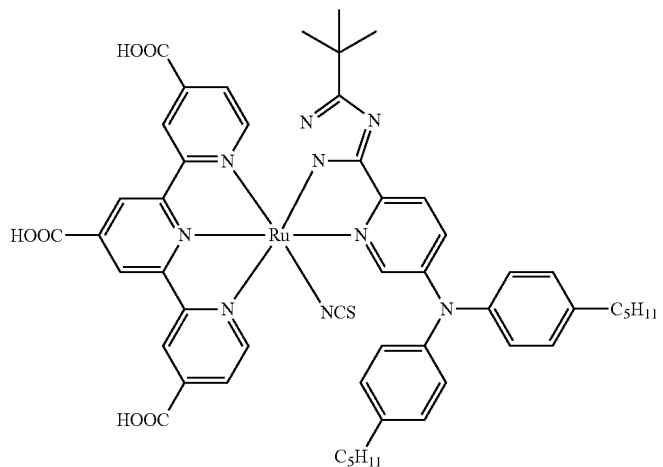
DN-9
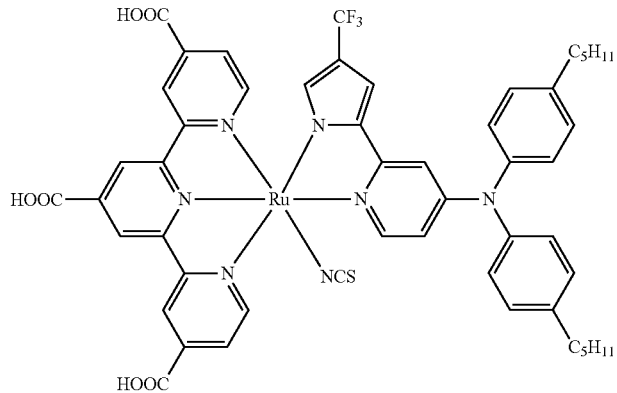

-continued
DN-10
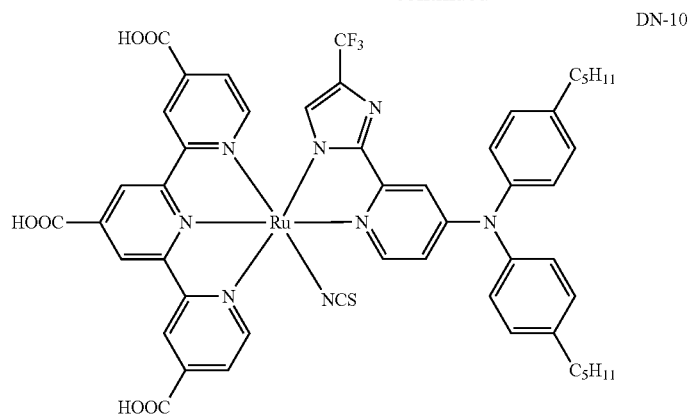
DN-11
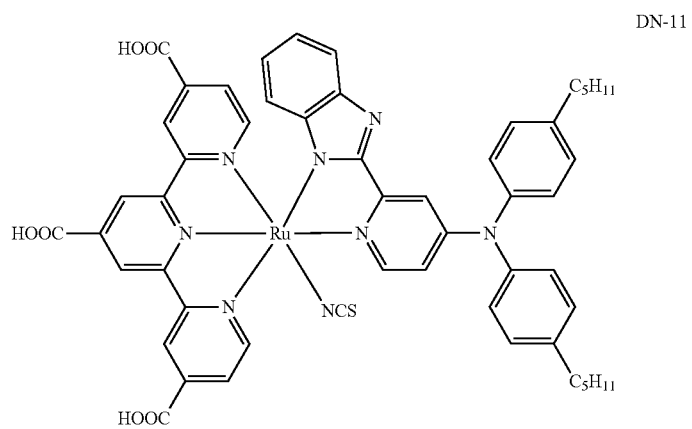
DN-12
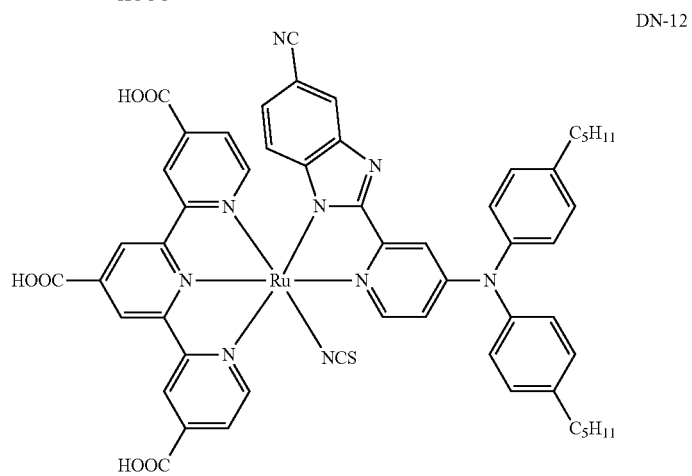
DN-13
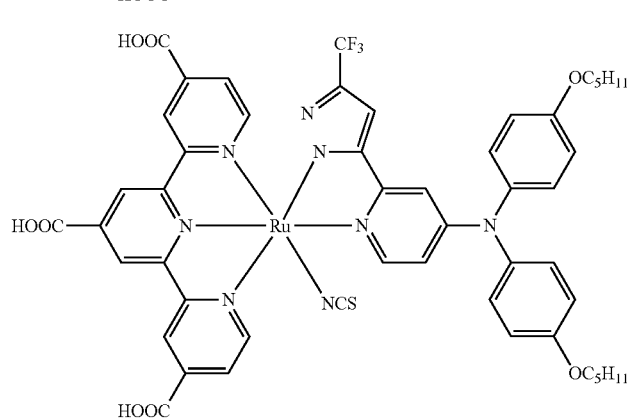

-continued
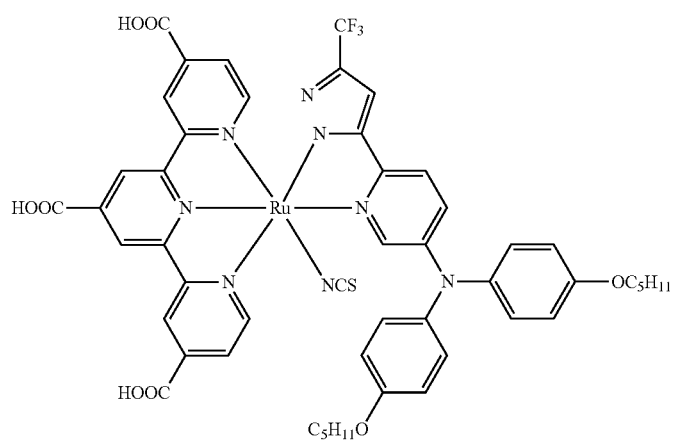
DN-14
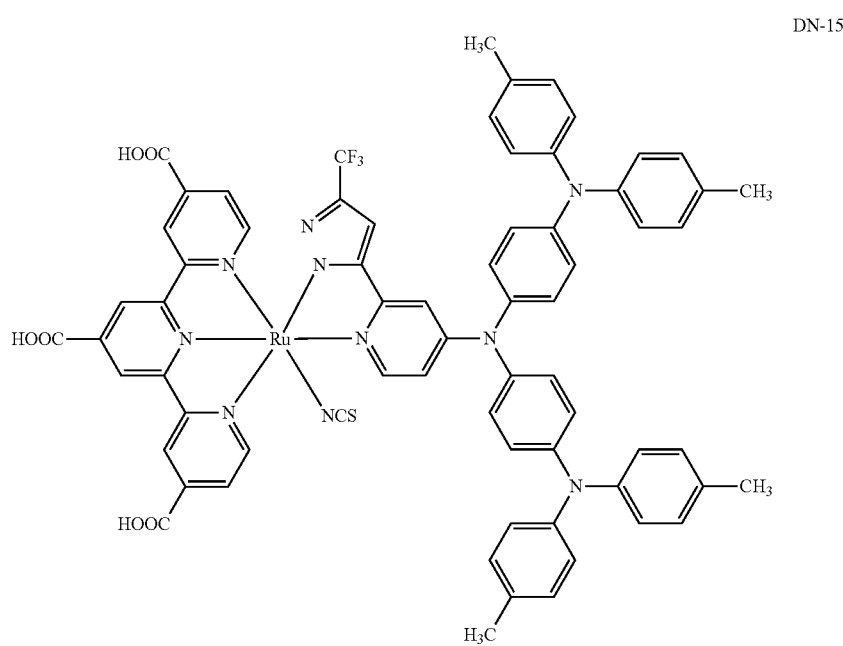
DN-15
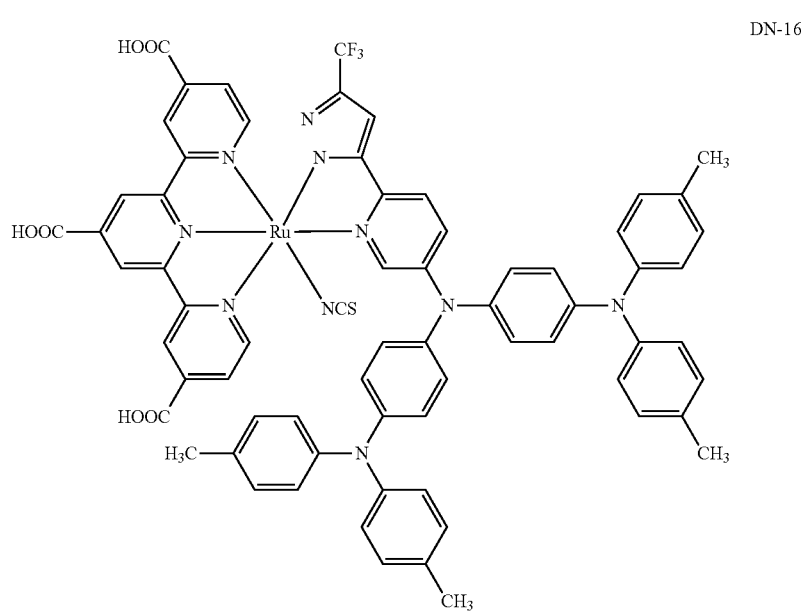
DN-16

-continued
DN-17
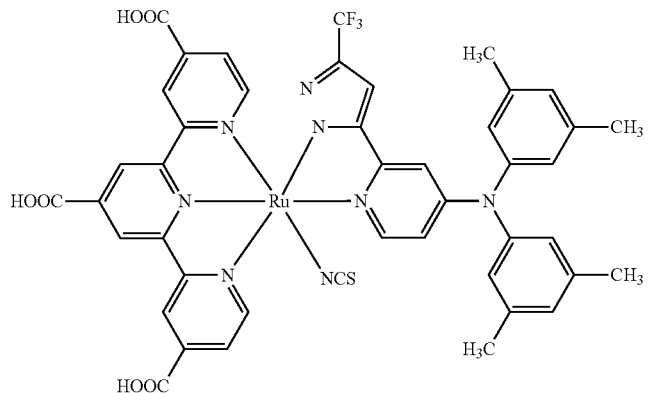
DN-18
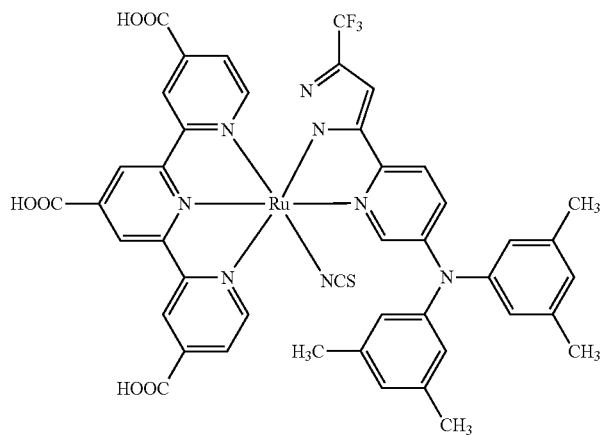
DN-19
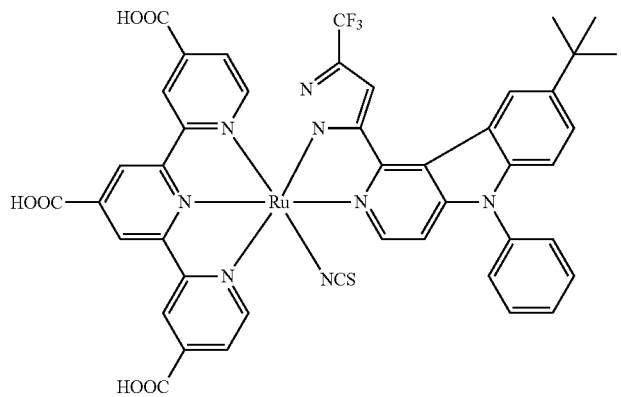
DN-20
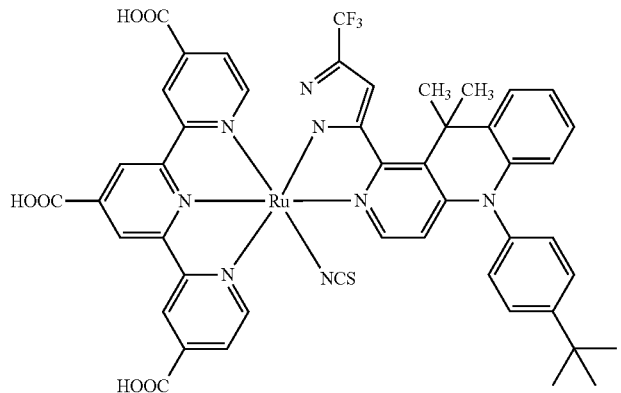

-continued
DN-21
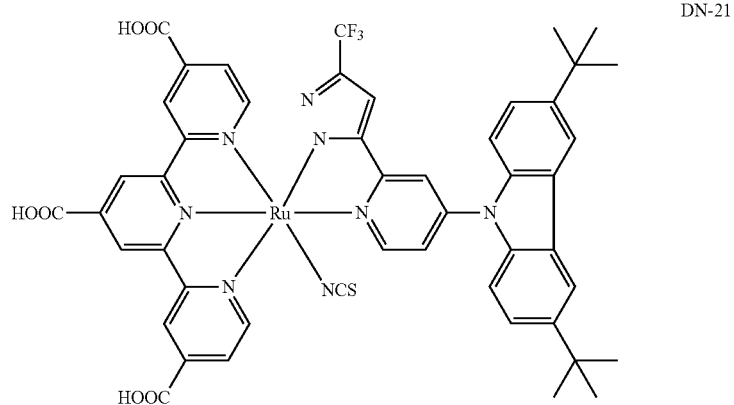
DN-22
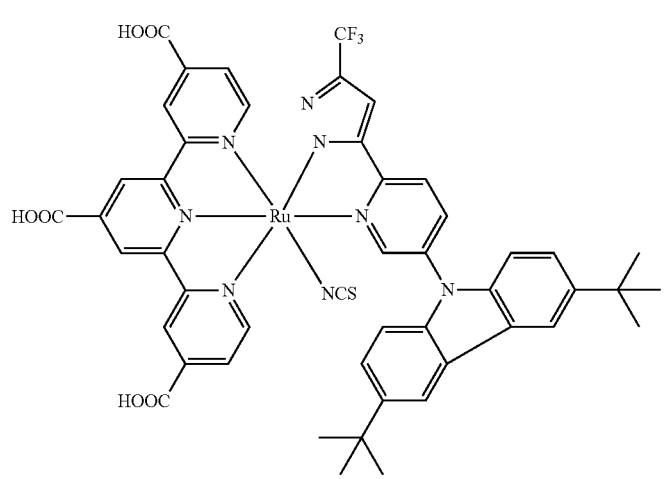
DN-23
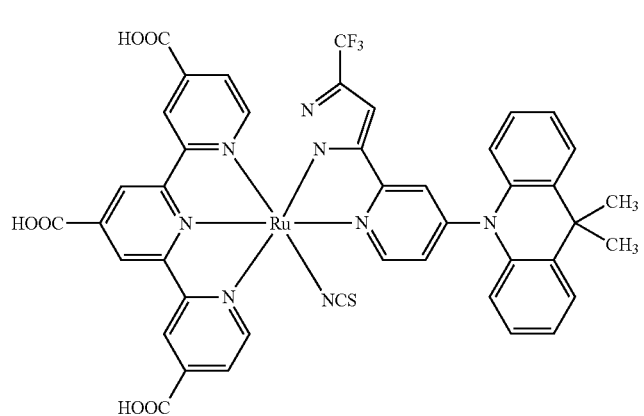
DN-24
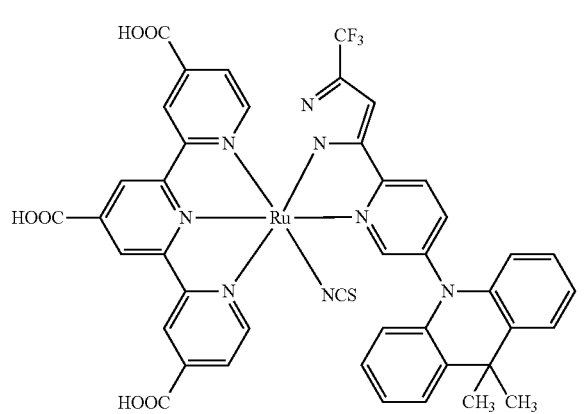

-continued
DN-25
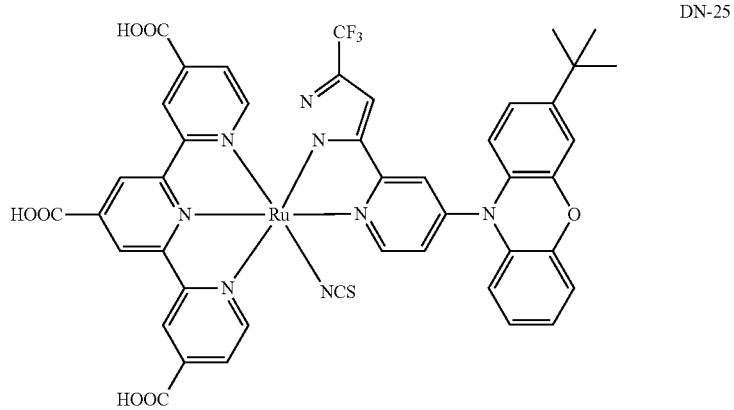
DN-26
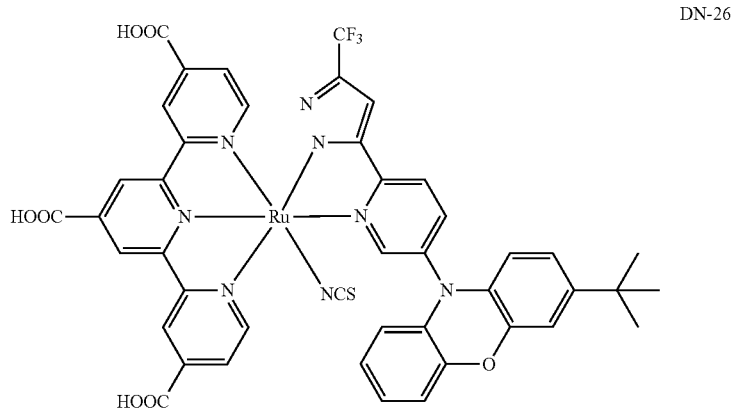
DN-27
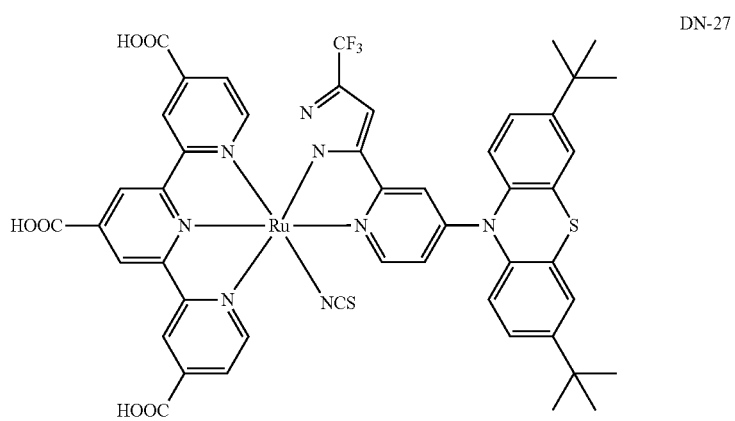
DN-28
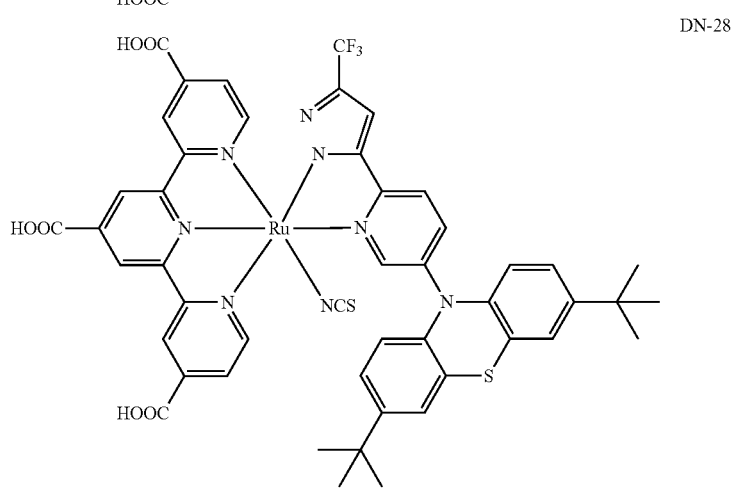

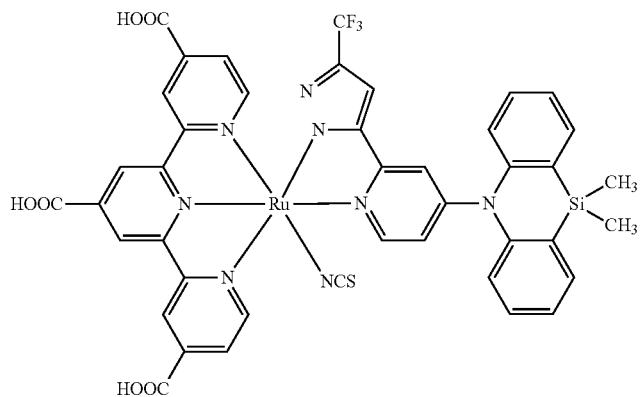
DN-29
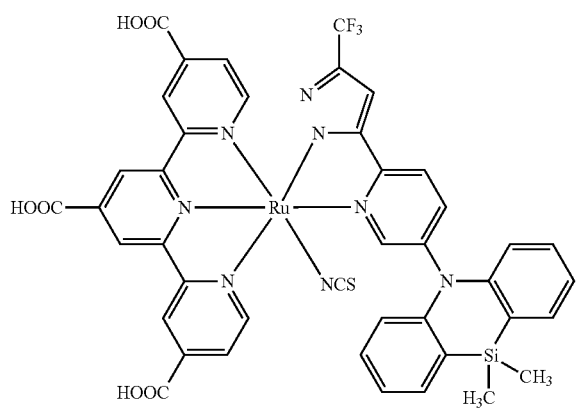
DN-30
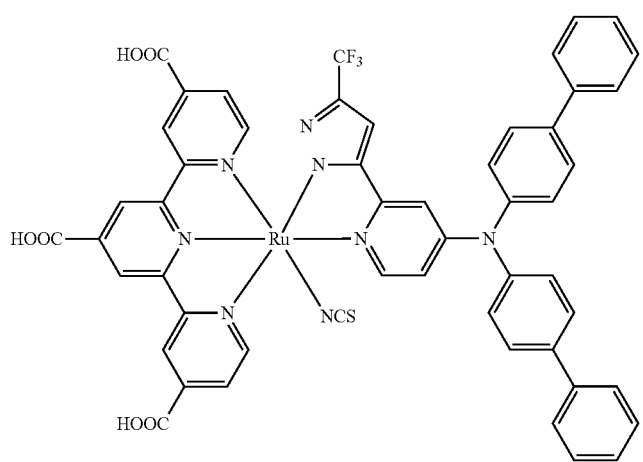
DN-31

-continued
DN-32
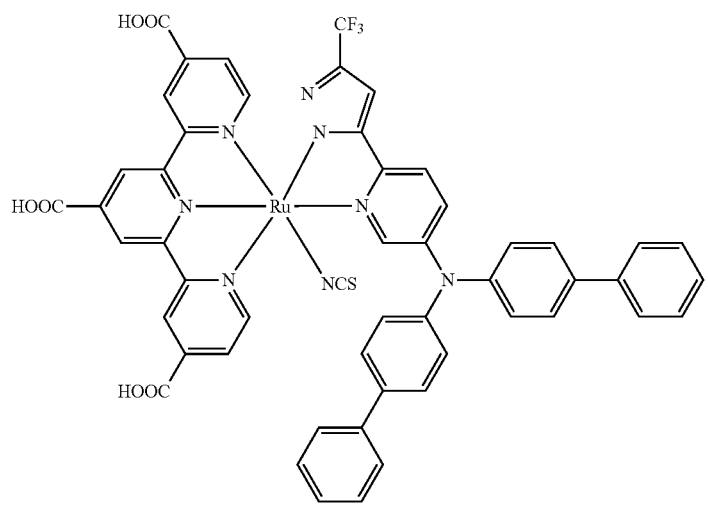
DN-33
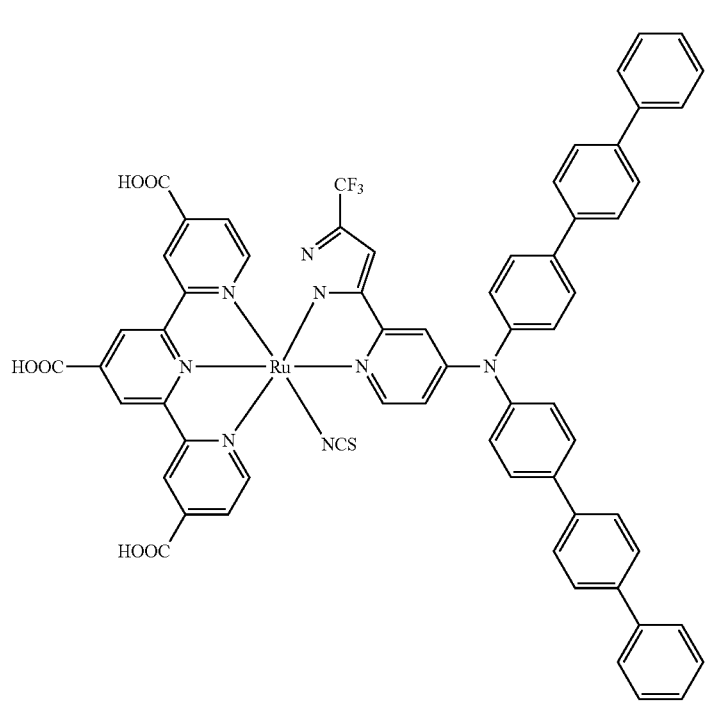
DN-34
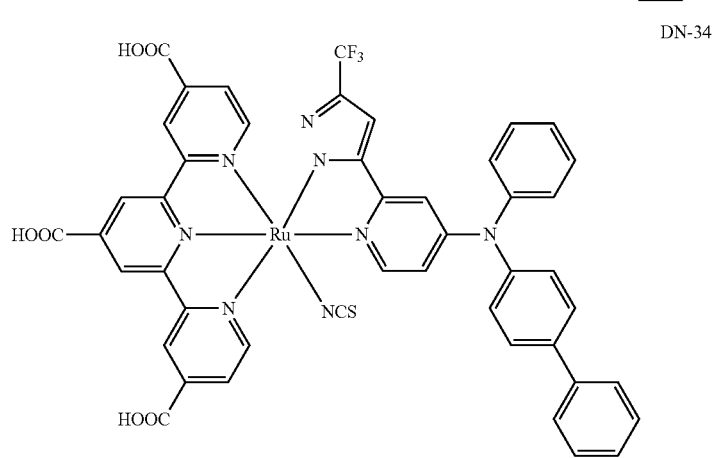

DN-35
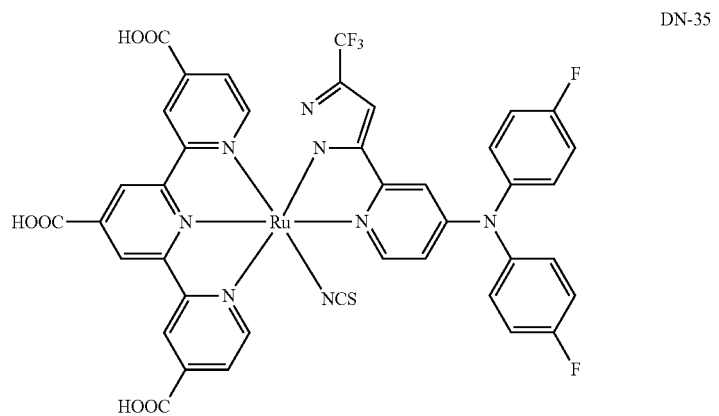
DN-36
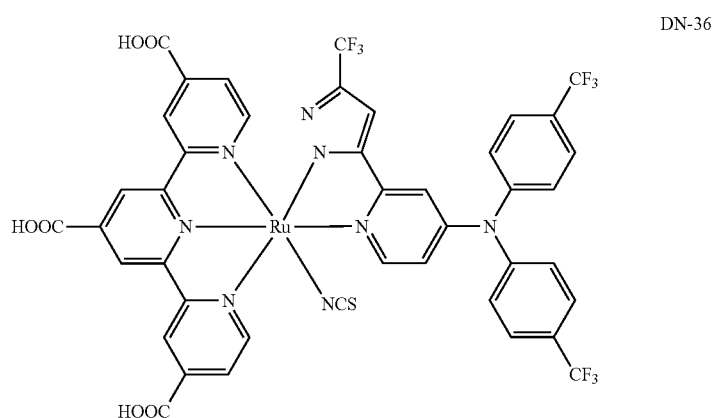
DN-37
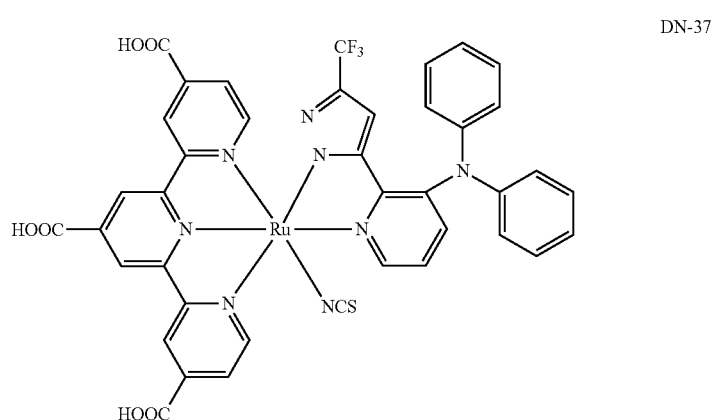
DN-38
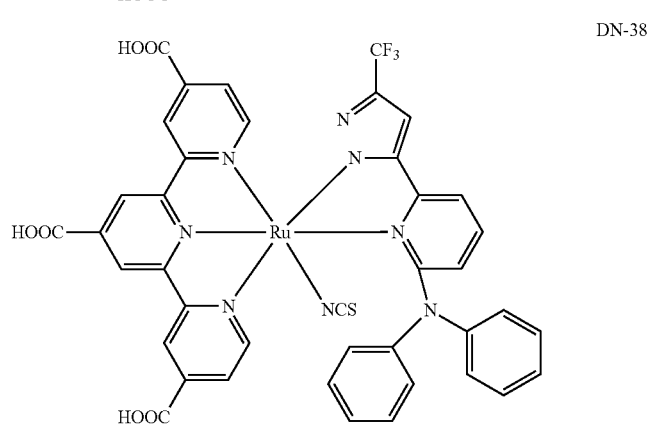

-continued
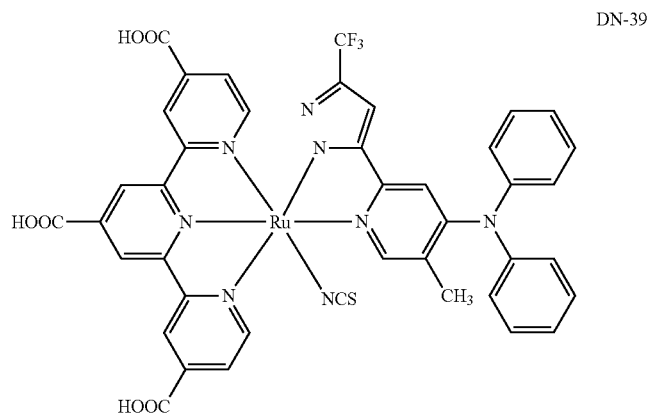
DN-39
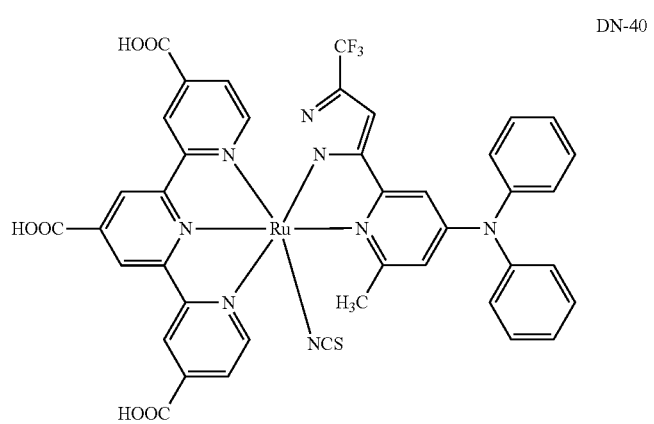
DN-40
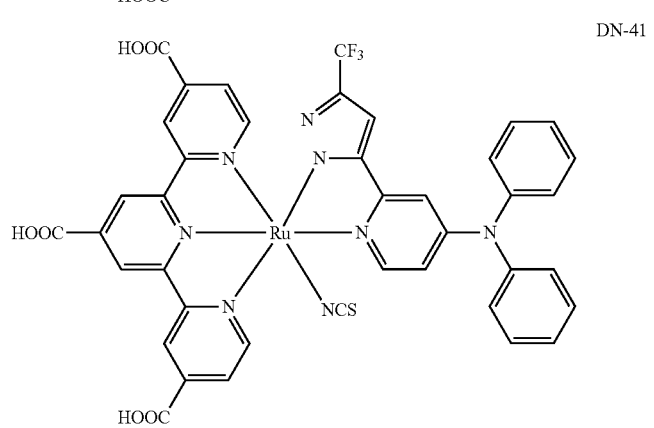
DN-41
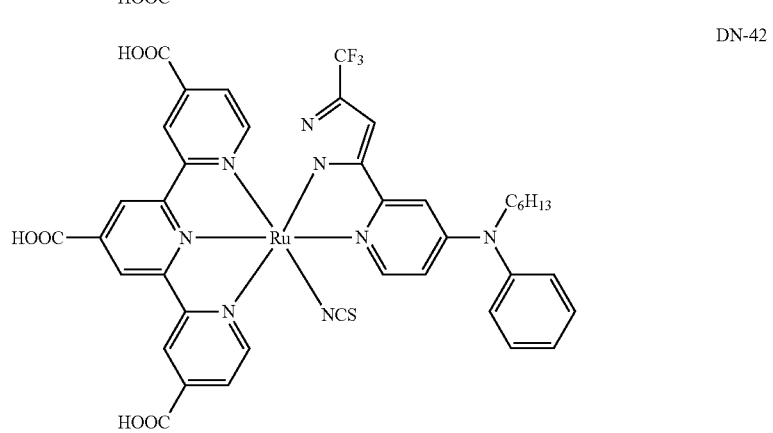
DN-42

DN-43
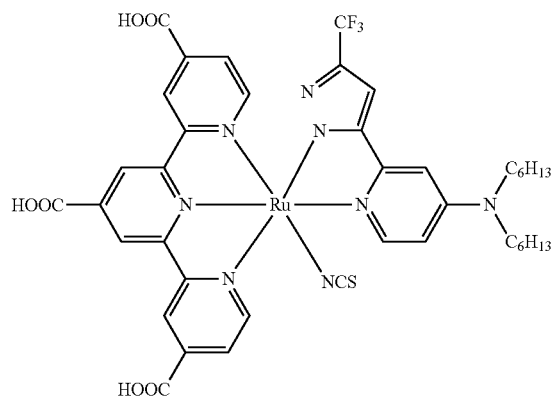
DN-44
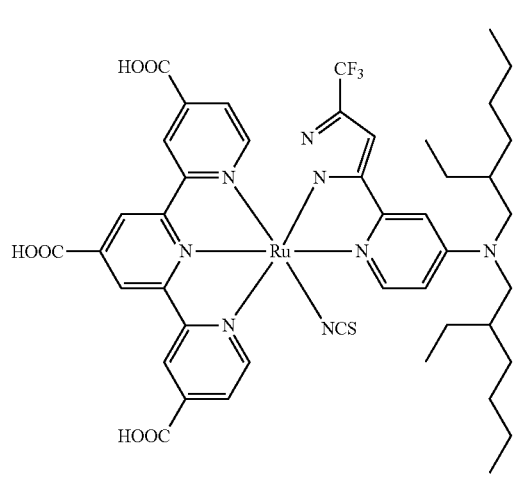
DN-45
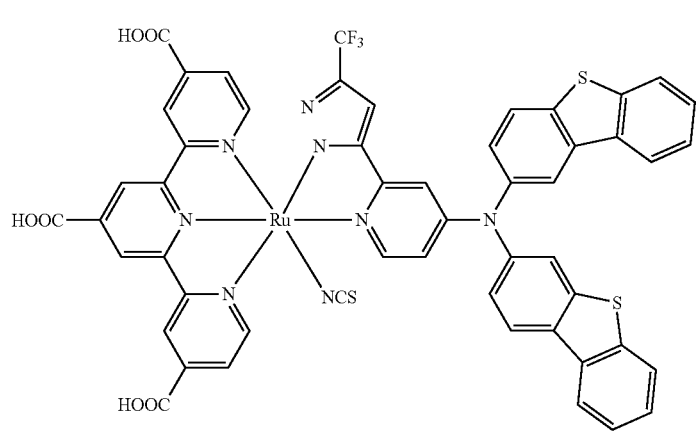

-continued
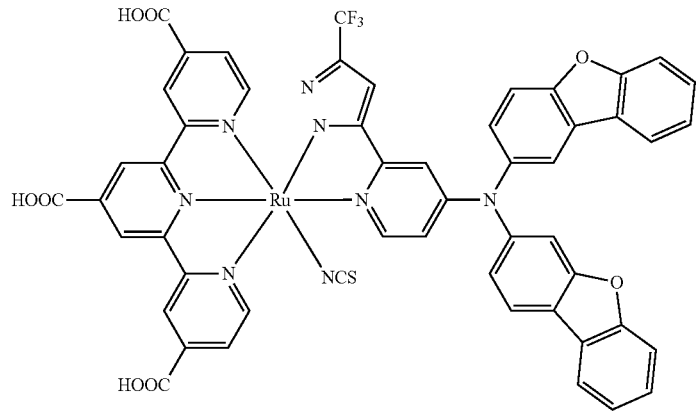
DN-46
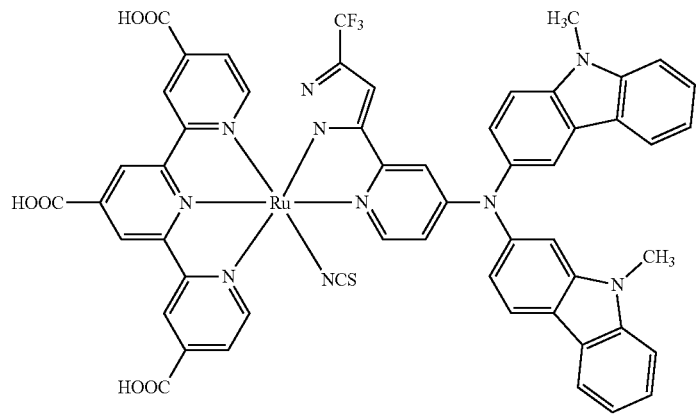
DN-47
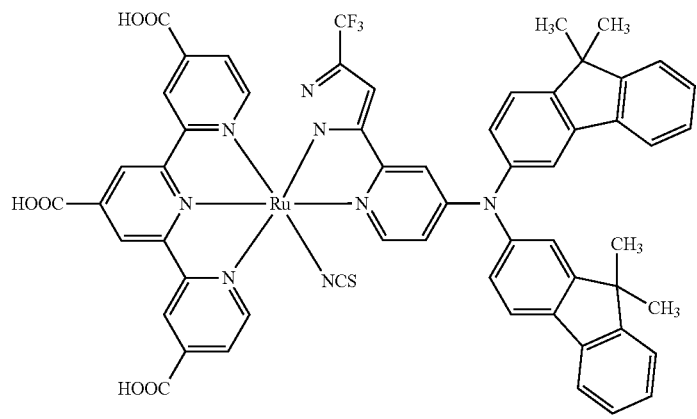
DN-48
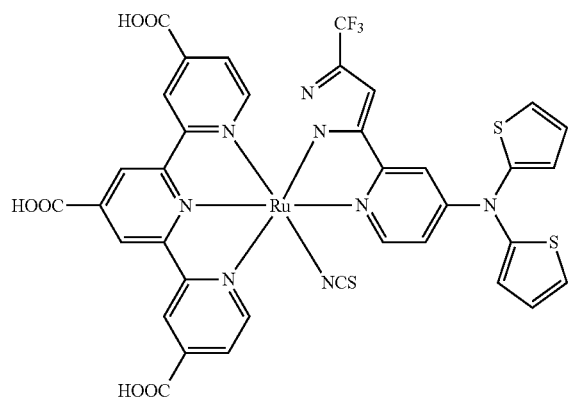
DN-49

-continued
DN-50
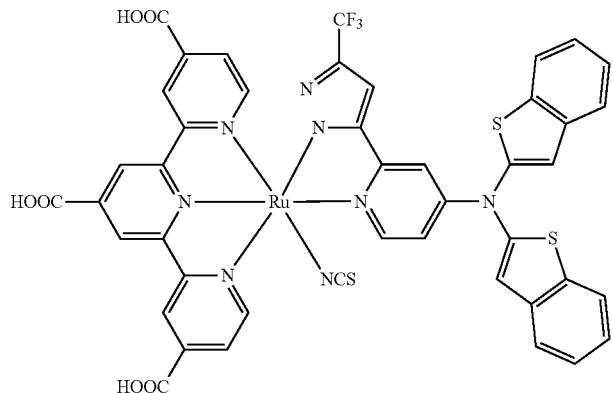
DN-51
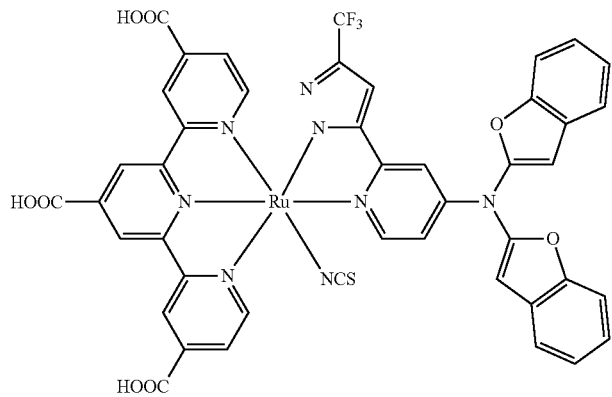
DN-52
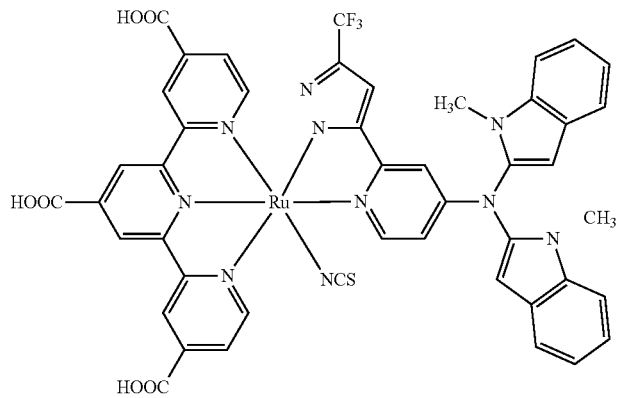
DA-1
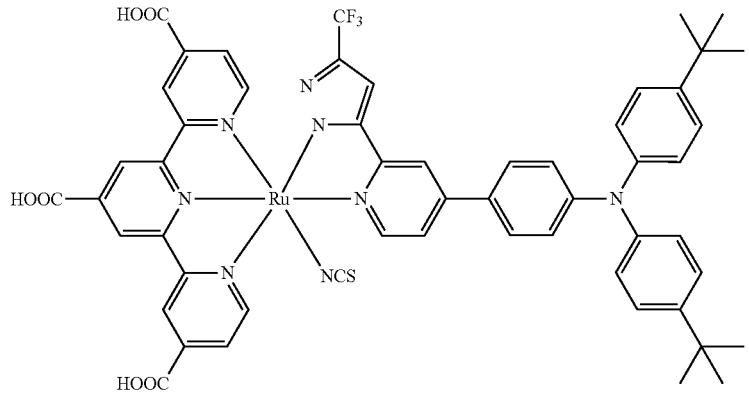

DA-2
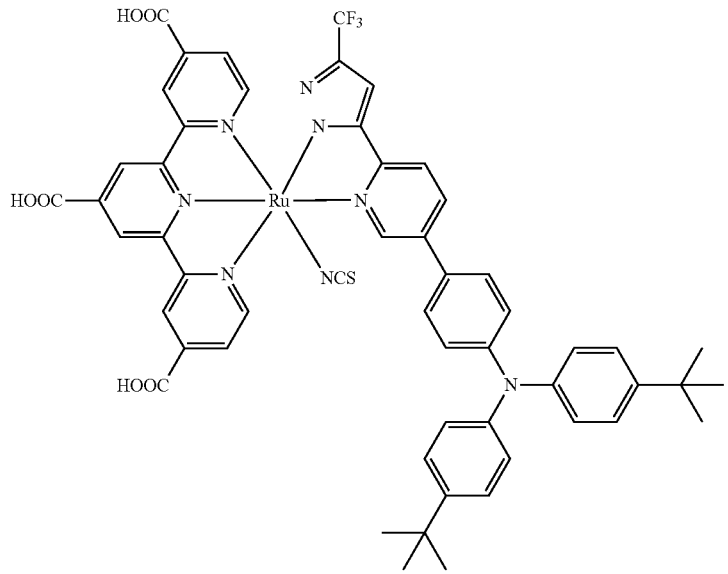
DA-3
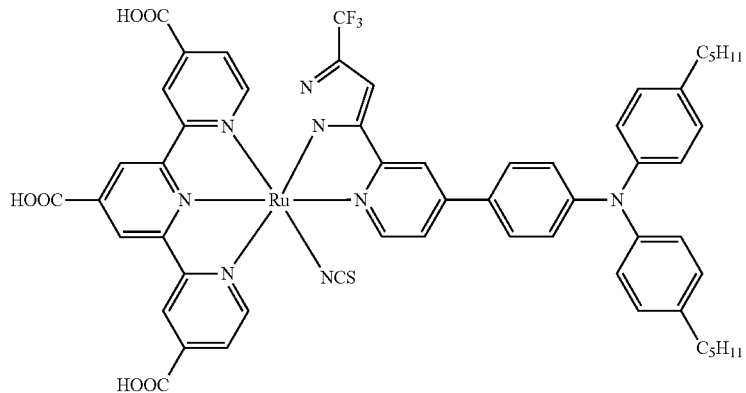
DA-4
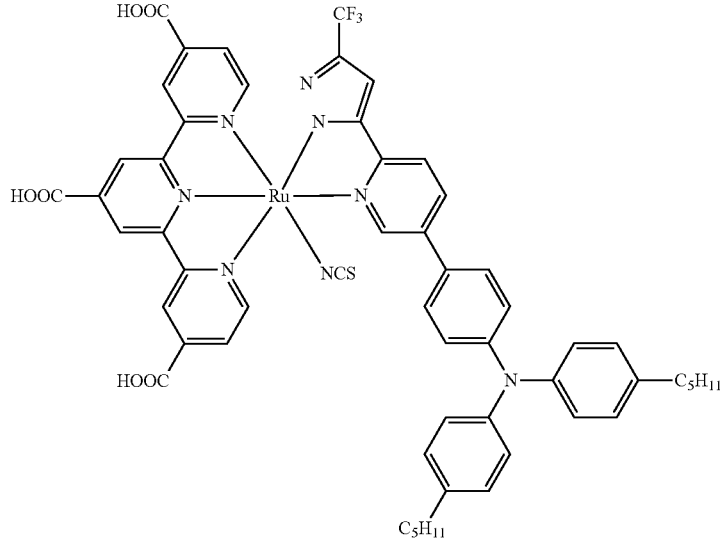

DA-5
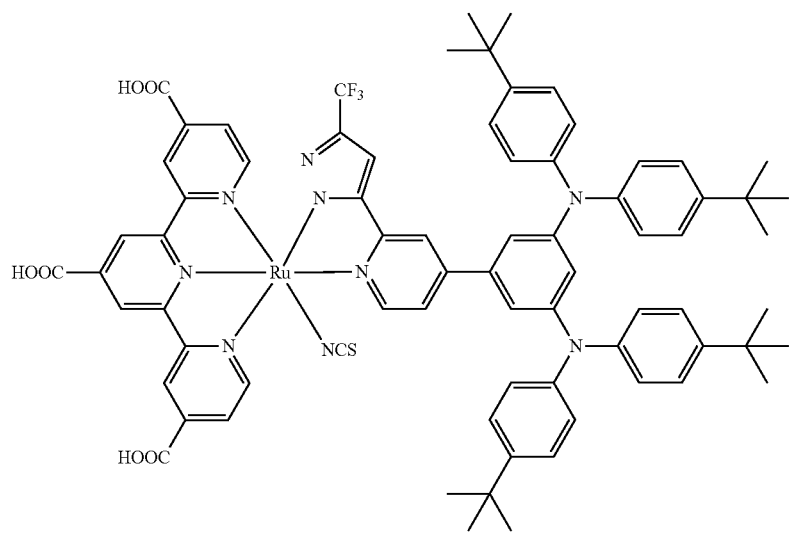
DA-6
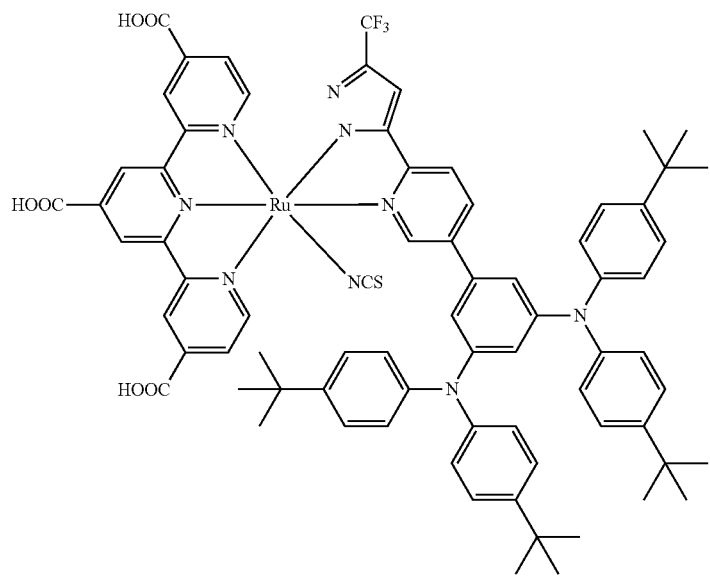
DA-7
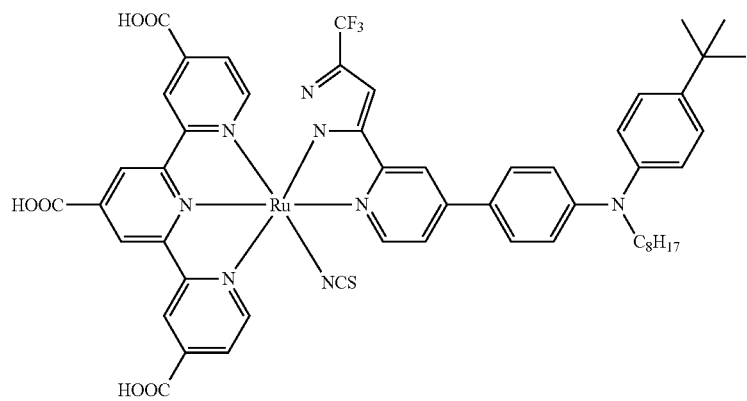

-continued
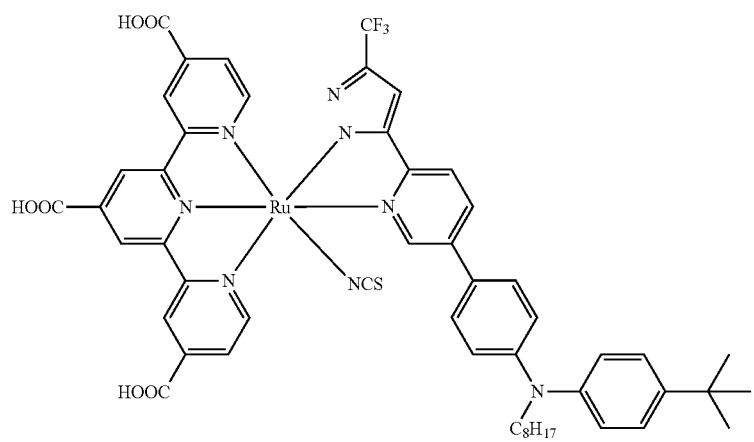
DA-8
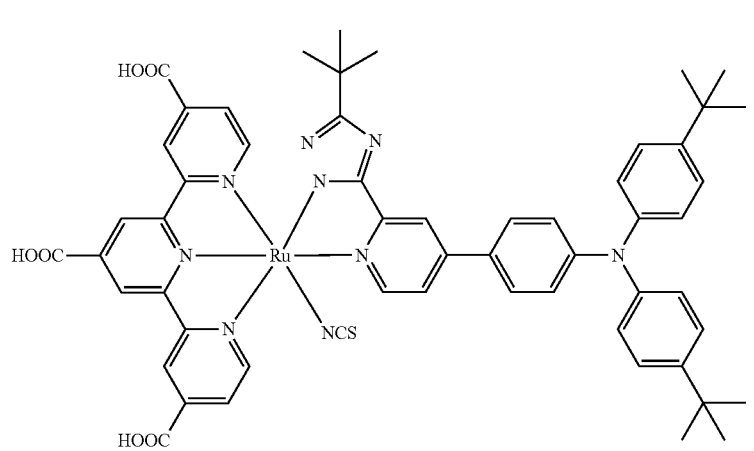
DA-9
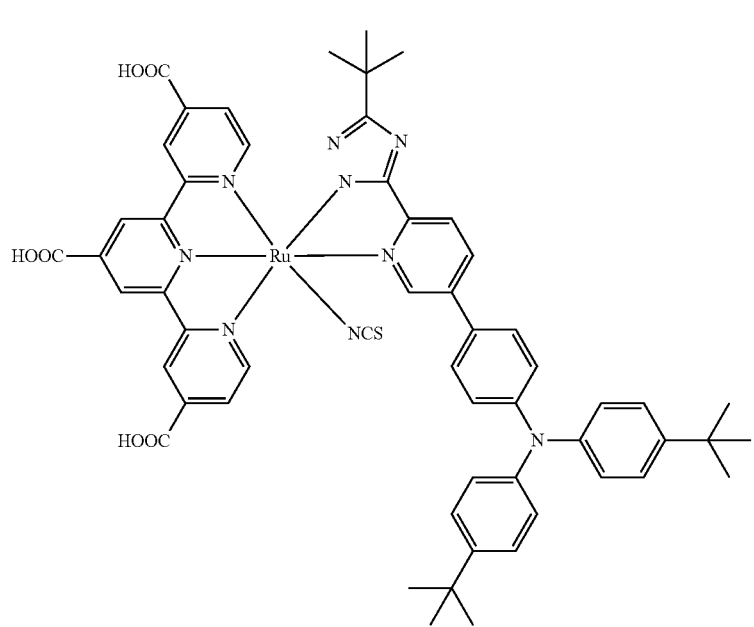
DA-10

-continued
DA-11
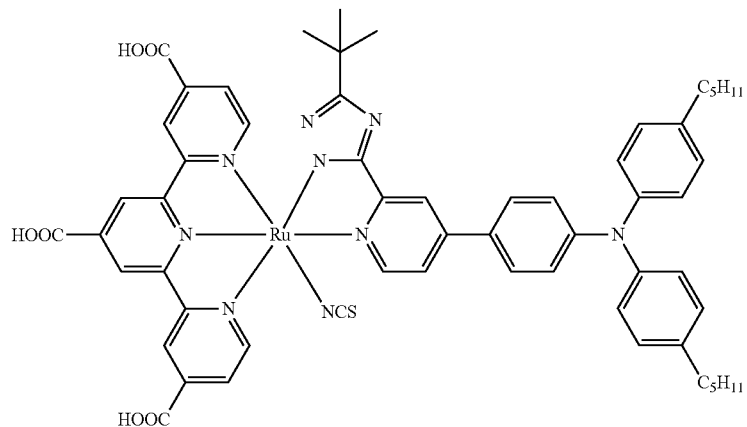
DA-12
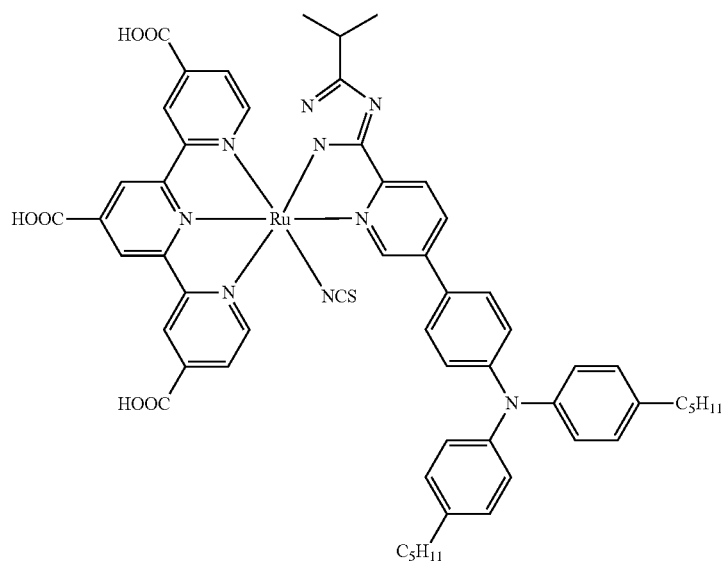
DA-13
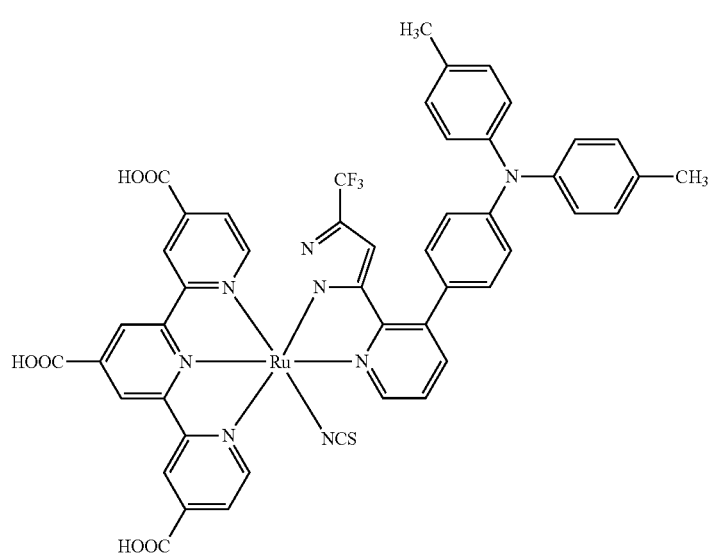

-continued
DA-14
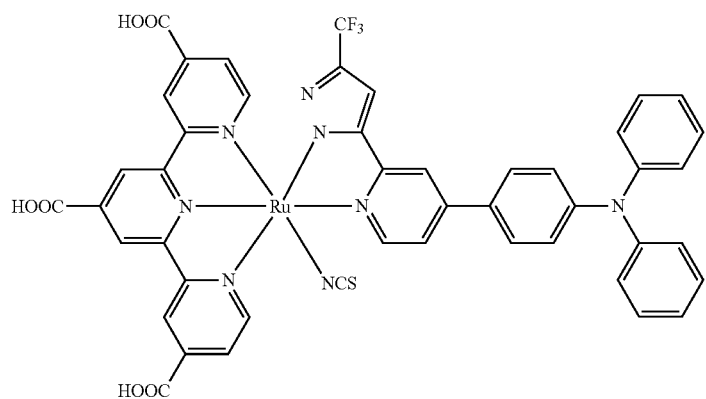
DA-15
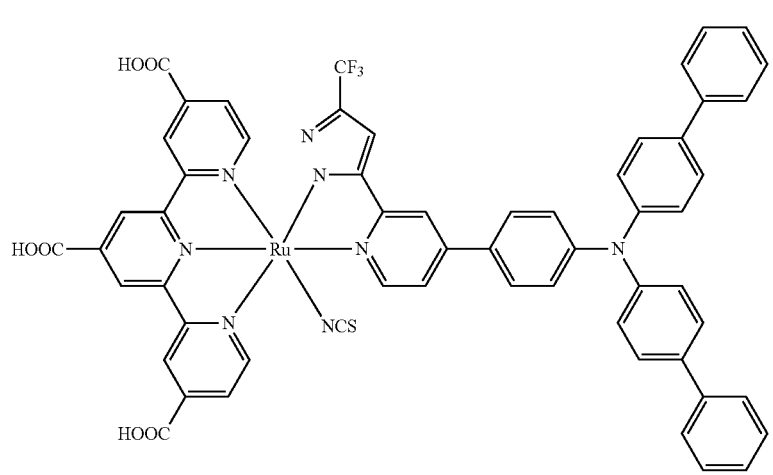
DA-16
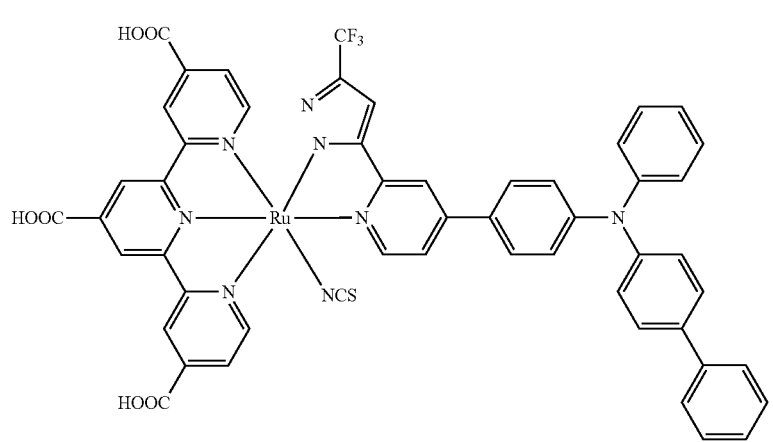

DA-17
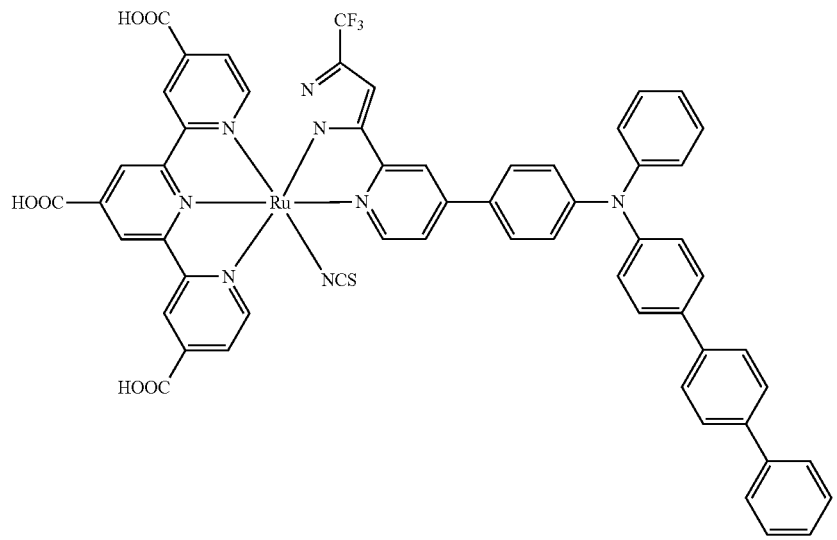
DA-18
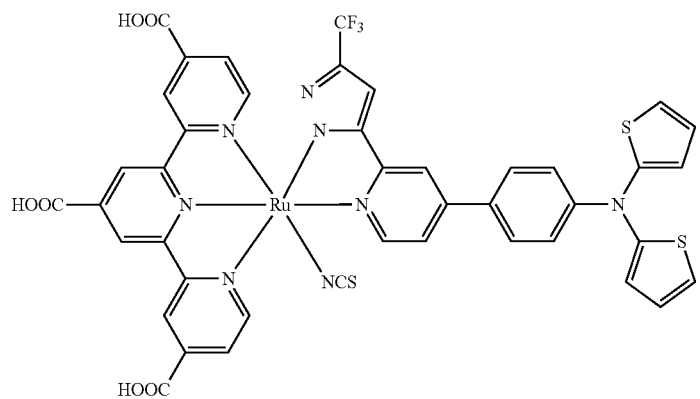
DA-19
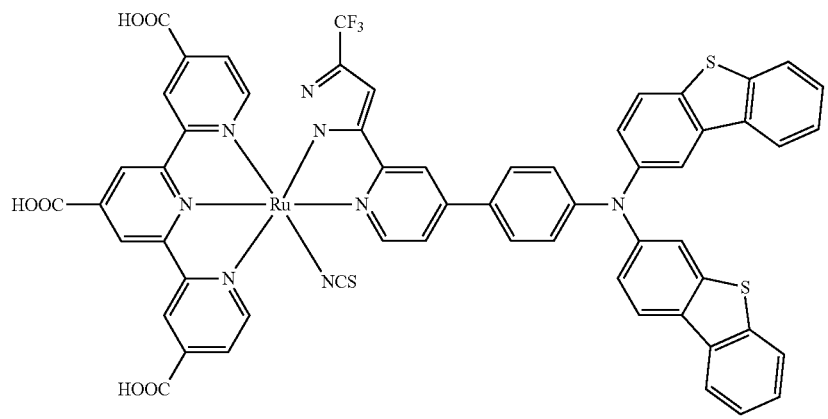

-continued
DA-20
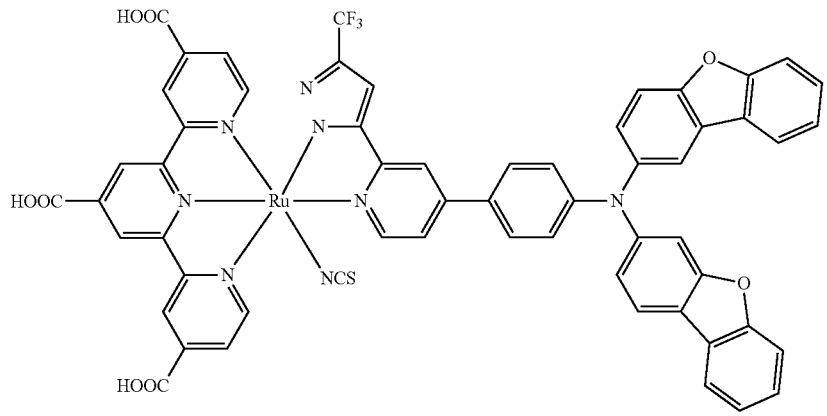
DA-21
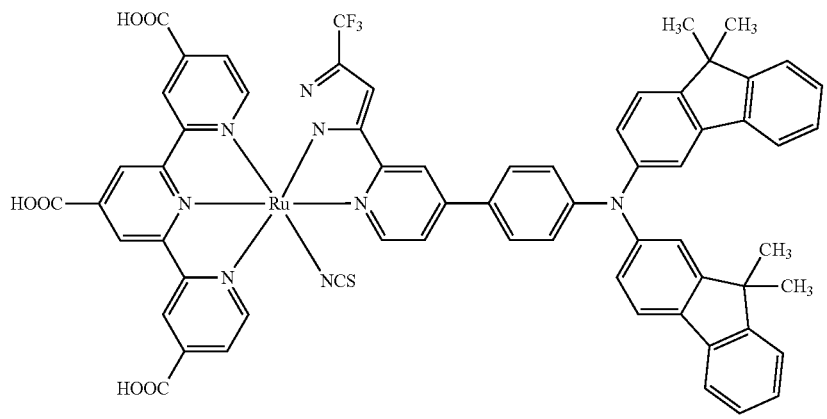
DA-22
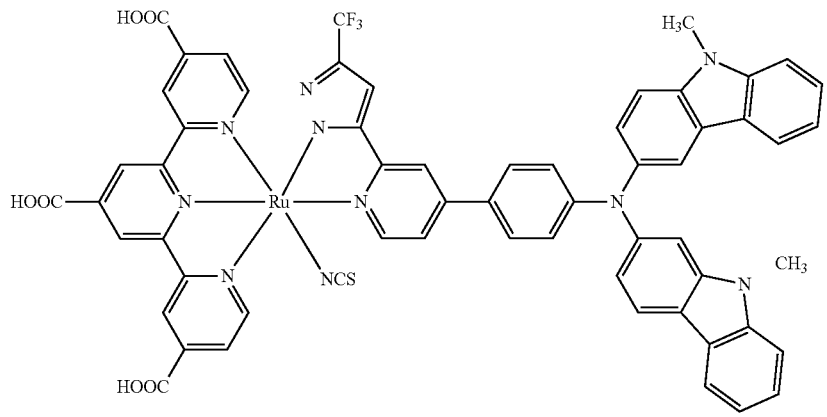
DE-1
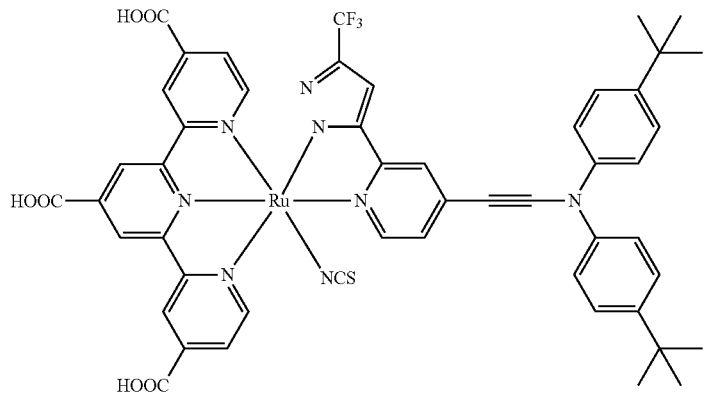

-continued
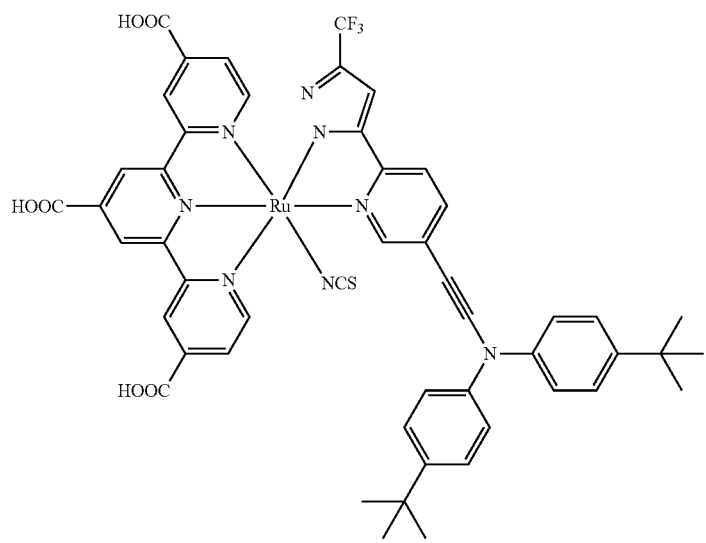
DE-2
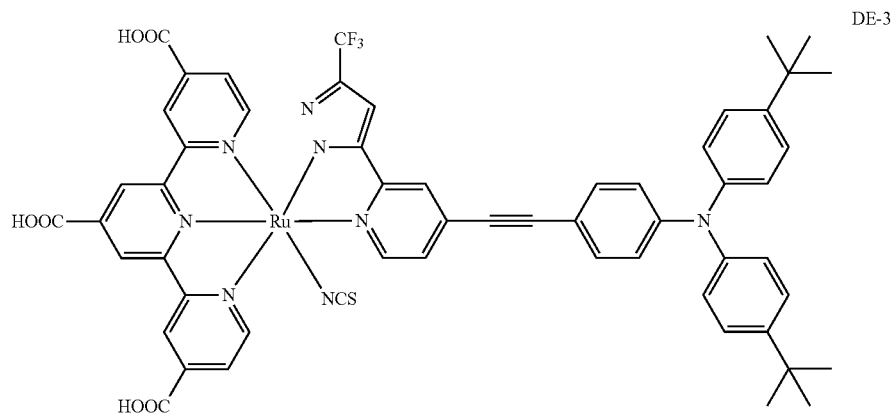
DE-3
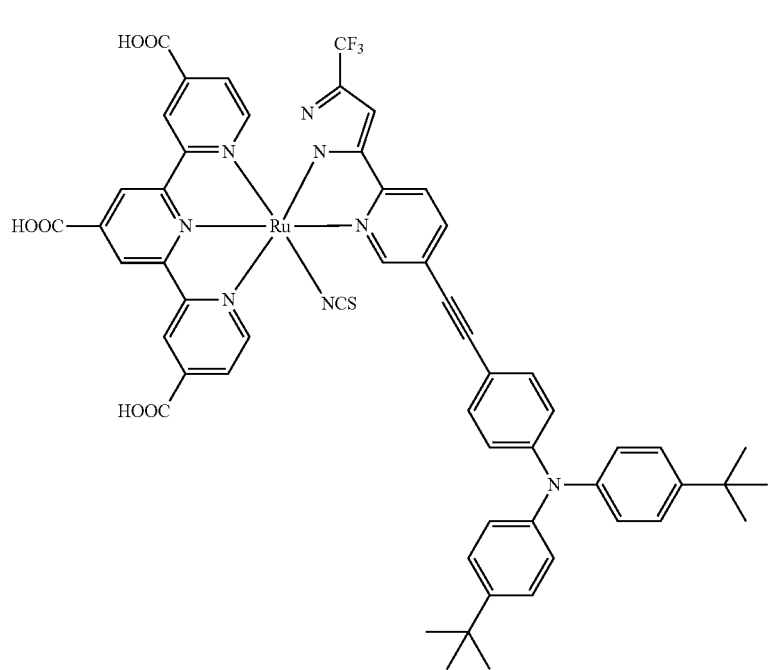
DE-4

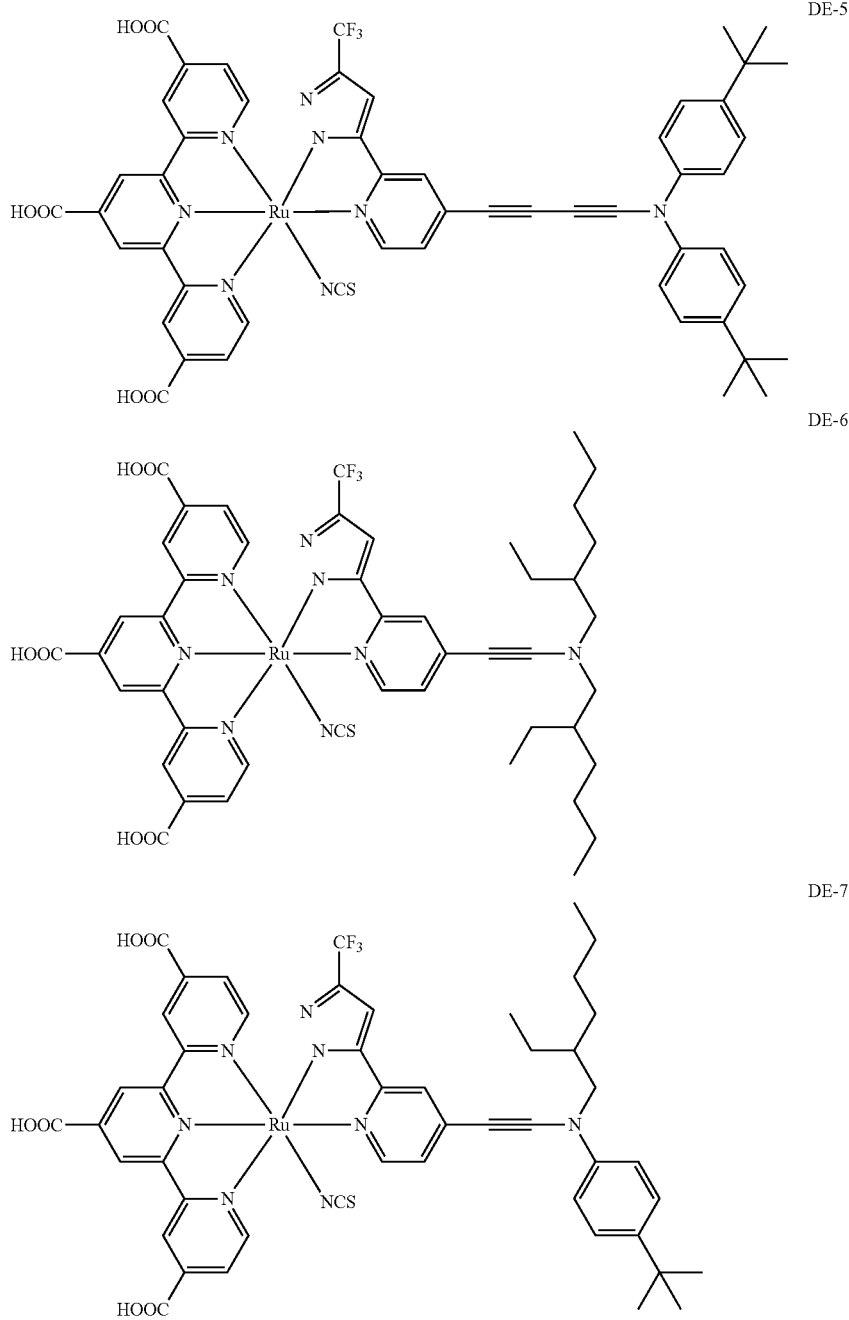

[Metal Complex Dye of Second Embodiment]

A metal complex dye of a second embodiment is represented by the following Formula (I).

$$M^1(LA)(LD)(Z^1) \cdot (CI)$$ Formula (I)

In Formula (I), $M^1$ represents a metal atom, and $Z^1$ represents a monodentate ligand. LA represents a tridentate ligand represented by the following Formula (AL-21). LD represents a bidentate ligand represented by the following Formula (DL-21). CI represents a counterion necessary for neutralizing the charge.

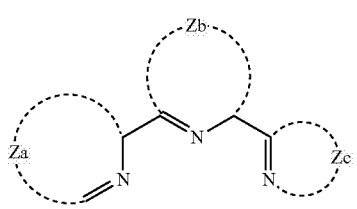

Formula (AL-1)

-continued

Formula (DL-1)

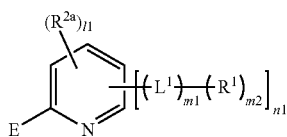

In Formula (AL-21), each of Za, Zb, and Zc represents a group of non-metal atoms necessary for forming a 5-membered ring or a 6-membered ring. Here, at least one of the rings formed by Za, Zb, and Zc has an acidic group.

In Formula (DL-21), m1 represents an integer of 0 to 3, m2 represents an integer of 1 to 4, and n1 represents an integer of 1 to 4. $L^1$ represents an arylene group, and $R^1$ represents a halogen atom, an alkyl group, an alkynyl group, an alkoxy group, an aryloxy group, an alkylthio group, or an arylthio group. E represents a group represented by the following Formula (E-21) or (E-22).

Formula (E-21)

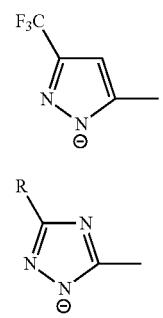

Formula (E-22)

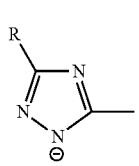

In Formula (E-22), R represents a hydrogen atom, an alkyl group, a phenyl group, or an aryloxy group.

—Metal Atom $M^1$—

$M^1$ represents a metal atom. $M^1$ is preferably a metal that can form a coordinate bond at 4 sites or 6 sites, and examples thereof include the elements of group 6 to group 12 in the long-form periodic table. $M^1$ is more preferably Ru, Fe, Os, Cu, W, Cr, Mo, Ni, Pd, Pt, Co, Ir, Rh, Re, Mn or Zn, particularly preferably Ru, Os, Zn, or Cu, and most preferably Ru.

—Ligand LA—

In the second embodiment, the ligand LA is represented by Formula (AL-21).

Each of Za, Zb, and Zc represents a group of non-metal atoms necessary for forming a 5-membered ring or a 6-membered ring.

The 5-membered ring or 6-membered ring formed by Za, Zb, and Zc may be substituted or unsubstituted or may be a monocyclic ring or a fused ring. When being in the form of a fused ring, the ring is preferably condensed with a benzene ring. The ring-constituting atom of Za, Zb, and Zc is preferably an atom selected from a carbon atom, a nitrogen atom, an oxygen atom, a sulfur atom, and a phosphorus atom, and more preferably selected from a carbon atom and a nitrogen atom. The ring-constituting atom may be substituted with a substituent including a hydrogen atom or a halogen atom.

The ring formed by Za, Zb, and Zc is more preferably an aromatic ring, that is, a nitrogen-containing aromatic ring.

When forming a 5-membered ring, Za, Zb, and Zc preferably form an imidazole ring, a benzimidazole ring, an oxazole ring, a thiazole ring, or a triazole ring. When forming a 6-membered ring, Za, Zb, and Zc preferably form a pyridine ring, a pyrimidine ring, a pyridazine ring, or a pyrazine ring. Among these, an imidazole ring, a benzimidazole ring, or a pyridine ring is more preferable.

At least one of the rings formed by Za, Zb, and Zc has an acidic group. The acidic group is preferably the acidic group Ac described in the first embodiment.

The ligand LA is preferably a ligand represented by the following Formula (AL-2).

Formula (AL-2)

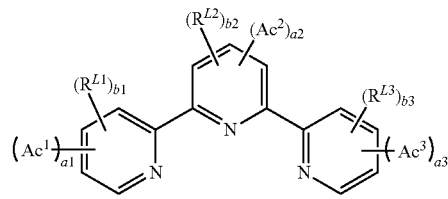

In Formula (AL-2), each of $Ac^1$, $Ac^2$, and $Ac^3$ independently represents an acidic group.

As the acidic group, those exemplified above as the acidic group Ac are preferable.

Each of $R^{L1}$, $R^{L2}$, and $R^{L3}$ independently represents a substituent. Examples of the substituent include the substituents T which will be described later. Each of $R^{L1}$, $R^{L2}$, and $R^{L3}$ preferably represents an alkyl group, an alkenyl group, an alkynyl group, an aryl group, a heteroaryl group, an alkoxy group, an amino group, an alkylamino group, or an arylamino group, more preferably represents an alkyl group, an aryl group, or a heteroaryl group, and particularly preferably represents a heteroaryl group.

Each of a1, a3, b1, and b3 independently represents an integer of 0 to 4, and each of a2, and b2 independently represents an integer of 0 to 3. Here, a1 to a3 do not represent 0 at the same time.

The ligand LA is preferably a ligand represented by the following Formula (AL-3).

Formula (AL-3)

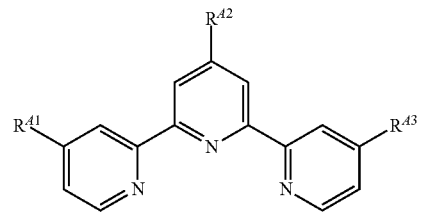

In Formula (AL-3), each of $R^{41}$, $R^{42}$, and $R^{43}$ independently represents a hydrogen atom, an alkyl group, an aryl group, a heteroaryl group, or an acidic group. Here, at least one of $R^{41}$, $R^{42}$, and $R^{43}$ represents an acidic group. The acidic group is preferably the acidic group Ac.

In the second embodiment, at least two out of $R^{41}$, $R^{42}$, and $R^{43}$ preferably represent an acidic group. More preferably, all three of $R^{41}$, $R^{42}$, and $R^{43}$ represent an acidic group. Particularly, all of $R^{41}$, $R^{42}$, and $R^{43}$ preferably represent a carboxy group or a salt thereof.

Specific examples of the ligand LA of the second embodiment will be shown below, but the present invention is not limited thereto.

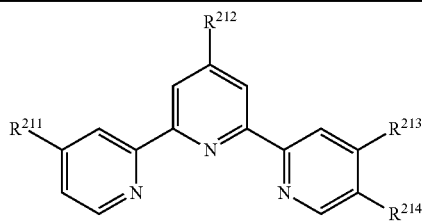

| | $R^{211}$ | $R^{212}$ | $R^{213}$ | $R^{214}$ |
|---|---|---|---|---|
| B-1-21 | —H | —CO$_2$H | —H | —H |
| B-1-22 | —CO$_2$H | —CO$_2$H | —CO$_2$H | —H |
| B-1-23 | —CO$_2$H | —CO$_2$H | —H | —H |
| B-1-24 | —CO$_2$H | —CO$_2$H | —H | 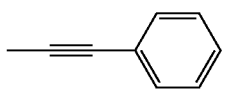 |
| B-1-25 | —CO$_2$H | —CO$_2$H | —H | 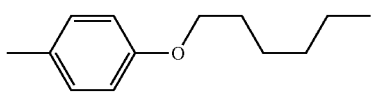 |
| B-1-26 | —H | —PO$_3$H$_2$ | —H | —H |
| B-1-27 | —H | —CO$_2$H | —CO$_2$H | —H |
| B-1-28 | —CO$_2^-$ | —H | —CO$_2^-$ | —H |

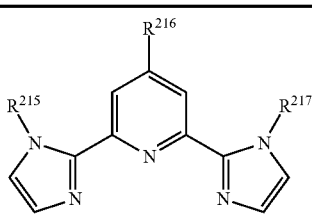

| | $R^{215}$ | $R^{216}$ | $R^{217}$ |
|---|---|---|---|
| B-2-21 | —H | —CO$_2$H | —H |
| B-2-22 | —$^nC_6H_{13}$ | —CO$_2$H | —H |
| B-2-23 | —$^nC_6H_{13}$ | —CO$_2$H | —$^nC_6H_{13}$ |
| B-2-24 | —H | —PO$_3$H$_2$ | —H |

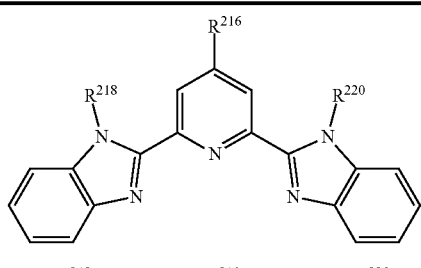

| | $R^{218}$ | $R^{219}$ | $R^{220}$ |
|---|---|---|---|
| B-3-21 | —H | —CO$_2$H | —H |
| B-3-22 | —$^nC_6H_{13}$ | —CO$_2$H | —H |
| B-3-23 | —$^nC_6H_{13}$ | —CO$_2$H | —$^nC_6H_{13}$ |
| B-3-24 | —H | —PO$_3$H$_2$ | —H |

—Ligand LD—

In the second embodiment, the ligand LD is represented by Formula (DL-21).

$L^1$ represents an arylene group. Examples of the arylene group include phenylene and naphthylene, and among these, phenylene is preferable. Examples of the phenylene include 1,4-phenylene, 1,3-phenylene, and 1,2-phenylene, and among these, 1,4-phenylene is preferable.

The arylene group may have a substituent. Examples of the substituent include the substituents T which will be described later. Among the substituents, a halogen atom, an alkyl group, an aryl group, a heterocyclic group, an alkoxy group, and an alkylthio group are preferable.

The substituent and $R^1$ may form a ring by being bonded to each other. Furthermore, when the arylene group further has a plurality of substituents, the substituents may form a ring by being bonded to each other.

$R^1$ represents a halogen atom, an alkyl group, an alkynyl group, an alkoxy group, an aryloxy group, an alkylthio group, or an arylthio group. Among these, a halogen atom, an alkyl group, an alkynyl group, an alkoxy group, and an alkylthio group are preferable.

Examples of the halogen atom include a fluorine atom, a chlorine atom, a bromine atom, and an iodine atom. Among these, a fluorine atom, a chlorine atom, and a bromine atom are preferable, and a fluorine atom is more preferable.

The alkyl group is a linear or branched alkyl group. The alkyl group preferably has 1 to 20 carbon atoms, and more preferably has 1 to 18 carbon atoms. Examples of the alkyl group include methyl, ethyl, isopropyl, n-butyl, t-butyl, n-hexyl, n-octyl, 2-ethylhexyl, n-dodecyl, and n-hexadecyl.

The alkenyl group preferably has 2 to 20 carbon atoms, and more preferably has 2 to 12 carbon atoms. Examples of the alkenyl group include vinyl, allyl, and oleyl.

The alkynyl group preferably has 2 to 20 carbon atoms, and more preferably has 2 to 12 carbon atoms. Examples of the alkynyl group include ethynyl, heptan-1-yl, and 2-phenylethynyl.

The alkynyl group is preferably a group represented by the following Formula (SA).

 Formula (SA)

In Formula (SA), $R^x$ represents a hydrogen atom, an alkyl group, an aryl group, or a heteroaryl group.

The alkyl group represented by $R^x$ is preferably an alkyl group represented by $R^1$ in Formula (DL-21).

The aryl group represented by $R^x$ is preferably an aryl group having 6 to 20 carbon atoms, and examples of the aryl group include phenyl and naphthyl. The aryl group is preferably a phenyl group which may have a substituent.

The heteroaryl group represented by $R^x$ is preferably a heteroaryl group as a 5-membered ring or a 6-membered ring. The heteroaryl ring in the heteroaryl group may be fused with an aryl ring, an alicyclic ring, or a heterocyclic ring and may have a substituent. Examples of the substituent include the substituents T which will be described later.

The ring-constituting heteroatom of the heteroaryl ring is preferably an oxygen atom, a sulfur atom, a nitrogen atom, or a selenium atom.

Examples of the heteroaryl ring in the heteroaryl group include a furan ring, a thiophene ring, and a pyrrole ring, and among these, a thiophene ring is preferable. Furthermore, a ring formed as a result of fusion of the thiophene ring with a benzene ring or a thiophene ring is preferable.

The alkoxy group is a linear or branched alkoxy group. The alkoxy group preferably has 1 to 20 carbon atoms, and more preferably has 1 to 18 carbon atoms. Examples of the alkoxy group include methoxy, ethoxy, isopropyloxy, n-butyloxy, s-butyloxy, n-hexyloxy, n-octyloxy, 2-ethylhexyloxy, n-dodecyloxy, and n-hexadecyloxy.

The alkylthio group is a linear or branched alkylthio group. The alkylthio group preferably has 1 to 20 carbon atoms, and more preferably has 1 to 18 carbon atoms. Examples of the alkylthio group include methylthio, ethylthio, isopropylthio, n-butylthio, t-butylthio, n-hexylthio, n-octylthio, 2-ethylhexylthio, n-dodecylthio, and n-hexadecylthio.

The aryloxy group preferably has 6 to 20 carbon atoms, and more preferably has 6 to 18 carbon atoms. Examples of the aryloxy group include phenoxy, p-methylphenoxy, p-methoxyphenoxy, m-chlorophenoxy, and naphthoxy.

The arylthio group preferably has 6 to 20 carbon atoms, and more preferably has 6 to 18 carbon atoms. Examples of the arylthio group include phenylthio, p-methylphenylthio, p-methoxyphenylthio, m-chlorophenylthio, and naphthylthio.

Each of these groups may be substituted with a substituent. Examples of the substituent include the substituents T which will be described later. Among the substituents, a halogen atom, an alkyl group, an alkenyl group, an alkynyl group, an aryl group, a heterocyclic group, an alkoxy group, and an alkylthio group are preferable.

In Formula (DL-21), m1 represents an integer of 0 to 3. m1 is preferably 0 or 1, and more preferably 0.

m2 represents an integer of 1 to 4. When m2 is equal to or greater than 2, a plurality of $R^1$s may be the same as or different from each other. Furthermore, the plurality of $R^1$s may form a ring by being bonded to each other.

m2 is preferably an integer of 1 to 3. m2 is more preferably 1 or 2, and particularly preferably 1.

n1 represents an integer of 1 to 4. n1 is preferably an integer of 1 to 3, more preferably 1 or 2, and particularly preferably 1.

E represents a group represented by Formula (E-21) or (E-22).

In Formula (E-22), R represents a hydrogen atom, an alkyl group, a phenyl group, or an aryloxy group, and these may have a substituent. Examples of the substituent include the substituents T which will be described later. As the substituent, an electron donating group is preferable, and an alkyl group, an aryl group, an alkoxy group, an aryloxy group, an alkylthio group, and an arylthio group are more preferable.

The alkyl group represented by R is a linear or branched alkyl group. The alkyl group preferably has 1 to 20 carbon atoms, more preferably has 1 to 16 carbon atoms, and even more preferably has 1 to 12 carbon atoms. Examples of the alkyl group include methyl, ethyl, propyl, isopropyl, butyl, t-butyl, hexyl, octyl, 2-ethylhexyl, and dodecyl.

The aryloxy group represented by R preferably has 6 to 20 carbon atoms, more preferably has 6 to 18 carbon atoms, and even more preferably has 6 to 12 carbon atoms. Examples of the aryloxy group include phenoxy, p-methylphenoxy, p-methoxyphenoxy, and p-fluorophenoxy.

Among the groups represented by Formulae (E-21) and (E-22), a group represented by Formula (E-21) is preferable as E.

The ligand LD is preferably a ligand represented by any of the following Formulae (DL-22) to (DL-24). Particularly, the ligand LD is preferably a ligand represented by Formula (DL-23) or (DL-24).

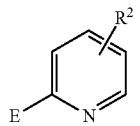

Formula (DL-22)

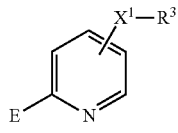

Formula (DL-23)

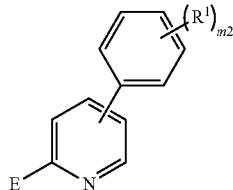

Formula (DL-24)

In Formulae (DL-22) to (DL-24), E, $R^1$, and m2 have the same definition as that of E, $R^1$, and m2 in Formula (DL-21), and a preferred range thereof is also the same. $X^1$ represents —C(Ra)(Rb)—, an ethynylene group, —S—, or —O—. Herein, each of Ra and Rb independently represents a hydrogen atom or an alkyl group. $R^2$ represents a halogen atom. When $X^1$ represents —C(Ra)(Rb)—, $R^3$ represents a hydrogen atom or an alkyl group; when $X^1$ represents an ethynylene group, $R^3$ represents a hydrogen atom, an alkyl group, an aryl group, or a heteroaryl group; and when $X^1$ represents —S— or —O—, $R^3$ represents an alkyl group or an aryl group. When m2 is equal to or greater than 2, a plurality of $R^1$s may be the same as or different from each other.

The alkyl group represented by each of Ra and Rb is a linear or branched alkyl group. The alkyl group preferably has 1 to 20 carbon atoms, more preferably has 1 to 18 carbon atoms, and even more preferably has 1 to 12 carbon atoms.

At least one of Ra and Rb preferably represents a hydrogen atom. Furthermore, both of Ra and Rb preferably represent a hydrogen atom or an alkyl group.

$X^1$ is preferably —C(Ra)(Rb)—, an ethynylene group, or —O—.

The halogen atom represented by $R^2$ is preferably a fluorine atom, a chlorine atom, or a bromine atom, more preferably a fluorine atom or a chlorine atom, and even more preferably a fluorine atom.

The alkyl group represented by $R^3$ is preferably an alkyl group having 5 or more carbon atoms, and more preferably an alkyl group having 5 to 20 carbon atoms. Furthermore, $R^3$ is preferably an unsubstituted alkyl group, and more preferably a linear alkyl group.

The aryl group and heteroaryl group represented by $R^3$ have the same definition as that of the aryl group and heteroaryl group represented by $R^x$, and a preferred range thereof is also the same.

Among the ligands represented by Formula (DL-23) or (DL-24), a ligand represented by any of the following Formulae (DL-23a) to (DL-23d) or a ligand represented by any of the following Formulae (DL-24a) to (DL-24c) is more preferable.

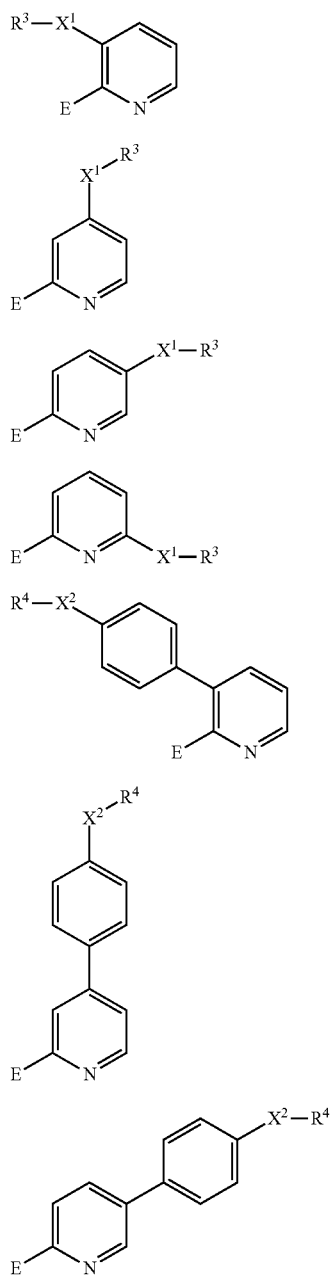

Formula (DL-23a)

Formula (DL-23b)

Formula (DL-23c)

Formula (DL-23d)

Formula (DL-24a)

Formula (DL-24b)

Formula (DL-24c)

In Formulae (DL-23a) to (DL-23d) and (DL-24a) to (DL-24c), E has the same definition as that of E in Formula (DL-21), and a preferred range thereof is also the same. $X^1$ and $R^3$ have the same definition as that of $X^1$ and $R^3$ in Formula (DL-23). $X^2$ represents —C(Ra)(Rb)—, an ethynylene group, —S—, or —O—. Herein, each of Ra and Rb independently represents a hydrogen atom or an alkyl group. When $X^2$ represents —C(Ra)(Rb)—, $R^4$ represents a hydrogen atom or an alkyl group; when $X^2$ represents an ethynylene group, $R^4$ represents a hydrogen atom, an alkyl group, an aryl group, or a heteroaryl group; and when $X^2$ represents —S— or —O—, $R^4$ represents an alkyl group or an aryl group.

—C(Ra)(Rb)—, an ethynylene group, —S—, and —O— represented by $X^2$ have the same definition as that of —C(Ra)(Rb)—, an ethynylene group, —S—, and —O— represented by $X^1$, and a preferred range thereof is also the same.

$X^2$ is preferably —C(Ra)(Rb)—, an ethynylene group, or —O—.

$R^4$ has the same definition as that of $R^3$, and a preferred range thereof is also the same.

Specific examples of the ligand LD of the second embodiment will be shown below, but the present invention is not limited thereto.

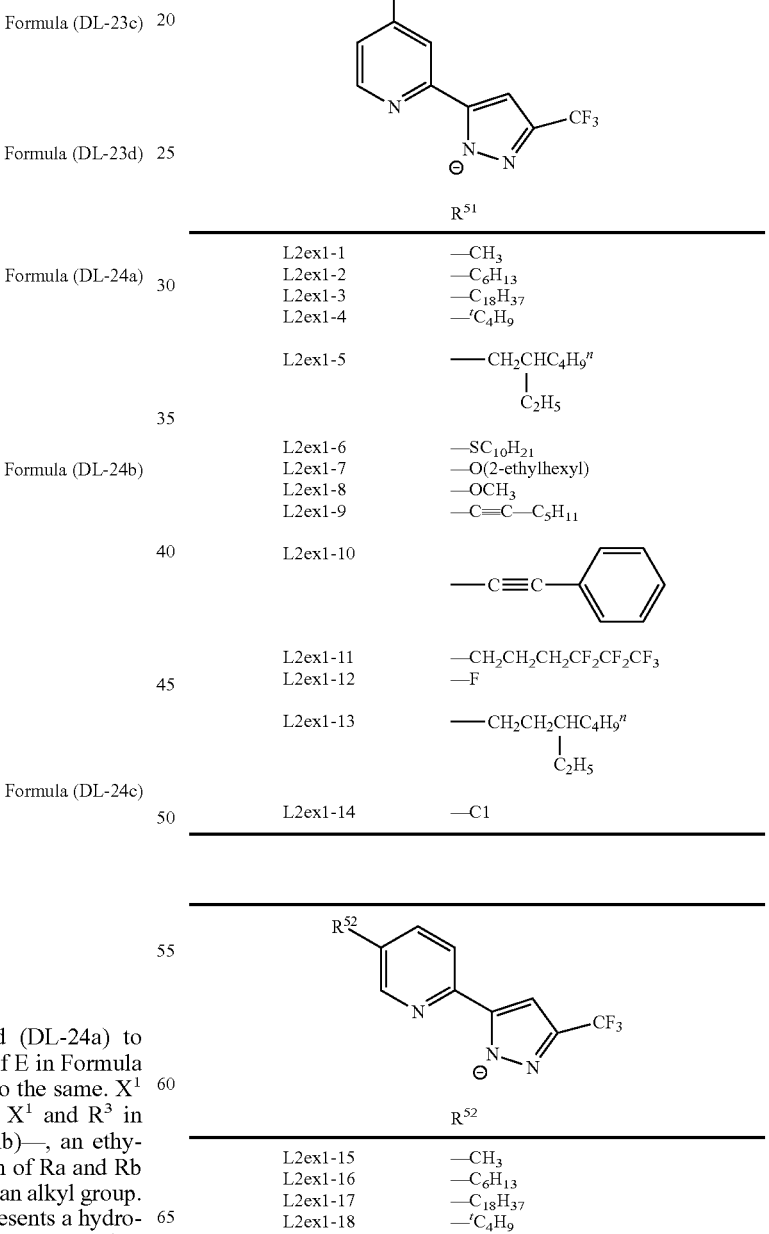

| | $R^{51}$ |
|---|---|
| L2ex1-1 | —CH$_3$ |
| L2ex1-2 | —C$_6$H$_{13}$ |
| L2ex1-3 | —C$_{18}$H$_{37}$ |
| L2ex1-4 | —$^t$C$_4$H$_9$ |
| L2ex1-5 | —CH$_2$CHC$_4$H$_9{}^n$ \| C$_2$H$_5$ |
| L2ex1-6 | —SC$_{10}$H$_{21}$ |
| L2ex1-7 | —O(2-ethylhexyl) |
| L2ex1-8 | —OCH$_3$ |
| L2ex1-9 | —C≡C—C$_5$H$_{11}$ |
| L2ex1-10 | —C≡C—Ph |
| L2ex1-11 | —CH$_2$CH$_2$CH$_2$CF$_2$CF$_2$CF$_3$ |
| L2ex1-12 | —F |
| L2ex1-13 | —CH$_2$CH$_2$CHC$_4$H$_9{}^n$ \| C$_2$H$_5$ |
| L2ex1-14 | —Cl |

| | $R^{52}$ |
|---|---|
| L2ex1-15 | —CH$_3$ |
| L2ex1-16 | —C$_6$H$_{13}$ |
| L2ex1-17 | —C$_{18}$H$_{37}$ |
| L2ex1-18 | —$^t$C$_4$H$_9$ |

[Structure: pyridine (with R52 at 5-position) linked to pyrazole-CF3 with N⊖]

R52

| | |
|---|---|
| L2ex1-19 | —CH₂CH(C₂H₅)C₄H₉ⁿ |
| L2ex1-20 | —SC₁₀H₂₁ |
| L2ex1-21 | —OC₄H₉ |
| L2ex1-22 | —OCH₃ |
| L2ex1-23 | —C≡C—C₅H₁₁ |
| L2ex1-24 | —C≡C—C₆H₅ (phenyl) |
| L2ex1-25 | —CH₂CH₂CH₂CF₂CF₂CF₃ |
| L2ex1-26 | —F |
| L2ex1-27 | —CH₂CH₂CH(C₂H₅)C₄H₉ⁿ |
| L2ex1-28 | —Cl |

[Structure: pyridine (with R53 at 6-position) linked to pyrazole-CF3 with N⊖]

R53

| | |
|---|---|
| L2ex1-29 | —CH₃ |
| L2ex1-30 | —C₆H₁₃ |
| L2ex1-31 | —C₁₈H₃₇ |
| L2ex1-32 | —ᵗC₄H₉ |
| L2ex1-33 | —CH₂CH(C₂H₅)C₄H₉ⁿ |
| L2ex1-34 | —SC₁₀H₂₁ |
| L2ex1-35 | —OC₄H₉ |
| L2ex1-36 | —OCH₃ |
| L2ex1-37 | —C≡C—C₅H₁₁ |
| L2ex1-38 | —C≡C—C₆H₅ |
| L2ex1-39 | —CH₂CH₂CH₂CF₂CF₂CF₃ |
| L2ex1-40 | —F |
| L2ex1-41 | —CH₂CH₂CH(C₂H₅)C₄H₉ⁿ |
| L2ex1-42 | —Cl |

[Structure: pyridine (with R54 at 3-position) linked to pyrazole-CF3 with N⊖]

R54

| | |
|---|---|
| L2ex1-43 | —CH₃ |
| L2ex1-44 | —C₆H₁₃ |
| L2ex1-45 | —C₁₈H₃₇ |
| L2ex1-46 | —ᵗC₄H₉ |
| L2ex1-47 | —CH₂CH(C₂H₅)C₄H₉ⁿ |
| L2ex1-48 | —SC₁₀H₂₁ |
| L2ex1-49 | —OC₄H₉ |
| L2ex1-50 | —OCH₃ |
| L2ex1-51 | —C≡C—C₅H₁₁ |
| L2ex1-52 | —C≡C—C₆H₅ |
| L2ex1-53 | —CH₂CH₂CH₂CF₂CF₂CF₃ |
| L2ex1-54 | —F |
| L2ex1-55 | —CH₂CH₂CH(C₂H₅)C₄H₉ⁿ |
| L2ex1-56 | —Cl |

L2ex1-57: [Structure: 4-OCH₃, 3,5-dimethyl pyridine linked to pyrazole-CF3 with N⊖]

L2ex1-58: [Structure: 3-OC₁₀H₂₁ pyridine linked to pyrazole-CF3 with N⊖]

L2ex1-59: [Structure: 3,5-dimethyl pyridine linked to pyrazole-CF3 with N⊖]

| | R51 |
|---|---|
| | 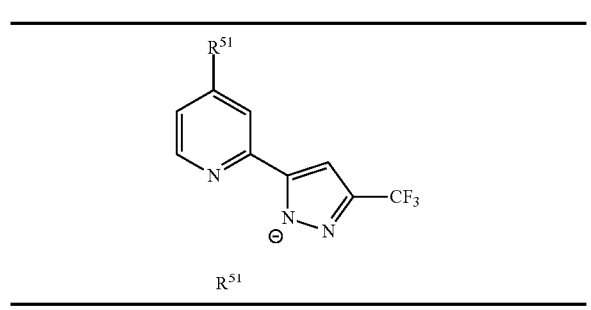 |
| | R51 |
| L2ex1a-1 |  |
| L2ex1a-2 | 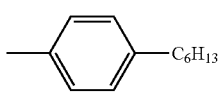 |
| L2ex1a-3 | 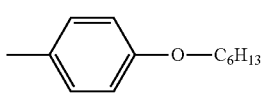 |
| L2ex1a-4 | 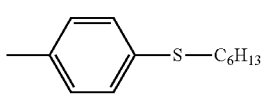 |
| L2ex1a-5 | 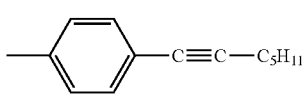 |
| L2ex1a-6 | 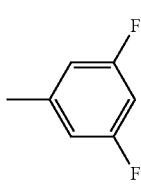 |
| | 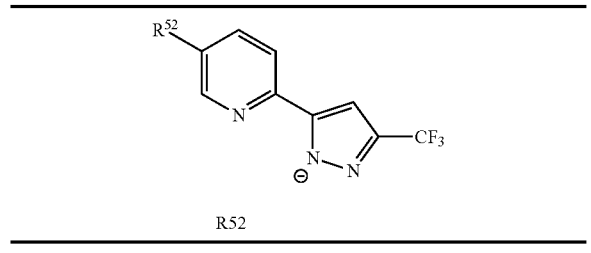 |
|---|---|
| | R52 |
| L2ex1b-1 |  |
| L2ex1b-2 | 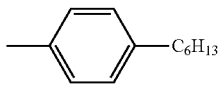 |
| L2ex1b-3 | 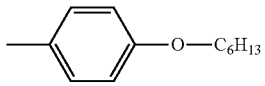 |
| L2ex1b-4 | 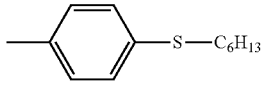 |
-continued
| | 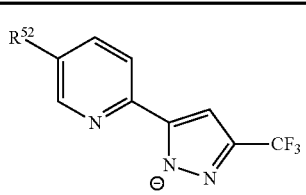 |
|---|---|
| | R52 |
| L2ex1b-5 | 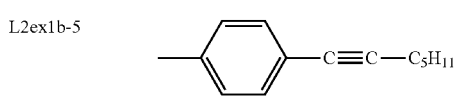 |
| L2ex1b-6 | 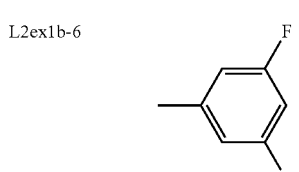 |
| | 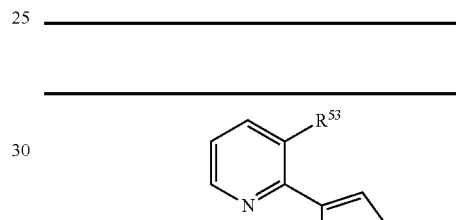 |
|---|---|
| | R53 |
| L2ex1c-1 | 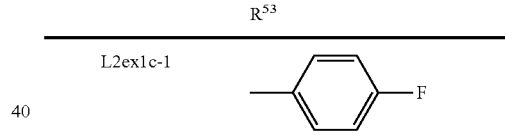 |
| L2ex1c-2 | 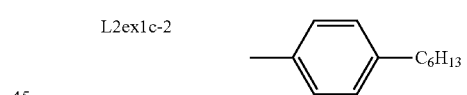 |
| L2ex1c-3 | 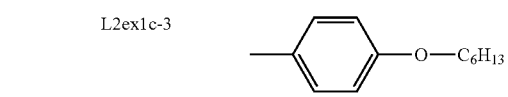 |
| L2ex1c-4 | 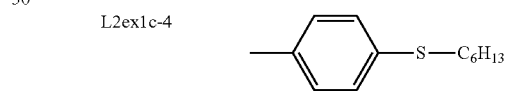 |
| L2ex1c-5 | 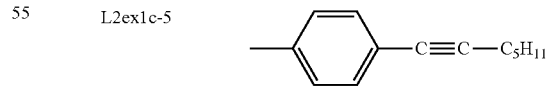 |
| L2ex1c-6 | 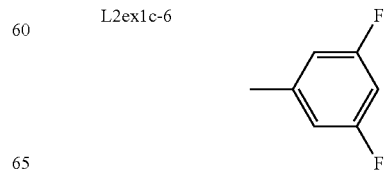 |

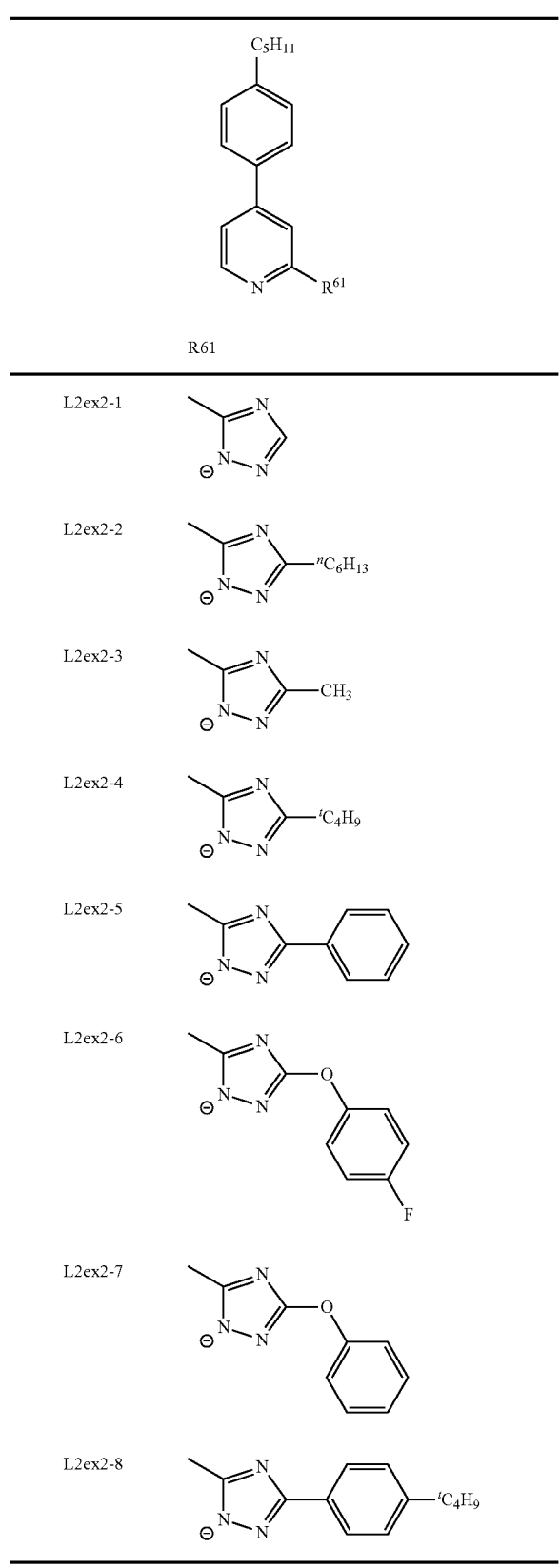

The "ligand $Z^1$" and "counterion CI for neutralizing the charge" in Formula (I) of the second embodiment have the same definition as described above for the metal complex dye of the first embodiment.

In the second embodiment, the metal complex dye represented by Formula (I) is preferably a metal complex dye represented by the following Formula (XXII), and more preferably a metal complex dye represented by the following Formula (XXIII)

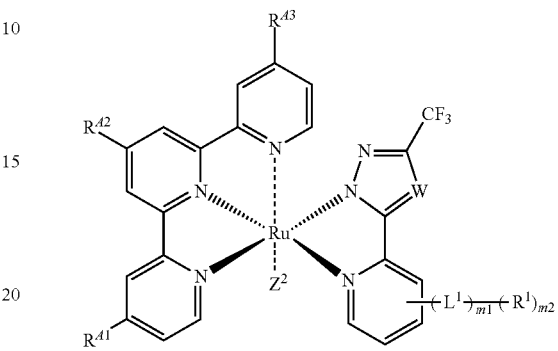

Formula (XXII)

In Formula (XXII), $R^{A1}$ to R the same definition as that of $R^{A1}$ to $R^{A3}$ in Formula (AL-3). $R^1$, $L^1$, m1, and m2 have the same definition as that of $R^1$, $L^1$, m1, and m2 in Formula (DL-21). W represents CH. $Z^2$ represents an isothiocyanate group, an isoselenocyanate group, an isocyanate group, a halogen atom, or a cyano group.

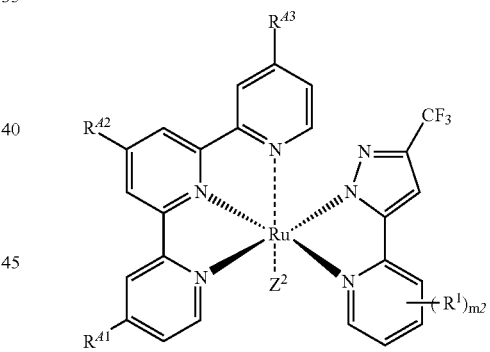

Formula (XXIII)

In Formula (XXIII), $R^{A1}$ to R the same definition as that of $R^{A1}$ to $R^{A3}$ in Formula (AL-3). $R^1$ and m2 have the same definition as that of $R^1$ and m2 in Formula (DL-21). $Z^2$ has the same definition as that of $Z^2$ in Formula (XXII).

Specific examples of the metal complex dye represented by Formula (I) of the second embodiment will be shown below, but the present invention is not limited thereto.

The ligand is in a state of forming a coordinate bond with a metal atom. That is, the atom forming a coordinate bond through an anion is represented by an anion, but the ligand does not need to form a coordinate bond through an anion.

Furthermore, although the counterion is not shown in the metal complex dye, the counterion is not unnecessary, and the metal complex dye can retain a certain counterion. Examples of the counterion include the aforementioned CI.

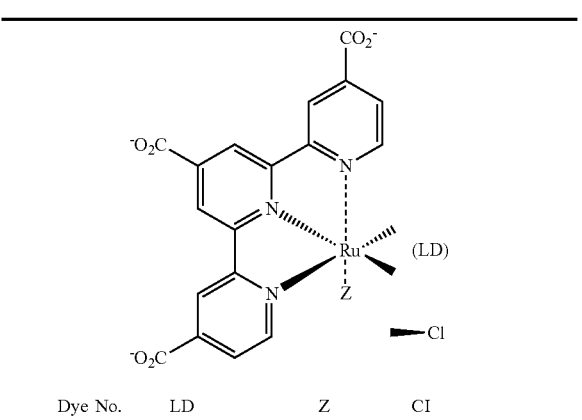

| Dye No. | LD | Z | CI |
|---|---|---|---|
| D-1-1a | L2ex1-1 | Zex7 | (H+)3 |
| D-1-1b | L2ex1-1 | Zex7 | (H+)2(N+Bu4) |
| D-1-1c | L2ex1-1 | Zex7 | (H+)(N+Bu4)2 |
| D-1-1d | L2ex1-1 | Zex7 | (N+Bu4)3 |
| D-1-1e | L2ex1-1 | Zex7 | (H+)2(Na+) |
| D-1-1f | L2ex1-1 | Zex7 | (H+)1(K+)2 |
| D-1-1g | L2ex1-1 | Zex7 | (H+)2(K+)1 |
| D-1-2a | L2ex1-2 | Zex7 | (H+)3 |
| D-1-2b | L2ex1-2 | Zex7 | (H+)2(N+Bu4) |
| D-1-2c | L2ex1-2 | Zex7 | (H+)(N+Bu4)2 |
| D-1-2d | L2ex1-2 | Zex7 | (N+Bu4)3 |
| D-1-3a | L2ex1-6 | Zex7 | (H+)3 |
| D-1-4a | L2ex1-7 | Zex7 | (H+)3 |
| D-1-4b | L2ex1-7 | Zex7 | (H+)2(N+Bu4) |
| D-1-4c | L2ex1-7 | Zex7 | (H+)(N+Bu4)2 |
| D-1-4d | L2ex1-7 | Zex7 | (N+Bu4)3 |
| D-1-5a | L2ex1-23 | Zex7 | (H+)3 |
| D-1-5b | L2ex1-23 | Zex7 | (H+)2(N+Bu4) |
| D-1-5c | L2ex1-23 | Zex7 | (H+)(N+Bu4)2 |
| D-1-5d | L2ex1-23 | Zex7 | (N+Bu4)3 |
| D-1-5e | L2ex1-23 | Zex7 | (H+)1(K+)2 |
| D-1-5f | L2ex1-23 | Zex7 | (H+)2(K+)1 |
| D-1-5g | L2ex1-23 | Zex7 | (H+)2(Na+) |
| D-1-6a | L2ex1a-2 | Zex7 | (H+)3 |
| D-1-6b | L2ex1a-2 | Zex7 | (H+)2(N+Bu4) |
| D-1-6c | L2ex1a-2 | Zex7 | (H+)(N+Bu4)2 |
| D-1-6d | L2ex1a-2 | Zex7 | (N+Bu4)3 |
| D-1-7a | L2ex1-4 | Zex7 | (H+)3 |
| D-1-8a | L2ex1-5 | Zex7 | (H+)3 |
| D-1-9a | L2ex1-44 | Zex7 | (H+)3 |
| D-1-10a | L2ex1-8 | Zex7 | (H+)3 |
| D-1-11a | L2ex1-13 | Zex7 | (H+)3 |
| D-1-12a | L2ex1-9 | Zex7 | (H+)3 |
| D-1-13a | L2ex1-26 | Zex7 | (H+)3 |
| D-1-14a | L2ex1-57 | Zex7 | (H+)3 |
| D-1-15a | L2ex1-22 | Zex7 | (H+)3 |
| D-1-16a | L2ex1a-3 | Zex7 | (H+)3 |

| Dye No. | LD | Z | CI |
|---|---|---|---|
| D-1-17a | L2ex1a-4 | Zex7 | (H+)3 |
| D-1-18a | L2ex1a-5 | Zex7 | (H+)3 |
| D-1-19a | L2ex2-1 | Zex7 | (H+)3 |

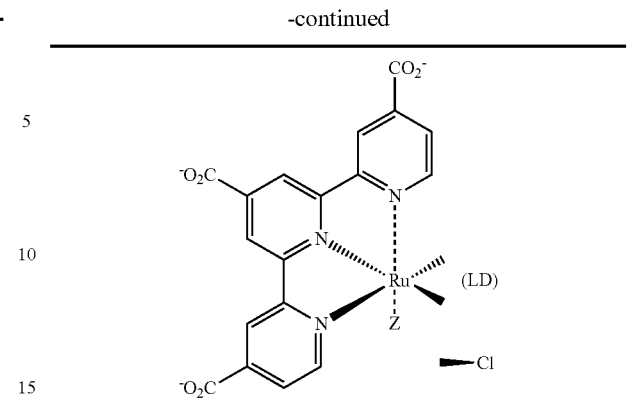

| Dye No. | LD | Z | CI |
|---|---|---|---|
| D-1-20a | L2ex2-2 | Zex7 | (H+)3 |
| D-1-21a | L2ex2-3 | Zex7 | (H+)3 |
| D-1-22a | L2ex2-4 | Zex7 | (H+)3 |
| D-1-23a | L2ex2-5 | Zex7 | (H+)3 |
| D-1-24a | L2ex1b-5 | Zex7 | (H+)3 |
| D-1-25a | L2ex1-59 | Zex7 | (H+)3 |
| D-1-26a | L2ex1b-3 | Zex7 | (H+)3 |
| D-1-27a | L2ex1-9 | Zex1 | (H+)3 |
| D-1-28a | L2ex1-9 | Zex8 | (H+)3 |
| D-1-29a | L2ex1-9 | Zex9 | (H+)3 |
| D-1-30a | L2ex1-9 | Zex3 | (H+)3 |
| D-1-31a | L2ex1-9 | Zex5 | (H+)3 |
| D-1-32a | L2ex1-9 | Zex10 | (H+)3 |
| D-1-33a | L2ex1-9 | Zex4 | (H+)3 |

| Dye No. | LA | LD | CI |
|---|---|---|---|
| D-2-1a | B-1-9 | L2ex1-9 | — |
| D-2-1b | B-1-9 | L2ex1-11 | — |
| D-2-1c | B-1-9 | L2ex1-9 | — |
| D-2-1d | B-1-9 | L2ex1a-2 | — |
| D-2-2a | Bex1 | L2ex1-3 | (H+)2 |
| D-2-3a | Bex3 | L2ex1-6 | (H+)1 |
| D-2-4a | Bex4 | L2ex1a-1 | (H+)1 |
| D-2-6a | Bex3 | L2ex1a-6 | (H+)1 |
| D-2-7a | Bex5 | L2ex1a-4 | (H+)1 |
| D-2-8a | B-1-7 | L2ex1-23 | — |
| D-2-9a | B-1-1 | L2ex1-23 | — |
| D-2-10a | B-1-3 | L2ex1-23 | — |

| Dye No. | LA | LD | Z | M | CI |
|---|---|---|---|---|---|
| D-3-1a | Bex2 | L2ex1-9 | Zex7 | Os | (H+)3 |
| D-3-1b | Bex2 | L2ex1-9 | Zex7 | Os | (H+)2(N+Bu4) |
| D-3-1c | Bex2 | L2ex1-9 | Zex7 | Os | (H+)(N+Bu4)2 |
| D-3-1d | Bex2 | L2ex1-9 | Zex7 | Os | (N+Bu4)3 |
| D-3-2a | Bex3 | L2ex1-9 | Zex10 | Ir | (H+)1 |

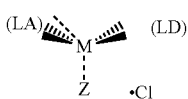

| Dye No. | LA | LD | Z | M | Cl |
|---------|-----|---------|------|----|-----------|
| D-3-3a | Bex2 | L2ex1-11 | Zex3 | Rh | $(H^+)_3$ |
| D-3-4a | Bex4 | L2ex1-57 | Zex9 | Co | $(H^+)_1$ |
| D-3-5a | Bex2 | L2ex1-9 | Zex2 | Ru | $(H^+)_3$ |
| D-3-6a | Bex2 | L2ex1-9 | Zex6 | Ru | $(H^+)_3$ |

Zex 1 —NCSe

Zex 2 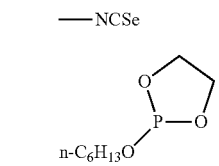

Zex 3 —Cl

Zex 4 —Br

Zex 5 —I

Zex 6 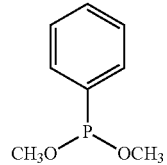

Zex 7 —NCS

Zex 8 —NCO

Zex 9 —SCN

Zex 10 —CN

Bex 1 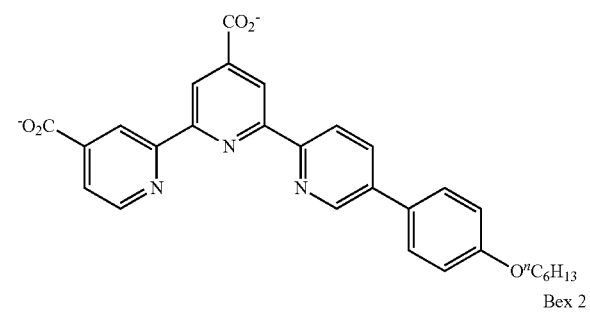

Bex 2 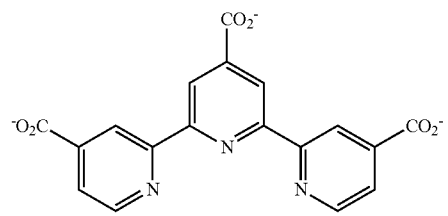

Bex 3 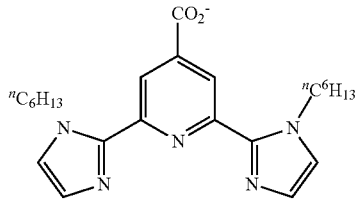

Bex 4 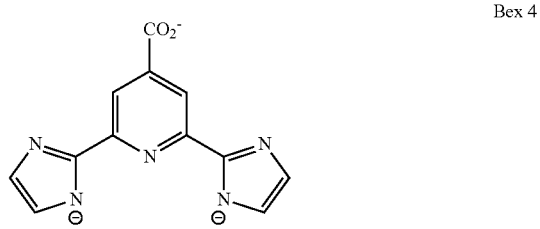

Bex 5 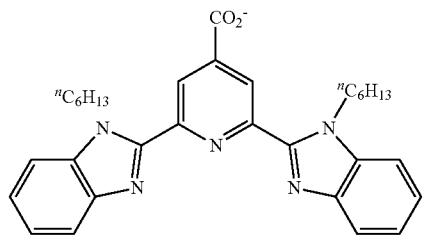

Through examination, the inventors of the present invention figured out that, in the metal complex dyes described in U.S. Pat. No. 5,463,057A and US2010/0258175A, voltage heavily depends on the concentration of an electrolyte. In the metal complex dye of the second embodiment, the durability and photoelectric conversion efficiency are improved, and the dependence of voltage on the concentration of an electrolyte is reduced.

The metal complex dye represented by Formula (I) of the first and second embodiments can be synthesized by the methods described in US2010/0258175A1, U.S. Pat. No. 4,298,799A, and Angew. Chem. Int. Ed., 2011, 50, 2054-2058, the methods described in reference documents exemplified in the above documents, or methods based on the above methods.

The maximum absorption wavelength of the metal complex dye of the present invention in a solution is preferably within a range of 300 nm to 1,000 nm, more preferably within a range of 350 nm to 950 nm, and particularly preferably within a range of 370 nm to 900 nm.

In the present invention, the metal complex dye of the present invention may be used concurrently with other dyes. Examples of the concurrently used dyes include the Ru complex dyes described in JP1995-500630A (JP-H07-500630A) (particularly, the dyes synthesized in Examples 1 to 19 described in the 5$^{th}$ line of left lower column on page 5 to the 7$^{th}$ line of right upper column on page 7), the Ru complex dyes described in JP2002-512729A (particularly, the dyes synthesized in Examples 1 to 16 described in the 3$^{rd}$ line from the bottom of page 20 to the 23$^{rd}$ line on page 29), the Ru complex dyes described in JP2001-59062A (particularly, the dyes described in paragraphs [0087] to [0104]), the Ru complex dyes described in JP2001-6760A (particularly, the dyes described in paragraphs [0093] to [0102]), the Ru complex dyes described in JP2001-253894A (particularly, the dyes described in paragraphs [0009] and [0010]), the Ru complex dyes described in JP2003-212851A (particularly, the dyes described in paragraph [0005]), the Ru complex dyes described in WO2007/91525A (particularly, the dyes described in paragraph [0067]), the Ru complex dyes described in JP2001-291534A (particularly, the dyes described in paragraphs [0120] to [0144]), the Ru complex dyes described in JP2012-012570A (particularly, the dyes described in paragraphs [0095] to [0103]), the Ru complex dyes described in WO2013/47615A (particularly, the dyes described in paragraphs [0078] to [0082]), the squarylium cyanine dyes described in JP1999-214730A (JP-H11-214730A) (particularly, the dyes described in paragraphs [0036] to [0047]), the squarylium cyanine dyes described in JP2012-144688A (particularly, the dyes described in paragraphs [0039] to [0046] and paragraphs [0054] to [0060]), the squarylium cyanine dyes described in JP2012-84503A (particularly, the dyes described in paragraphs [0066] to [0076] and the like), organic dyes described in JP2004-063274A (particularly, the dyes described in paragraphs [0017] to [0021]), the organic dyes described in JP2005-123033A (particularly, the dyes described in paragraphs [0021] to [0028]), the organic dyes described in JP2007-287694A (particularly, the dyes described in paragraphs [0091] to [0096]), the organic dyes described in JP2008-71648A (particularly, the dyes described in paragraphs [0030] to [0034]), the organic dyes described in WO2007/119525A (particularly, the dyes described in paragraph [0024]), the porphyrin dyes described in Angew. Chem. Int. Ed., 49, 1 to 5 (2010) and the like, and the phthalocyanine dyes described in Angew. Chem. Int. Ed., 46, 8358 (2007).

Preferred examples of the concurrently used dyes include a Ru complex dye, a squarylium cyanine dye, and an organic dye.

When the metal complex dye of the present invention is used concurrently with other dyes, a mass ratio of the metal complex dye of the present invention/other dyes is preferably 95/5 to 10/90, more preferably 95/5 to 50/50, even more preferably 95/5 to 60/40, particularly preferably 95/5 to 65/35, and most preferably 95/5 to 70/30.

—Conductive Support—

The conductive support is preferably a metal support having conductivity. Alternatively, it is preferably a glass or plastic support having a conductive film layer on the surface thereof. Examples of the plastic support include the transparent polymer film described in paragraph [0153] of JP2001-291534A. As the support, in addition to glass or plastic, ceramics (JP2005-135902A) and conductive resins (JP2001-160425A) may be used. A light management function may be given to the surface of the conductive support. For example, the conductive support may have an antireflection film described in JP2003-123859A that is obtained by alternately laminating a high-refractive index film and a low-refractive index oxide film on each other, or may have a light guide function described in JP2002-260746A.

The thickness of the conductive film layer is preferably 0.01 µm to 30 µm, more preferably 0.03 µm to 25 µm, and particularly preferably 0.05 µm to 20 µm.

It is preferable for the conductive support to be substantially transparent. The state in which the conductive support is substantially transparent means that the light transmittance thereof is equal to or greater than 10%. The light transmittance of the conductive support is preferably equal to or greater than 50%, and particularly preferably equal to or greater than 80%. As the transparent conductive support, a support is preferable which is obtained by coating glass or plastic with a conductive metal oxide. As the metal oxide, tin oxide is preferable, and indium tin oxide and a fluorine-doped oxide are particularly preferable. At this time, the amount of the conductive metal oxide used for coating is preferably 0.1 g to 100 g per 1 m$^2$ of the glass or plastic support. When the transparent conductive support is used, it is preferable to cause light to enter from the support side.

—Semiconductor Particles—

The semiconductor particles are preferably particles of chalcogenide (such as an oxide, a sulfide, or selenide) of a metal or particles of Perovskite. Preferred examples of the chalcogenide of a metal include titanium, tin, zinc, tungsten, zirconium, hafnium, strontium, indium, cerium, yttrium, lanthanum, vanadium, niobium, tantalum, an oxide of these, cadmium sulfide, cadmium selenide, and the like. Preferred examples of Perovskite include strontium titanate, calcium titanate, and the like. Among these, titanium oxide (titania), zinc oxide, tin oxide, and tungsten oxide are particularly preferable.

Examples of the crystal structure of titania include an anatase type, a Brookite-type, and a rutile-type, and among these, an anatase-type and a Brookite-type are preferable. Titania nanotubes, titania nanowires, or nanorods may be mixed with titania particles or used as a semiconductor electrode.

The particle size of the semiconductor particles is a mean particle size obtained by using a diameter that is determined by converting the projected area of the particles into a circle. The particle size is preferably 0.001 µm to 1 µm in terms of a primary particle size, and preferably 0.01 µm to 100 µm in terms of a mean particle size of a dispersion. Examples of the method for coating the conductive support with semiconductor particles include a wet method, a dry method, and other methods.

In order to prevent the reverse current caused by the direct contact between the electrolyte and the electrode, it is preferable to form a short circuit-preventing layer between the transparent conductive film and the semiconductor layer (photoreceptor layer). Moreover, in order to prevent contact between the photoelectrode and the counter electrode, it is preferable to use a spacer or a separator. It is preferable for the semiconductor particles to have a large surface area such that the particles can adsorb a large amount of dye. For example, in a state in which the support is coated with the semiconductor particles, the surface area is preferably not less than 10 times the size of the projected area, and more preferably not less than 100 times the size of the projected area. The upper limit of the surface area is not particularly limited, but usually, the surface area is about 5,000 times the size of the projected area. Generally, the greater the thickness of the layer containing the semiconductor particles, the larger the amount of the dye that can be carried per unit area, and consequentially, light absorption efficiency is improved. However, because the generated electrons are diffused farther away, the loss resulting from charge recombination also increases. Typically, the thickness of the photoreceptor layer as a semiconductor layer is preferably 0.1 µm to 100 µm, although the thickness varies with the use of the element. When the photoelectric conversion element is used as a dye-sensitized solar cell, the thickness of the photoreceptor layer is preferably 1 µm to 50 µm, and more preferably 3 µm to 30 µM After being coated with the semiconductor particles, the support may be fired at a temperature of 100° C. to 800° C. for 10 minutes to 10 hours such that the semiconductor particles adhere to each other. When glass is used as the support, the film formation temperature is preferably 60° C. to 400° C.

The amount of the semiconductor particles used for coating is preferably 0.5 g to 500 g and more preferably 5 g to 100 g per 1 m$^2$ of the support. The total amount of the dye used is preferably 0.01 mmol to 100 mmol, more preferably 0.1 mmol to 50 mmol, and particularly preferably 0.1 mmol to 10 mmol per 1 m$^2$ of the support. In this case, the amount of the used metal complex dye of the present invention is preferably equal to or greater than 5 mol %. Furthermore, the amount of the dye adsorbed onto the semiconductor particles is preferably 0.001 mmol to 1 mmol and more preferably 0.1 mmol to 0.5 mmol, with respect to 1 g of the semiconductor particles. If the amount of the dye is within the above range, a sensitizing effect in the semiconductor particles is sufficiently obtained.

When the dye is a salt, the counterion of the specific metal complex dye is not particularly limited, and examples of the counterion include an alkali metal ion, a quaternary ammonium ion, and the like.

After the dye is adsorbed onto the semiconductor particles, the surface of the semiconductor particles may be treated with amines. Preferred examples of the amines include pyridines (such as 4-tert-butylpyridine and polyvinylpyridine) and the like. When the amines are in the form of a liquid, they may be used as is or may be used by being dissolved in an organic solvent.

In the photoelectric conversion element (such as the photoelectric conversion element 10) and the dye-sensitized solar cell (such as the dye-sensitized solar cell 20) of the present invention, at least the aforementioned metal complex dye of the present invention is used.

—Charge Carrier Layer—

The charge carrier layer used in the photoelectric conversion element of the present invention is a layer that functions to supply electrons to the oxidized dye and is disposed between the light-receiving electrode and the counter electrode. The charge carrier layer contains an electrolyte. Examples of the electrolyte include a liquid electrolyte obtained by dissolving redox pairs in an organic solvent, an electrolyte (so-called gel electrolyte) obtained by impregnating a polymer matrix with a liquid obtained by dissolving redox pairs in an organic solvent, molten salts containing redox pairs, and the like. In order to improve the photoelectric conversion efficiency, it is preferable to use a liquid electrolyte. As the solvent of the liquid electrolyte, a nitrile compound, an ether compound, an ester compound, and the like are used. As the solvent of the liquid electrolyte, a nitrile compound is preferable, and acetonitrile and methoxypropionitrile are particularly preferable.

Examples of the redox pairs include a combination of iodine and an iodide (preferably an iodide salt or iodized ionic liquid and more preferably lithium iodide, tetrabutylammonium iodide, tetrapropylammonium iodide, and methyl propylimidazolium iodide), a combination of alkylviologen (such as methylviologen chloride, hexylviologen bromide, or benzylviologen tetrafluoroborate) and an oxidized product thereof, a combination of polyhydroxybenzenes (such as hydroquinone and naphthohydroquinone) and a reduced product thereof, a combination of a divalent iron complex and a trivalent iron complex (such as a combination of potassium ferricyanide and yellow prussiate of potash), a combination of a divalent cobalt complex and a trivalent cobalt complex, and the like. Among these, a combination of iodine and an iodide and a combination of a divalent cobalt complex and a trivalent cobalt complex are preferable.

The cobalt complex is particularly preferably a complex represented by the following Formula (CC).

$$Co(LL)ma(X)mb.CI \quad \text{Formula (CC)}$$

In Formula (CC), LL represents a bidentate or tridentate ligand. X represents a monodentate ligand. ma represents an integer of 0 to 3. mb represents an integer of 0 to 6. CI represents a counterion used when a counterion is required for neutralizing the charge.

Examples of CI in Formula (CC) include CI in Formula (I).

LL is preferably a ligand represented by the following Formula (LC).

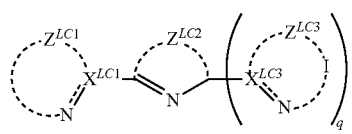

Formula (LC)

In Formula (LC), each of $X^{LC1}$ and $X^{LC3}$ independently represents a carbon atom or a nitrogen atom. Herein, when $X^{LC1}$ represents a carbon atom, the bond between $X^{LC1}$ and a N atom represents a double bond ($X^{LC1}$=N). When $X^{LC3}$ represents a carbon atom, the bond between $X^{LC3}$ and a N atom represents a double bond ($X^{LC3}$=N). When $X^{LC1}$ represents a nitrogen atom, the bond between $X^{LC1}$ and a N atom represents a single bond ($X^{LC1}$—N). When $X^{LC3}$ represents a nitrogen atom, the bond between $X^{LC3}$ and a N atom represents a single bond ($X^{LC3}$—N).

Each of $Z^{LC1}$, $Z^{LC2}$, and $Z^{LC3}$ independently represents a group of non-metal atoms necessary for forming a 5-membered or 6-membered ring. $Z^{LC1}$, $Z^{LC2}$, and $Z^{LC3}$ may have a substituent and may form a closed ring together with an adjacent ring via the substituent. q represents 0 or 1. Examples of the substituent include the substituents T which will be described later. When q is 0, a hydrogen atom or a substituent other than a heterocyclic group formed by $Z^{LC3}$ is bonded to a carbon atom in a position in which $X^{LC3}$ is bonded to the 5-membered or 6-membered ring formed by $Z^{LC2}$.

Examples of X include $Z^1$ in Formula (I). X is preferably a halogen ion.

The ligand represented by Formula (LC) is more preferably a ligand represented by the following Formulae (LC-1) to (LC-4).

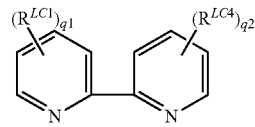

Formula (LC-1)

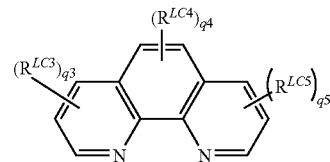

Formula (LC-2)

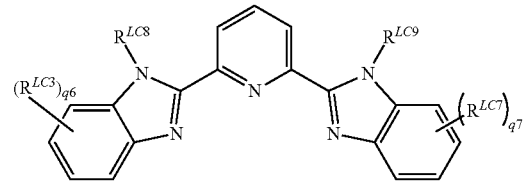

Formula (LC-3)

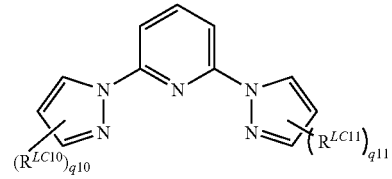

Formula (LC-4)

Each of $R^{LC1}$ to $R^{LC11}$ independently represents a substituent. Each of q1, q2, q6, and q7 independently represents an integer of 0 to 4. Each of q3, q5, q10, and q11 independently represents an integer of 0 to 3. q4 represents an integer of 0 to 2.

Examples of the substituents represented by $R^{LC1}$ to $R^{LC11}$ in Formulae (LC-1) to (LC-4) include an aliphatic group, an aromatic group, a heterocyclic group, and the like. Specific examples of the substituents represented by $R^{LC1}$ to $R^{LC11}$ include an alkyl group, an alkoxy group, an alkylthio group, an aryl group, an aryloxy group, an arylthio group, a heterocyclic group, and the like. Preferred examples thereof include an alkyl group (such as methyl, ethyl, n-butyl, n-hexyl, isobutyl, sec-butyl, t-butyl, n-dodecyl, cyclohexyl, or benzyl), an aryl group (such as phenyl, tolyl, or naphthyl), an alkoxy group (such as methoxy, ethoxy, isopropoxy, or butoxy), an alkylthio group (such as methylthio, n-butylthio, n-hexylthio, or 2-ethylhexylthio), an aryloxy group (such as phenoxy or naphtoxy), an arylthio group (such as phenylthio or naphthylthio), and a heterocyclic group (such as 2-thienyl or 2-furyl).

Specific examples of the cobalt complex having the ligand represented by Formula (LC) include the following complexes.

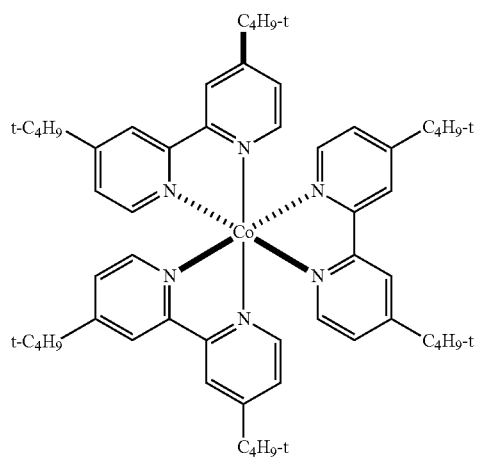

LL-1

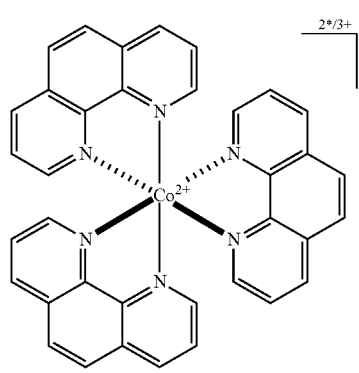

LL-2

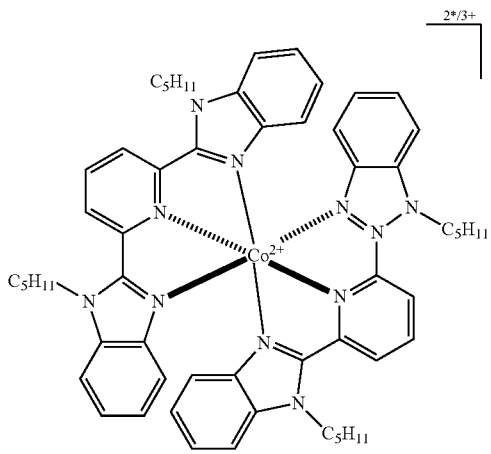

LL-3

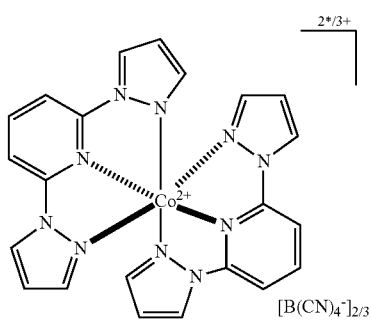

LL-4

When a combination of iodine and an iodide is used as an electrolyte, it is preferable to concurrently use an iodine salt of a nitrogen-containing aromatic cation of a 5-membered ring or a 6-membered ring.

As the organic solvent for dissolving the redox pairs and the like, a nonprotonic polar solvent (such as acetonitrile, propylene carbonate, ethylene carbonate, dimethylformamide, dimethyl sulfoxide, sulfolane, 1,3-dimethyl imidazolinone, or 3-methyl oxazolidinone) is preferable. Examples of the polymer used as the matrix of a gel electrolyte include polyacrylonitrile, polyvinylidene fluoride, and the like. Examples of the molten salt include those obtained by mixing polyethylene oxide with lithium iodide and at least one kind of another lithium salt (such as lithium acetate or lithium perchlorate) such that the resultant exhibits fluidity at room temperature. In this case, the amount of the polymer added is 1% by mass to 50% by mass. Furthermore, the electrolytic solution may contain γ-butyrolactone. If the electrolytic solution contains γ-butyrolactone, the iodide ion is more efficiently diffused, and therefore the photoelectric conversion efficiency is improved.

As the additives, in addition to the aforementioned 4-tert-butylpyridine, an aminopyridine-based compound, a benzimidazole-based compound, an aminotriazole-based compound, an aminothiazole-based compound, an imidazole-based compound, an aminotriazine-based compound, a urea derivative, an amide compound, a pyrimidine-based compound, and a heterocyclic ring not containing nitrogen can be added to the electrolyte.

Moreover, in order to improve the photoelectric conversion efficiency, a method of controlling the water content in the electrolytic solution may be adopted. Preferred examples of the method of controlling the water content include a method of controlling the concentration and a method of adding a dehydrating agent to the electrolytic solution. In order to reduce the toxicity of iodine, a clathrate compound of iodine and cyclodextrin may be used, or a method of consistently supplying water may be used. In addition, cyclic amidine may be used, or an antioxidant, a hydrolysis inhibitor, a stabilizing agent, or zinc iodide may be added.

Molten salts may be used as the electrolyte, and examples of preferred molten salts include an ionic liquid containing imidazolium or a triazolium-type cation, an oxazolium-based molten salt, a pyridinium-based molten salt, a guanidium-based molten salt, and a combination of these. These cationic molten salts may be combined with a specific anion. Furthermore, additives may be added to these molten salts, and the molten salts may have a liquid crystal substituent. Moreover, a quaternary ammonium salt-based molten salt may be used.

Examples of molten salts other than the above include those obtained by mixing polyethylene oxide with lithium iodide and at least one kind of another lithium salt (such as lithium acetate or lithium perchlorate) such that the resultant exhibits fluidity at room temperature.

A gellant may be added to the electrolytic solution composed of the electrolyte and a solvent so as to cause gelation and make the electrolyte into a pseudo-solid. Examples of the gellant include an organic compound having a molecular weight of equal to or less than 1,000, a Si-containing compound having a molecular weight within a range of 500 to 5,000, an organic salt composed of a specific acidic compound and a basic compound, a sorbitol derivative, and polyvinylpyridine.

Furthermore, a method may be used in which a matrix polymer, a crosslinked polymer compound or monomer, a crosslinking agent, an electrolyte, and a solvent are trapped in a polymer.

Preferred examples of the matrix polymer include a polymer having a nitrogen-containing heterocyclic ring in a repeating unit of a main chain or a side chain, a crosslinked polymer obtained by reacting the aforementioned nitrogen-containing heterocyclic ring with an electrophilic compound, a polymer having a triazine structure, a polymer having a ureide structure, a polymer containing a liquid crystal compound, a polymer having an ether bond, a polyvinylidene fluoride-based polymer, a polymer based on methacrylate-acrylate, a thermosetting resin, crosslinked polysiloxane, polyvinyl alcohol (PVA), a clathrate compound of polyalkylene glycol, dextrin, and the like, a polymer to which a oxygen-containing polymer or a sulfur-containing polymer has been added, a natural polymer, and the like. To these polymers, an alkali-swellable polymer, a polymer having a compound that can form a charge carrier complex of a cationic moiety and iodine in a single polymer, and the like may be added.

As the matrix polymer, polymers including a crosslinked polymer, which is obtained by reacting isocyanate having two or more functional groups with a functional group such as a hydroxy group, an amino group, or a carboxyl group, may be used. In addition, a crosslinking method may be used in which a crosslinked polymer composed of a hydrosilyl group and a compound forming a double bond, polysulfonic acid, polycarboxylic acid, or the like is reacted with a metal ion compound having two or more functional groups.

Examples of the solvent that can be preferably used in combination with the aforementioned pseudo-solid electrolyte include a specific phosphoric acid ester, a solvent mixture containing ethylene carbonate, a solvent having a specific dielectric constant, and the like. Moreover, a method of keeping the solution of a liquid electrolyte in a solid electrolyte membrane or in small pores may be used, and preferred examples of such a method include methods using a conductive polymer film, a fibrous solid, or a cloth-like solid such as a filter.

Instead of the liquid electrolyte and the pseudo-solid electrolyte described above, a solid charge transport layer such as a p-type semiconductor or a hole transport material, for example, CuI, CuNSC, or the like can be used. Furthermore, the electrolyte described in Nature, vol. 486, p. 487 (2012) and the like may be used. As the solid charge transport layer, an organic hole transport material may be used. Preferred examples of the hole transport layer include a conductive polymer such as polythiophene, polyaniline, polypyrrole, or polysilane, a spiro compound in which two rings share a central element such as C or Si that forms a tetrahedral structure, an aromatic amine derivative such as triaryl amine, a triphenylene derivative, a nitrogen-containing heterocyclic derivative, and a liquid crystal cyano derivative.

The redox pairs become electron carriers. Therefore, the concentration thereof needs to reach a certain degree. The total concentration of the redox pairs is preferably equal to or greater than 0.01 mol/L, more preferably equal to or greater than 0.1 mol/L, and particularly preferably equal to or greater than 0.3 mol/L. The upper limit of the total concentration of the redox pairs is not particularly limited, but is generally about 5 mol/L.

—Coadsorbent—

In the photoelectric conversion element of the present invention, a coadsorbent is preferably used together with the metal complex dye of the present invention or the dye that is concurrently used if necessary. As the coadsorbent, a coadsorbent having one or more acidic groups (preferably a carboxy group or a group of a salt thereof) is preferable, and examples thereof include a fatty acid and a compound having a steroid skeleton. The fatty acid may be a saturated fatty acid or an unsaturated fatty acid, and examples thereof include butanoic acid, hexanoic acid, octanoic acid, decanoic acid, hexadecanoic acid, dodecanoic acid, palmitic acid, stearic acid, oleic acid, linoleic acid, linolenic acid, and the like.

Examples of the compound having a steroid skeleton include cholic acid, glycocholic acid, chenodeoxycholic acid, hyocholic acid, deoxycholic acid, lithocholic acid, ursodeoxycholic acid, and the like. Among these, cholic acid, deoxycholic acid, and chenodeoxycholic acid are preferable, and chenodeoxycholic acid is more preferable.

A compound represented by the following Formula (CA) is preferable as the coadsorbent.

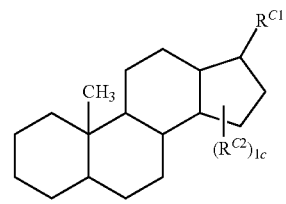

Formula (CA)

In Formula (CA), $R^{C1}$ represents a substituent having an acidic group. $R^{C2}$ represents a substituent. lc represents an integer of equal to or greater than 0.

The definition of the acidic group is the same as described above, and a preferred range thereof is also the same.

Among the acidic groups, a carboxy group, a sulfo group, or an alkyl group substituted with a salt of these is preferable as $R^{C1}$, and —CH(CH$_3$)CH$_2$CH$_2$CO$_2$H or —CH(CH$_3$)CH$_2$CH$_2$CONHCH$_2$CH$_2$SO$_3$H is more preferable as $R^{C1}$.

Examples of $R^{C2}$ include the substituents T which will be described later. Among the substituents, an alkyl group, a hydroxy group, an acyloxy group, an alkylaminocarbonyloxy group, and an arylaminocarbonyloxy group are preferable, and an alkyl group, a hydroxy group, and an acyloxy group are more preferable.

nA is preferably 2 to 4.

Examples of specific compounds of these include the compounds exemplified above as the compound having a steroid skeleton.

The coadsorbent is adsorbed onto the semiconductor particles, and in this way, the coadsorbent exerts an effect of inhibiting inefficient intermixing of dyes and an effect of preventing electrons from moving back to the redox system in the electrolyte from the surface of the semiconductor particles. The amount of the coadsorbent used is not particularly limited. However, from the viewpoint of causing the coadsorbent to effectively exert the aforementioned effects, the amount of the coadsorbent is preferably 1 mol to 200 mol, more preferably 10 mol to 150 mol, and particularly preferably 20 mol to 50 mol, with respect to 1 mol of the dye.

<Substituents T>

In the present specification, a compound (including a complex and dye) means not only the compound itself but also a salt and an ion thereof. In addition, in the present specification, when there is no description regarding whether or not a substituent is substituted or unsubstituted, it means that the substituent may have any substituent (the same will applied to a linking group and a ligand). Similarly, when there is no description regarding whether or not a compound is substituted or unsubstituted, it means that the compound may have any substituent. Examples of preferred substituents include the following substituents T.

Moreover, in the present specification, when a group is simply described as a substituent, the substituents T can be referred to. In addition, when a group is simply described as, for example, an alkyl group, a preferred range and specific examples of groups corresponding to the substituents T are applied to the group.

Examples of the substituents T include the following groups.

An alkyl group (preferably having 1 to 20 carbon atoms, for example, methyl, ethyl, isopropyl, t-butyl, pentyl, heptyl, 1-ethylpentyl, benzyl, 2-ethoxyethyl, 1-carboxymethyl, or trifluoromethyl), an alkenyl group (preferably having 2 to 20 carbon atoms, for example, vinyl, allyl, or oleyl), an alkynyl group (preferably having 2 to 20 carbon atoms, for example, ethynyl, butadiynyl, or phenylethynyl), a cycloalkyl group (preferably having 3 to 20 carbon atoms, for example, cyclopropyl, cyclopentyl, cyclohexyl, or 4-methylcyclohexyl), a cycloalkenyl group (preferably having 5 to 20 carbon atoms, for example, cyclopentenyl or cyclohexenyl), an aryl group (preferably having 6 to 26 carbon atoms, for example, phenyl, 1-naphthyl, 4-methoxyphenyl, 2-chlorophenyl, or 3-methylphenyl), a heterocyclic group (preferably having 2 to 20 carbon atoms; the heterocyclic group is more preferably a heterocyclic group of a 5-membered ring or 6-membered ring having at least one oxygen atom, sulfur atom, or nitrogen atom, for example, 2-pyridyl, 4-pyridyl, 2-imidazolyl, 2-benzimidazolyl, 2-thiazolyl, or 2-oxazolyl), an alkoxy group (preferably having 1 to 20 carbon atoms, for example, methoxy, ethoxy, isopropyloxy, or benzyloxy), an alkenyloxy group (preferably having 2 to 20 carbon atoms, for example, vinyloxy or allyloxy), an alkynyloxy group (preferably having 2 to 20 carbon atoms, for example, 2-propynyloxy or 4-butynyloxy), a cycloalkyloxy group (preferably having 3 to 20 carbon atoms, for example, cyclopropyloxy, cyclopentyloxy, cyclohexyloxy, or 4-methylcyclohexyloxy), an aryloxy group (preferably having 6 to 26 carbon atoms, for example, phenoxy, 1-naphthyloxy, 3-methylphenoxy, or 4-methoxyphenoxy), a heterocyclic oxy group (for example, imidazolyloxy, benzimidazolyloxy, thiazolyloxy, benzothiazolyloxy, triazinyloxy, or purinyloxy), an alkoxycarbonyl group (preferably having 2 to 20 carbon atoms, for example, ethoxycarbonyl or 2-ethylhexyloxycarbonyl), a cycloalkoxycarbonyl group (preferably having 4 to 20 carbon atoms, for example, cyclopropyloxycarbonyl, cyclopentyloxycarbonyl, or cyclohexyloxycarbonyl), an aryloxycarbonyl group (preferably having 6 to 20 carbon atoms, for example, phenyloxycarbonyl or naphthyloxycarbonyl), an amino group (preferably having 0 to 20 carbon atoms, including an alkylamino group, an alkenylamino group, an alkynylamino group, a cycloalkylamino group, a cycloalkenylamino group, an arylamino group, and a heterocyclic amino group, for example, amino, N,N-dimethylamino, N,N-diethylamino, N-ethylamino, N-allylamino, N-(2-propynyl)amino, N-cyclohexylamino, N-cyclohexenylamino, anilino, pyridylamino, imidazolylamino, benzimidazolylamino, thiazolylamino, benzothiazolylamino, or triazinylamino), a sulfamoyl group (preferably having 0 to 20 carbon atoms; the sulfamoyl group is preferably a sulfamoyl group of alkyl, cycloalkyl, or aryl, for example, N,N-dimethylsulfamoyl, N-cyclohexylsulfamoyl, or N-phenylsulfamoyl), an acyl group (preferably having 1 to 20 carbon atoms, for example, acetyl, cyclohexylcarbonyl, or benzoyl), an acyloxy group (preferably having 1 to 20 carbon atoms, for example, acetyloxy, cyclohexylcarbonyloxy, or benzoyloxy), a carbamoyl group (preferably having 1 to 20 carbon atoms; the carbamoyl group is preferably a carbamoyl group of alkyl, cycloalkyl, or aryl, for example, N,N-dimethylcarbamoyl, N-cyclohexylcarbamoyl, or N-phenylcarbamoyl), an acylamino group (preferably an acylamino group having 1 to 20 carbon atoms, for example, acetylamino, cyclohexylcarbonylamino, or benzoylamino), a sulfonamide group (preferably having 0 to 20 carbon atoms; the sulfonamide group is preferably a sulfonamide group of alkyl, cycloalkyl, or aryl, for example, methanesulfonamide, benzenesulfonamide, N-methylmethanesulfonamide, N-cyclohexylsulfonamide, or N-ethylbenzenesulfonamide), an alkylthio group (preferably having 1 to 20 carbon atoms, for example, methylthio, ethylthio, isopropylthio, or benzylthio), a cycloalkylthio group (preferably having 3 to 20 carbon atoms, for example, cyclopropylthio, cyclopentylthio, cyclohexylthio, or 4-methylcyclohexylthio), an arylthio group (preferably having 6 to 26 carbon atoms, for example, phenylthio, 1-naphthylthio, 3-methylphenylthio, or 4-methoxyphenylthio), an alkylsulfonyl group, a cycloalkylsulfonyl group, or an arylsulfonyl group (preferably having 1 to 20 carbon atoms, for example, methylsulfonyl, ethylsulfonyl, cyclohexylsulfonyl, or benzenesulfonyl), a silyl group (preferably having 1 to 20 carbon atoms; the silyl group is preferably a silyl group substituted with alkyl, aryl, alkoxy, and aryloxy, for example, triethylsilyl, triphenylsilyl, diethylbenzylsilyl, or dimethylphenylsilyl), a silyloxy group (preferably having 1 to 20 carbon atoms; the silyloxy group is preferably a silyloxy group substituted with alkyl, aryl, alkoxy, and aryloxy, for example, triethylsilyloxy, triphenylsilyloxy, diethylbenzylsilyloxy, or dimethylphenylsilyloxy), a hydroxy group, a cyano group, a nitro group, a halogen atom (such as a fluorine atom, a chlorine atom, a bromine atom, or an iodine atom), a carboxy group, a sulfo group, a phosphonyl group, a phosphoryl group, and a boric acid group; among these, an alkyl group, an alkenyl group, a cycloalkyl group, an aryl group, a heterocyclic group, an alkoxy group, a cycloalkoxy group, an aryloxy group, an alkoxycarbonyl group, a cycloalkoxycarbonyl group, an amino group, an acylamino group, a cyano group, and a halogen atom are more preferable, and an alkyl group, an alkenyl group, a heterocyclic group, an alkoxy group, an alkoxycarbonyl group, an amino group, an acylamino group, and a cyano group are particularly preferable.

When a compound, a substituent, and the like contain an alkyl group, an alkenyl group, and the like, these may be linear or branched or may be substituted or unsubstituted. Furthermore, when a compound, a substituent, and the like contain an aryl group, a heterocyclic group, and the like, these may be a monocyclic ring or a fused ring or may be substituted or unsubstituted.

<Counter Electrode>

The counter electrode preferably functions as a positive electrode of the dye-sensitized solar cell (photoelectrochemical cell). Although the counter electrode generally has the same definition as the aforementioned conductive support, the support is not essentially required when the solar cell is constituted such that the strength thereof is sufficiently maintained. It is preferable for the counter electrode to have a structure exerting a high current-collecting effect. In order to allow light to reach the photoreceptor layer, at least one of the conductive support and the counter electrode should be substantially transparent. In the dye-sensitized solar cell, it is preferable to make the conductive support transparent and to cause sunlight to enter from the side of the support. In this case, it is more preferable for the counter electrode to have properties of reflecting the light. As the counter electrode of the dye-sensitized solar cell, glass or plastic onto which a metal or a conductive oxide has been vapor-deposited is preferable, and glass onto which platinum has been vapor-deposited is particularly preferable. In the dye-sensitized solar cell, in order to prevent evaporation of constituents thereof, it is preferable to seal the lateral surface of the cell by using a polymer, an adhesive, or the like.

The present invention can be applied to the photoelectric conversion elements and the dye-sensitized solar cells described in JP4260494B, JP2004-146425A, JP2000-340269A, JP2002-289274A, JP2004-152613A, and JP1997-27352A (JP-H09-27352A). Furthermore, the present invention can be applied to the photoelectric conversion elements and the dye-sensitized solar cells described in JP2004-152613A, JP2000-90989A, JP2003-217688A, JP2002-367686A, JP2003-323818A, JP2001-43907A, JP2000-340269A, JP2005-85500A, JP2004-273272A, JP2000-323190A, JP2000-228234A, JP2001-266963A, JP2001-185244A, JP2001-525108A, JP2001-203377A, JP2000-100483A, JP2001-210390A, JP2002-280587A, JP2001-273937A, JP2000-285977A, JP2001-320068A, and the like.

<<Dye Solution and Manufacturing Method of Dye-Adsorbed Electrode and Dye-Sensitized Solar Cell Using the Dye Solution>>

In the present invention, it is preferable to manufacture a dye-adsorbed electrode by using a dye solution containing the metal complex dye of the present invention.

Such a dye solution is obtained by dissolving the metal complex dye of the present invention in a solvent, and if necessary, the dye solution may contain a coadsorbent or other components.

Examples of the solvent used include the solvents described in JP2001-291534A, but the solvent is not particularly limited. In the present embodiment, an organic solvent is preferable, and alcohols, amides, nitriles, hydrocarbons, and a solvent mixture of two or more kinds of these are more preferable. The solvent mixture is preferably a solvent mixture obtained by mixing alcohols with a solvent selected from amides, nitriles, or hydrocarbons, more preferably a solvent mixture of alcohols and amides or of alcohols and hydrocarbons, and particularly preferably a solvent mixture of alcohols and amides. Specifically, methanol, ethanol, propanol, butanol, dimethylformamide, and dimethylacetamide are preferable.

The dye solution preferably contains a coadsorbent. As the coadsorbent, the aforementioned coadsorbents are preferable, and among these, the compound represented by Formula (CA) is preferable.

Herein, it is preferable to adjust the concentration of the metal complex dye or the coadsorbent such that the dye solution can be used as is at the time of manufacturing the photoelectric conversion element or the dye-sensitized solar cell. The dye solution preferably contains the metal complex dye of the present invention, in an amount of 0.001% by mass to 0.1% by mass.

It is particularly preferable to adjust the water content in the dye solution. Therefore, it is preferable to adjust the water content to be 0% by mass to 0.1% by mass.

Likewise, in order to make the effects of the present invention effectively exerted, it is preferable to adjust the water content of the electrolytic solution in the photoelectric conversion element or the dye-sensitized solar cell. Therefore, it is preferable to adjust the water content of the electrolytic solution to be 0% by mass to 0.1% by mass. It is particularly preferable to adjust the electrolytic solution by using the dye solution.

The dye-adsorbed electrode is preferably a dye-adsorbed electrode as a semiconductor electrode for a dye-sensitized solar cell which is obtained by causing the metal complex dye to be carried on the surface of the semiconductor particles contained in the semiconductor electrode by using the aforementioned dye solution.

That is, the dye-adsorbed electrode for a dye-sensitized solar cell is preferably a photoreceptor layer which is obtained by coating the conductive support, to which the semiconductor particles have been provided, with a composition obtained from the dye solution and curing the composition after coating.

A dye-sensitized solar cell is preferably manufactured in a manner in which the dye-adsorbed electrode of a dye-sensitized solar cell is used, and an electrolyte and a counter electrode are prepared, and then these are assembled together.

EXAMPLES

Hereinafter, the present invention will be more specifically described based on examples, but the present invention is not limited thereto.

<<First Embodiment>>

<Synthesis of Metal Complex Dye>

Hereinafter, by using examples, synthesis methods of dyes of the first embodiment will be specifically described. However, the starting material, dye intermediate, and synthesis route are not limited to the following methods.

First, the following example metal complex dyes were synthesized.

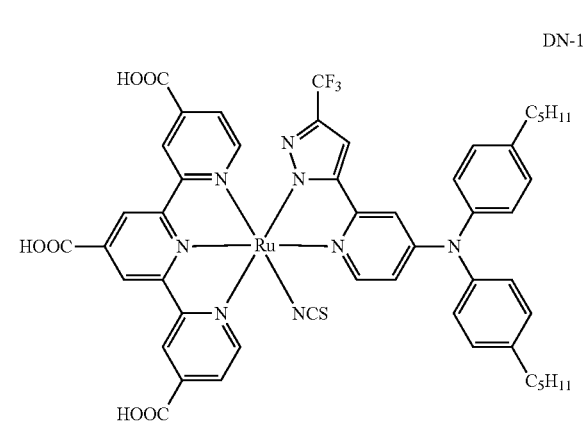

DN-1

-continued
DN-2
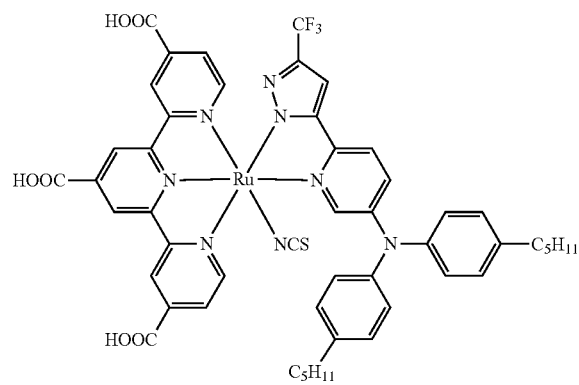
DN-13
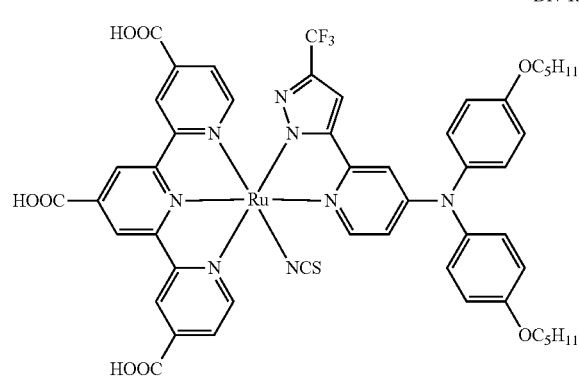
DN-21
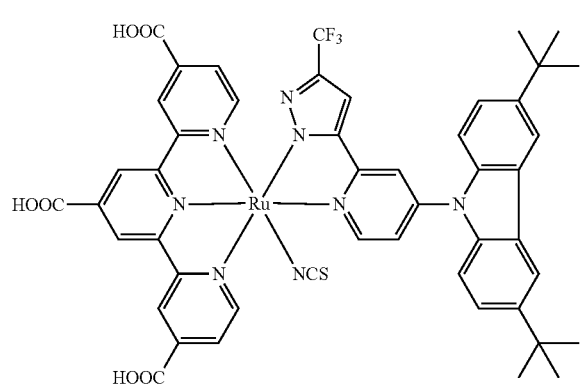
-continued
DN-22
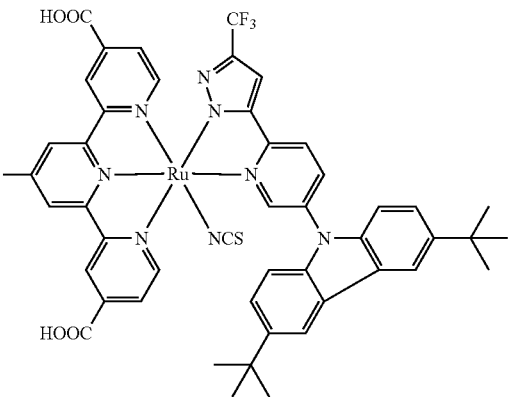
DA-1
DA-2
(Synthesis of Example Metal Complex Dye DN-1)
According to a method of the following scheme, a compound (45) was synthesized, and an example metal complex dye DN-1 was synthesized.

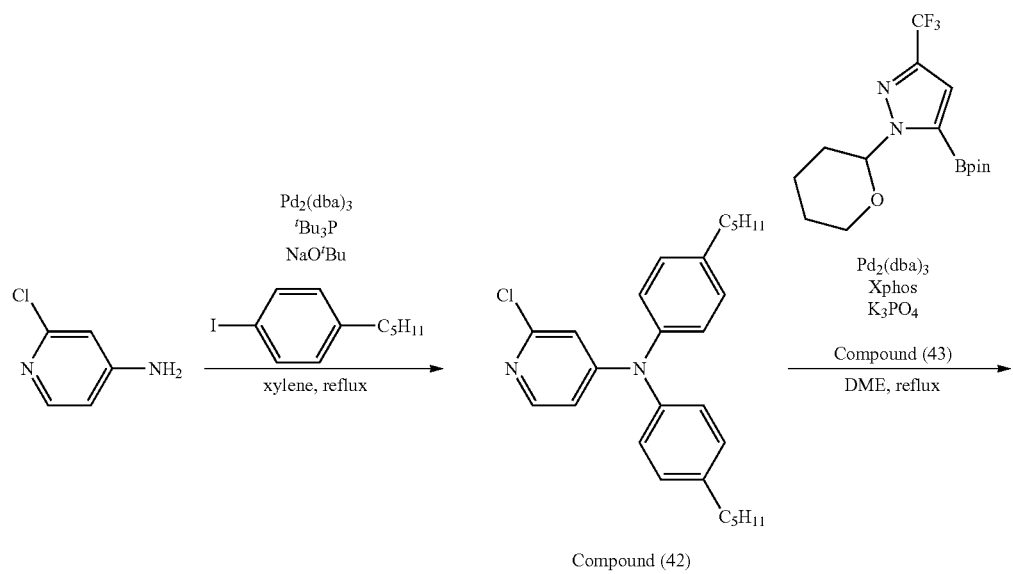
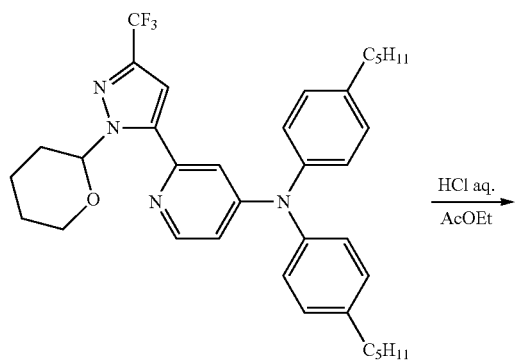
Compound (44)
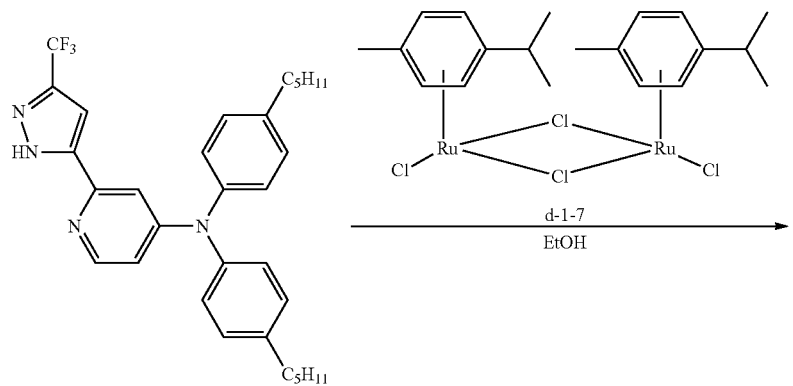
Compound (45)

-continued
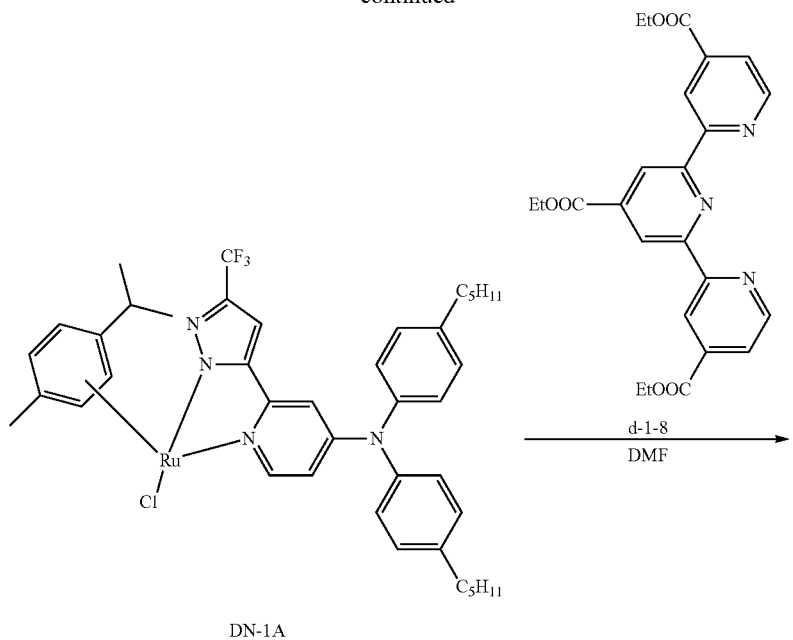
DN-1A
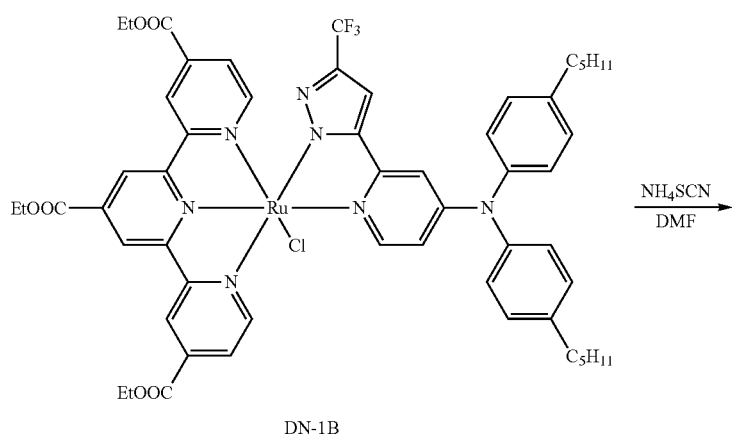
DN-1B
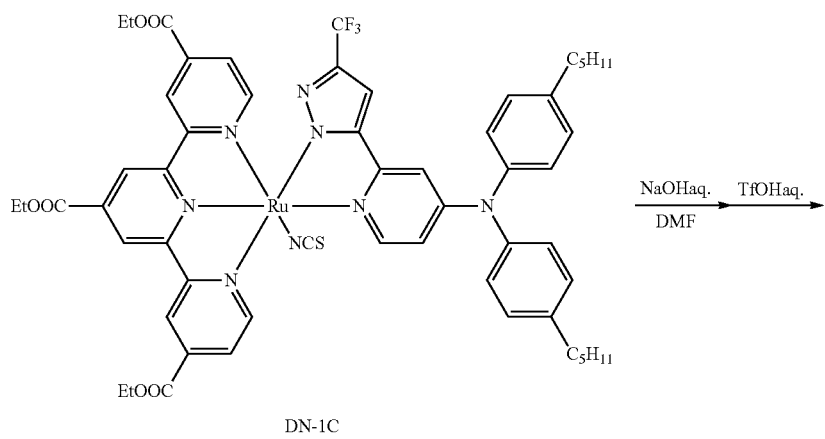
DN-1C

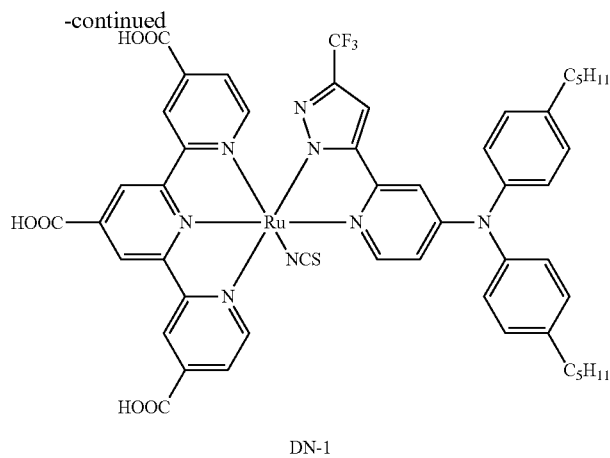

DN-1

(i) Synthesis of Compound (42)

2.47 g of sodium-tert-butoxide, 25 ml of xylene, 1.5 g of 4-amino-2-chloropyridine, and 9.60 g of 4-iodopentylbenzene were put into a three-neck flask, and nitrogen purging was performed. While the resultant was being stirred, 0.534 g of tris(dibenzylideneacetone)dipalladium (0) and 0.472 g of tri-tert-butylphosphine were added thereto, and the resultant was heated under reflux for 2 hours. After the resultant was returned to room temperature, ice water and ethyl acetate were added thereto, and an organic layer was concentrated under reduced pressure. The resultant was purified by silica gel column chromatography using hexane/ethyl acetate as an eluant, thereby obtaining 3.7 g of a compound (42).

(ii) Synthesis of Compound (44)

2.66 g of a compound (43), which was synthesized according to the method described in J. Org. Chem., 2008, 73, p. 4309-4312, 2.70 g of the compound (42), 5.45 g of potassium triphosphate, and 54 ml of 1,2-dimethoxyethane were put into a three-neck flask, and nitrogen purging was performed. While the resultant was being stirred, 0.54 g of Xphos G3 was added thereto, and the resultant was heated under reflux for 3 hours. After being returned to room temperature, the resultant was subjected to filtration using celite, and the solvent was distilled away under reduced pressure. Thereafter, the resultant was purified by silica gel column chromatography using hexane/ethyl acetate as an eluant, thereby obtaining 1.82 g of a compound (44).

(iii) Synthesis of Compound (45)

1.70 g of the compound (44) and 28 ml of a hydrochloric acid/ethyl acetate solution were put into a three-neck flask, and the resultant was stirred for 1 hour. Thereafter, sodium bicarbonate water was added thereto so as to perform liquid separation, and an organic layer was concentrated. The resultant was subjected to pressure reduction at 140° C., thereby obtaining 3.7 g of a compound (45).

(iv) Synthesis of Metal Complex DN-1A 2.94 g of [Ru(p-cymene)Cl$_2$]$_2$ and 5.00 g of the compound (45) were added to 192 ml of ethanol, and the resultant was heated under reflux for 3 hours. Thereafter, the solvent was distilled away under reduced pressure, liquid separation was performed by using ethyl acetate and sodium bicarbonate water, and an organic layer was concentrated. The resultant was thoroughly dissolved in acetonitrile by heating, concentrated until the amount thereof became about 20 ml, and then left to cool such that precipitation occurred. The resultant was then filtered, washed with acetonitrile, and dried, thereby obtaining 4.93 g of a metal complex DN-1A.

(v) Synthesis of Metal Complex DN-1B 0.8 g of the metal complex DN-1A, 0.455 g of a compound d-1-8, and 10 ml of N,N-dimethylformamide (DMF) were put into a 100 ml three-neck flask, and the resultant was heated under reflux. After the reaction ended, the solvent was distilled away under reduced pressure, and the resultant was purified by silica gel column chromatography using methylene chloride/ethyl acetate as an eluant, thereby obtaining 0.5 g of a metal complex DN-1B.

(vi) Synthesis of Metal Complex DN-1C 0.26 g of the metal complex DN-1B, 179 mg of NH$_4$SCN, and 4 ml of DMF were put into a 100 ml three-neck flask, and the resultant was heated and stirred for 5 hours at 130° C. After the reaction ended, the solvent was distilled away under reduced pressure, and the resultant was purified by silica gel column chromatography using methylene chloride/ethyl acetate as an eluant, thereby obtaining 90 mg of a metal complex DN-1C.

(vii) Synthesis of Metal Complex Dye DN-1

90 mg of the metal complex DN-1C and 30 ml of DMF were put into a 100 ml three-neck flask. While the resultant was being stirred at room temperature, an aqueous solution of 1 N sodium hydroxide was added dropwise thereto, and the resultant was stirred for 1 hour. Subsequently, a methanol solution of trifluoromethanesulfonic acid and water were added thereto, and the obtained precipitate was filtered, washed with water, and dried, thereby obtaining 77 mg of a metal complex dye DN-1. The obtained compound was identified by MS analysis.

Figure 3:
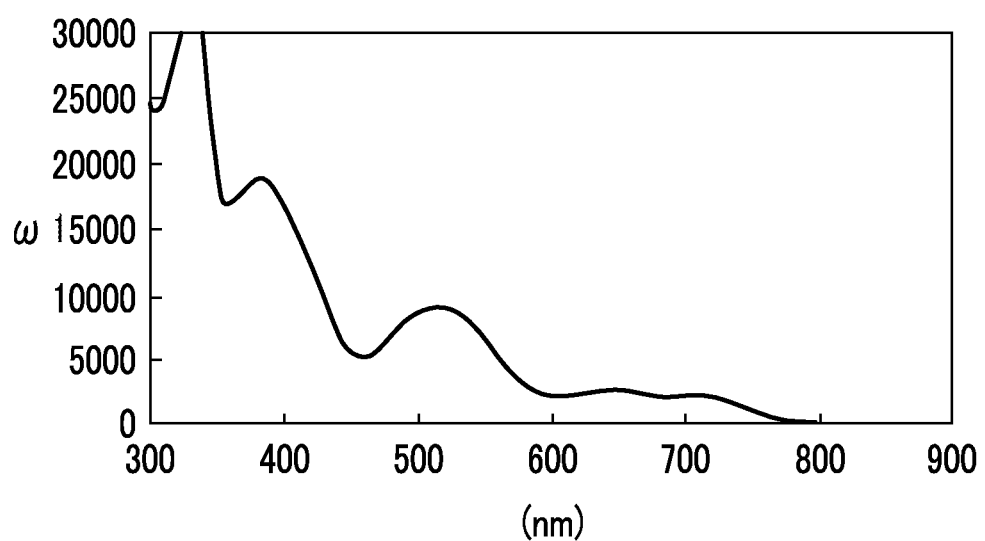
FIG. 3 is a view showing a visible absorption spectrum of a metal complex dye DN-1, which is synthesized in Examples, in a TBAOH/methanol solvent.
Figure 4:
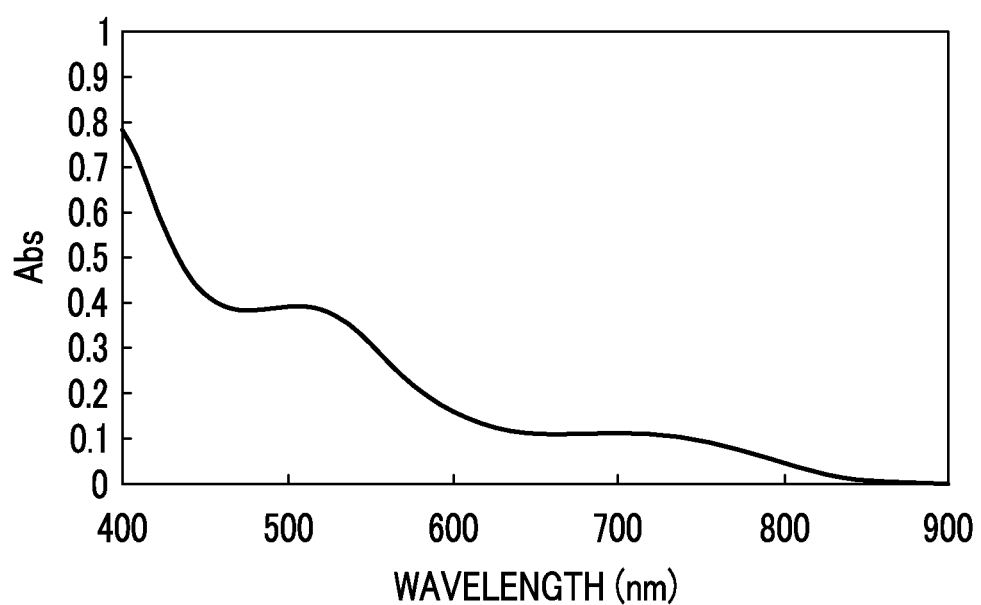
FIG. 4 is a view showing a visible absorption spectrum in a titanium oxide film obtained by causing the metal complex dye DN-1, which is synthesized in Examples, to be adsorbed onto titanium oxide.

FIGS. 3 and 4 show visible absorption spectra of the metal complex dye DN-1.

The visible absorption spectrum of the metal complex dye DN-1 was measured by using UV-3600 manufactured by Shimadzu Corporation by setting the concentration of the metal complex dye DN-1 to be 17 μmol/L.

FIG. 3 is a view showing a spectrum in a methanol solution of 340 mmol/L tetrabutylammonium hydroxide (TBAOH).

FIG. 4 shows a visible absorption spectrum in a model semiconductor film (titanium oxide film onto which the metal complex dye DN-1 was adsorbed) based on a sample No. 101 in Example 1 which will be described later.

(Synthesis of Example Metal Complex Dyes DN-2, DN-13, DN-21, DN-22, DA-1, and DA-2)

In the same manner as used for the example metal complex dye DN-1, example metal complex dyes DN-2, DN-13, DN-21, DN-22, DA-1, and DA-2 were synthesized. The obtained compounds were identified by MS analysis.

The structure of each of the metal complex dyes was checked by mass spectroscopy (MS) analysis.

In the following Table 1, the results of MS analysis performed on the metal complex dyes are summarized.

TABLE 1

| Metal complex dye | ESI-MS |
| --- | --- |
| DN-1 | MS-ESI m/z = 1044.2 (M + H)$^+$ |
| DN-2 | MS-ESI m/z = 1044.2 (M + H)$^+$ |
| DN-13 | MS-ESI m/z = 1076.2 (M + H)$^+$ |
| DN-21 | MS-ESI m/z = 1014.2 (M + H)$^+$ |
| DN-22 | MS-ESI m/z = 1014.2 (M + H)$^+$ |
| DA-1 | MS-ESI m/z = 1092.2 (M + H)$^+$ |
| DA-2 | MS-ESI m/z = 1092.2 (M + H)$^+$ |

Example 1

(Preparation of Dye-sensitized Solar Cell)

For forming a semiconductor layer or a light scattering layer of a semiconductor electrode constituting a photoelectrode, the following pastes were prepared. By using the pastes, dye-sensitized solar cells were prepared.

[Preparation of Paste]

(Paste A)

Spherical $TiO_2$ particles (anatase; mean particle size: 25 nm; hereinafter, referred to as "spherical $TiO_2$ particles A") were added to a nitric acid solution, and the solution was stirred, thereby preparing a titania slurry. Thereafter, as a thickener, a cellulose-based binder was added to the titania slurry, and the resultant was kneaded, thereby preparing a paste A.

(Paste 1)

The spherical $TiO_2$ particles A and spherical $TiO_2$ particles (anatase; mean particle size: 200 nm; hereinafter, referred to as "spherical $TiO_2$ particles B") were added to a nitric acid solution, and the solution was stirred, thereby preparing a titania slurry. Thereafter, as a thickener, a cellulose-based binder was added to the titania slurry, and the resultant was kneaded, thereby preparing a paste 1 (mass of $TiO_2$ particles A:mass of $TiO_2$ particles B=30:70).

(Paste 2)

The paste A was mixed with rod-like $TiO_2$ particles (anatase; diameter: 100 nm; aspect ratio: 5; hereinafter, referred to as "rod-like $TiO_2$ particles C"), thereby preparing a paste 2 (mass of rod-like $TiO_2$ particles C:mass of paste A=30:70).

[Preparation of Photoelectrode]

Figure 2:
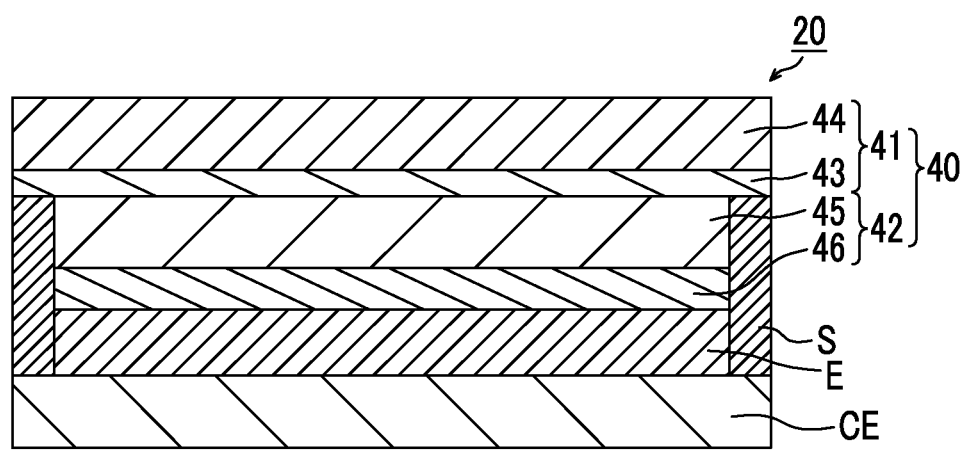
FIG. 2 is a cross-sectional view schematically showing a dye-sensitized solar cell prepared in Examples.

According to the following procedure, a photoelectrode was prepared which had the same constitution as that of the photoelectrode 12 shown in FIG. 5 described in JP2002-289274A. Furthermore, by using the photoelectrode, a 10 mm×10 mm dye-sensitized solar cell 1 was prepared which had the same constitution as that of the dye-sensitized solar cell 20 except for the photoelectrode shown in FIG. 3 described in the same document. The specific constitution thereof is shown in FIG. 2 included in the present application. The dye-sensitized solar cell 20 has a transparent electrode 41, a semiconductor electrode 42, a transparent conductive film 43, a substrate 44, a semiconductor layer 45, a light scattering layer 46, a photoelectrode 40, a counter electrode CE, an electrolyte E, and a spacer S.

A fluorine-doped $SnO_2$ conductive film (film thickness: 500 nm) was formed on a glass substrate, thereby preparing a transparent electrode. Thereafter, the paste 1 was screen-printed on the $SnO_2$ conductive film and then dried. Then the resultant was fired under a condition of 450° C. in the air. In addition, the screen printing and firing were repeated by using the paste 2. In this way, a semiconductor electrode A (area of light-receiving surface: 10 mm×10 mm; layer thickness: 17 µm; thickness of the dye-adsorbed layer: 12 µm; thickness of the light scattering layer: 5 µm; amount of the rod-like $TiO_2$ particles C contained in the light-scattering layer: 30% by mass) having the same constitution as that of the semiconductor electrode 42 shown in FIG. 2 included in the present application was formed on the $SnO_2$ conductive film, thereby preparing a photoelectrode A not containing a sensitizing dye.

[Dye Adsorption]

Subsequently, in the following manner, a dye was adsorbed onto the photoelectrode A (precursor of a dye-adsorbed electrode) prepared as above. First, a mixture consisting of anhydrous tert-butanol, which was dehydrated over magnesium ethoxide, and dimethylformamide at a ratio of 1:1 (volume ratio) was used as a solvent, and the metal complex dyes listed in the following Table 2 were dissolved in the solvent such that the concentration thereof became $3×10^{-4}$ mol/L. Furthermore, as a coadsorbent, an equimolar mixture of chenodeoxycholic acid and cholic acid was added to the solution, in an amount of 20 mol with respect to 1 mol of each of the metal complex dyes, thereby preparing dye solutions. As a result of measuring the water content in the dye solutions by Karl Fischer titration, it was confirmed that the water content was less than 0.01% by mass. Thereafter, the semiconductor electrode was dipped in each of the dye solutions under conditions of 10 hours at 40° C., pulled up, and then dried at 50° C. In this way, photoelectrodes 40 were completed in which the dye was adsorbed onto the semiconductor electrode in an amount of about $2×10^{-7}$ mol/cm$^2$.

[Preparation of Dye-Sensitized Solar Cell]

Then, as a counter electrode, a platinum electrode (thickness of thin Pt film: 100 nm) having the same size and shape as those of the photoelectrode 40 was prepared. Furthermore, as the electrolyte E, a iodine-based redox solution containing 0.1 M of iodine, 0.1 M of lithium iodide, and 0.6 M of 1-propyl-3-methylimidazolium iodide and 4-tert-butylpyridine was prepared. In addition, a spacer S (trade name: "Surlyn") manufactured by DuPont having a shape matching the size of the semiconductor electrode was prepared. Thereafter, the photoelectrode 40 and the counter electrode CE were caused to face each other across the spacer S as shown in FIG. 3 described in JP2002-289274A, and the inside thereof was filled with the electrolyte E. In this way, a dye-sensitized solar cell (cell A) composed of the photoelectric conversion element using the photoelectrode A was completed.

<Photoelectric Conversion Efficiency (η/%)>

By performing a cell characteristic test, the photoelectric conversion efficiency (η/%) of each of the dye-sensitized solar cells was measured. During the cell characteristic test, by using a solar simulator (WXS-85H manufactured by WACOM ELECTRIC CO., LTD.), the dye-sensitized solar cell was irradiated with pseudo-solar light at 1,000 W/m$^2$ from a xenon lamp through an AM 1.5 filter. By using an IV tester, the current-voltage characteristics were measured, and the photoelectric conversion efficiency (η/%) was determined. The photoelectric conversion efficiency of each of the dye-sensitized solar cells was evaluated by being ranked based on the photoelectric conversion efficiency of the following comparative compound S-3.

The photoelectric conversion efficiency ranked B or higher level is an allowable level (passing level).

Evaluation Rank

AA: The photoelectric conversion efficiency is not less than 1.15 times the photoelectric conversion efficiency of the comparative compound S-3.

A: The photoelectric conversion efficiency is not less than 1.1 times the photoelectric conversion efficiency of the comparative compound S-3 but less than 1.15 times the photoelectric conversion efficiency of the comparative compound S-3.

B: The photoelectric conversion efficiency is not less than 1.03 times the photoelectric conversion efficiency of the comparative compound S-3 but less than 1.1 times the photoelectric conversion efficiency of the comparative compound S-3.
C: The photoelectric conversion efficiency is less than 1.03 times the photoelectric conversion efficiency of the comparative compound S-3.

<Evaluation of Thermal Deterioration>

Each of the prepared dye-sensitized solar cells was put into a thermostatic bath at 40° C. so as to perform a heat resistance test. The current of the dye-sensitized solar cells having not yet been subjected to the heat resistance test and the current of the dye-sensitized solar cells 12 hours after the heat resistance test were evaluated. The "decrement of the current value after the heat resistance test" was divided by the "current value before the heat resistance test", and the obtained value was multiplied by 100. The value obtained in this way was calculated as a thermal deterioration rate. The thermal deterioration rate of each of the dye-sensitized solar cells was evaluated by being ranked based on the thermal deterioration rate obtained from the following comparative compound S-3. In the following Table 2, "thermal deterioration" indicates the thermal deterioration rate.

Evaluation Rank
A: The thermal deterioration rate is less than 0.9 times the thermal deterioration rate of the comparative compound S-3.
B: The thermal deterioration rate is equal to or greater than 0.9 times the thermal deterioration rate of the comparative compound S-3 but less than 1 time the thermal deterioration rate of the comparative compound S-3.
C: The thermal deterioration rate is equal to or greater than 1 time the thermal deterioration rate of the comparative compound S-3.

<Heat Cycle Test>

Each of the prepared dye-sensitized solar cells was repeatedly cooled and heated by being alternately put into a freezer at −10° C. and a thermostatic bath at 40° C. every two hours, thereby performing a heat cycle test. The current of the dye-sensitized solar cell having not yet been subjected to the heat cycle test and the current of the dye-sensitized solar cell 24 hours after the heat cycle test were evaluated. The "decrement of the current value after the heat resistance test" was divided by the "current value before the heat resistance test", and the obtained value was multiplied by 100. The value obtained in this way was calculated as a deterioration rate. The deterioration rate of each of the dye-sensitized solar cells was evaluated by being ranked based on the deterioration rate of the following comparative compound S-3. In the following Table 2, "heat cycle" indicates the deterioration rate.

Evaluation Rank
A: The deterioration rate is less than 0.9 times the deterioration rate of the comparative compound S-3.
B: The deterioration rate is equal to or greater than 0.9 times the deterioration rate of the comparative compound S-3 but less than 1 time the deterioration rate of the comparative compound S-3.
C: The deterioration rate is equal to or greater than 1 time the deterioration rate of the comparative compound S-3.

The obtained results are summarized in the following Table 2.

TABLE 2

| Sample No. | Metal complex dye | Photoelectric conversion efficiency | Thermal deterioration | Heat cycle | Note |
| --- | --- | --- | --- | --- | --- |
| 101 | DN-1 | AA | A | A | Present invention |
| 102 | DN-2 | AA | A | A | Present invention |
| 103 | DN-13 | AA | A | A | Present invention |
| 104 | DN-21 | AA | A | A | Present invention |
| 105 | DN-22 | AA | A | A | Present invention |
| 106 | DA-1 | AA | A | A | Present invention |
| 107 | DA-2 | AA | A | A | Present invention |
| C11 | S-1 | C | C | C | Comparative example |
| C12 | S-2 | C | C | C | Comparative example |
| C13 | S-3 | C | C | C | Comparative example |
| C14 | S-4 | C | C | C | Comparative example |
| C15 | S-5 | C | C | C | Comparative example |

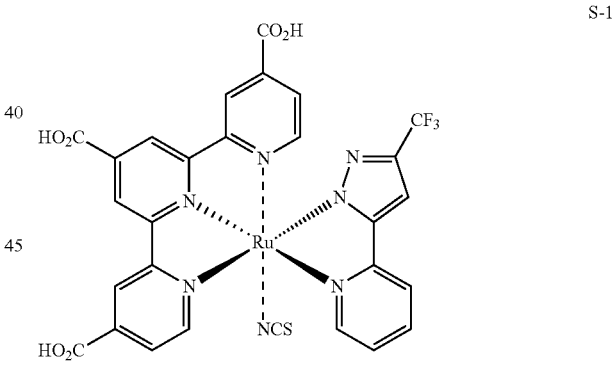

S-1

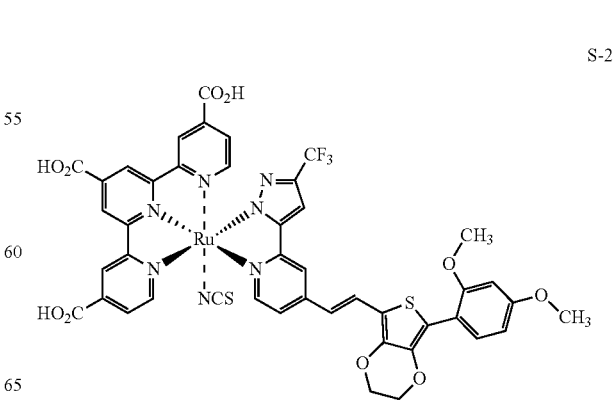

S-2

-continued

S-3

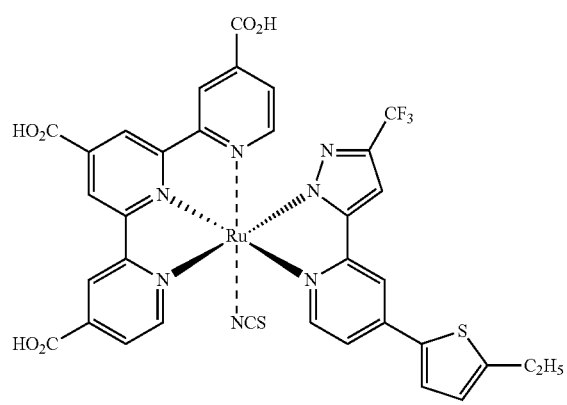

S-4

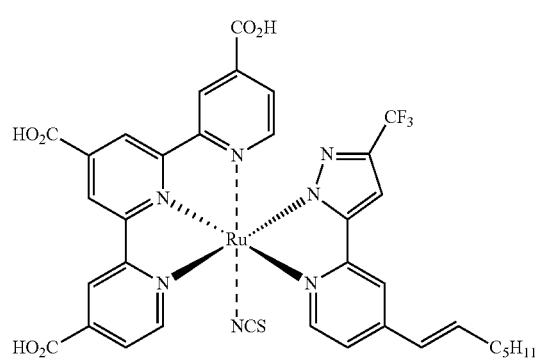

-continued

S-5

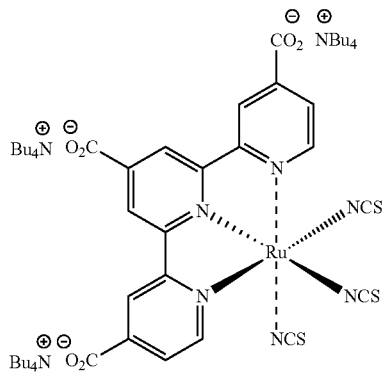

From Table 2, it is understood that the metal complex dye of the present invention has high photoelectric conversion efficiency and is excellent in durability such as thermal deterioration or heat cycle properties.

<<Second Embodiment>>
<Synthesis of Metal Complex Dye>

Hereinafter, synthesis methods of dyes of the second embodiment will be specifically described by using examples. However, the starting material, dye intermediate, and synthesis route are not limited to the following methods.

First, the following example metal complex dye was synthesized.

(Synthesis of Example Metal Complex Dye D-1-5a)

According to the method of the following scheme, an example metal complex dye D-1-5a was synthesized.

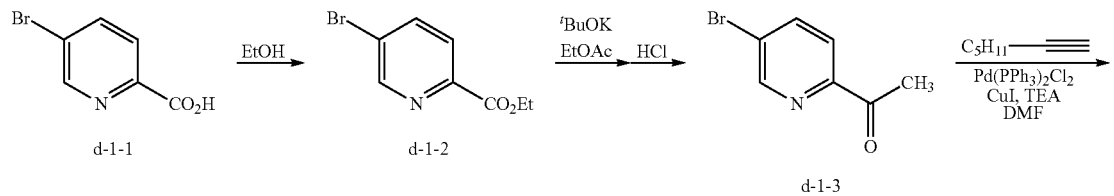

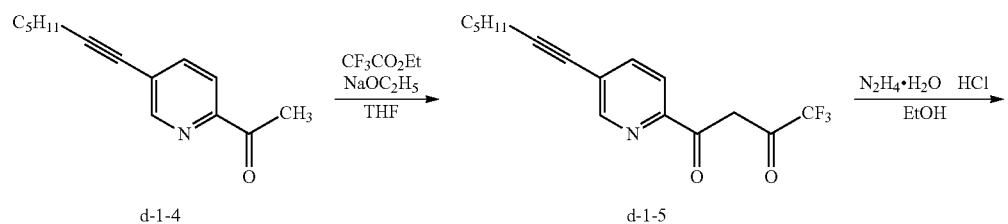

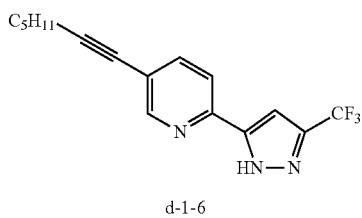

-continued

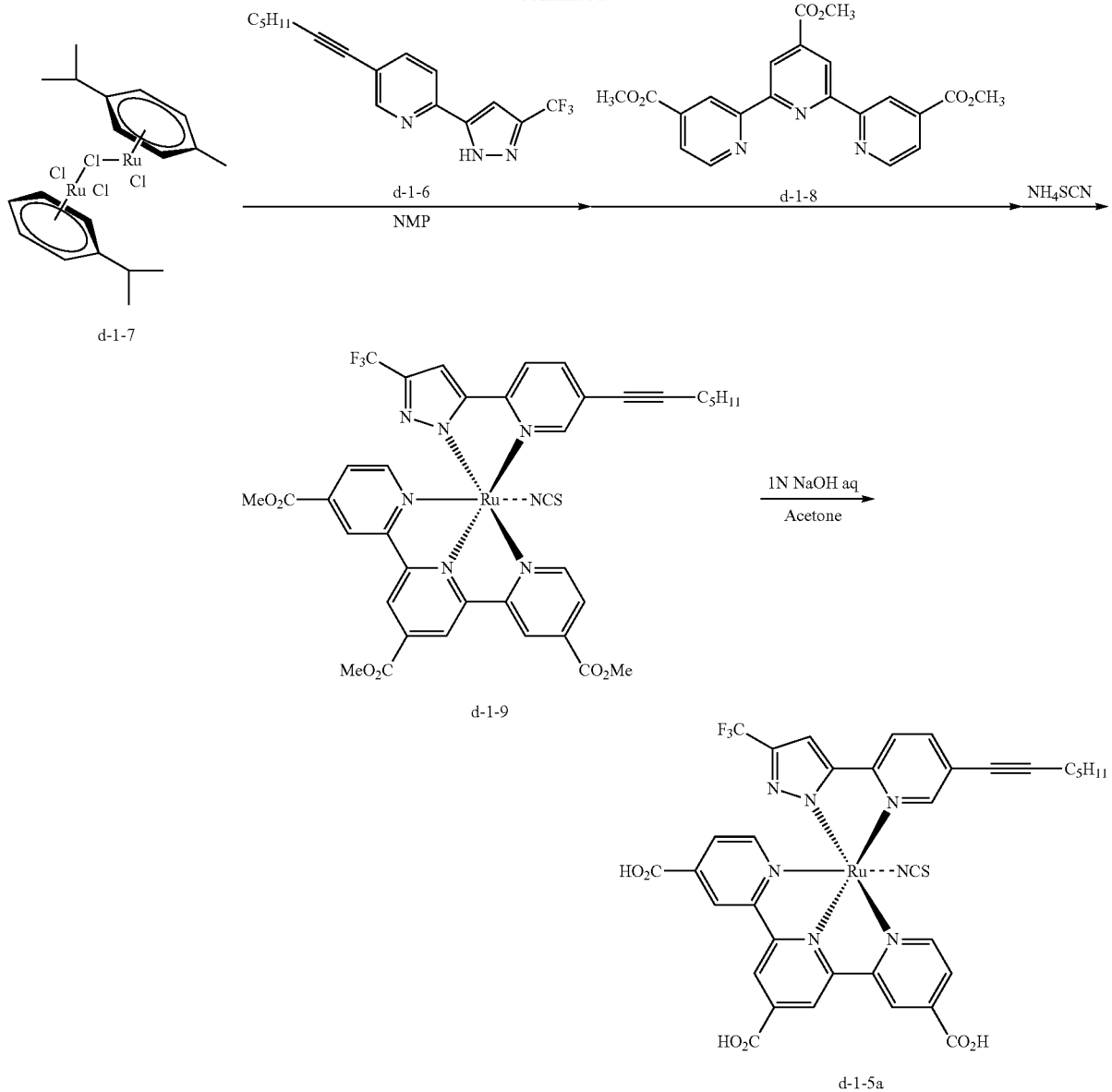

(i) Synthesis of Compound d-1-2

21 g of a compound d-1-1 was dissolved in 300 ml of EtOH (ethanol), 15 ml of sulfuric acid was added thereto, and the resultant was stirred for 3 hours at 70° C. Thereafter, the obtained solution was cooled and neutralized by using sodium bicarbonate water, then ethyl acetate was added thereto so as to perform liquid separation and extraction, and an organic layer was concentrated. The obtained concentrate was purified by silica gel column chromatography, thereby obtaining 15 g of a compound d-1-2.

(ii) Synthesis of Compound d-1-3

19 g of the compound d-1-2 and 8.5 g of ethyl acetate were put into 100 ml of toluene, and the resultant was mixed in a nitrogen atmosphere. After the obtained solution was cooled in an ice bath, 18 g of t-BuOK was added thereto in several batches, and the resultant was stirred for 3 hours. The resultant was neutralized by using 1 N aqueous hydrochloric acid, ethyl acetate was then added thereto so as to perform liquid separation and extraction, and an organic layer was concentrated. The obtained concentrate was put into 200 ml of 2 N aqueous hydrochloric acid, and the resultant was heated for 12 hours at an external temperature of 100° C. After being cooled, the obtained solution was neutralized by using sodium bicarbonate water, ethyl acetate was added thereto so as to perform liquid separation and extraction, and an organic layer was concentrated. The obtained concentrate was purified by silica gel column chromatography, thereby obtaining 10.5 g of a compound d-1-3.

(iii) Synthesis of Compound d-1-4

In 30 ml of a dimethylformamide (DMF) solvent, 0.05 equivalents of CuI, 0.05 equivalents of $Pd(PPh_3)_2Cl_2$, 1.4 g of 1-heptene, and 4 equivalents of triethylamine were added to 2.2 g of the compound d-1-3, and the resultant was stirred for 3 hours at room temperature in a nitrogen atmosphere. 1 N hydrochloric acid and ethyl acetate were added to the obtained solution so as to perform liquid separation and extraction, and an organic layer was concentrated. The obtained concentrate was purified by silica gel column chromatography, thereby obtaining 1.8 g of a compound d-1-4.

(iv) Synthesis of Compound d-1-5

1.5 g of the compound d-1-4 was dissolved in 20 ml of tetrahydrofuran (THF). While the resultant was being stirred at 0° C. in a nitrogen atmosphere, 2.2 equivalents of sodium ethoxide was added thereto, and then the resultant was stirred for 15 minutes. Subsequently, 1.1 equivalents of ethyl trifluoroacetate was added dropwise to the obtained solution, and the resultant was stirred for 20 hours at an external temperature of 70° C. After the obtained solution was returned to room temperature, an aqueous ammonium chloride was added dropwise thereto so as to perform liquid separation, and an organic layer was concentrated, thereby obtaining 1.3 g of a crude purified compound d-1-5.

(v) Synthesis of Compound d-1-6

1.3 g of the compound d-1-5 was dissolved in 20 ml of ethanol. While the resultant was being stirred at room temperature in a nitrogen atmosphere, 1.0 equivalent of hydrazine monohydrate was added thereto, and the resultant was heated for 12 hours at an external temperature of 90° C. Thereafter, 0.5 ml of concentrated hydrochloric acid was added to the obtained solution, and the solution was stirred for 1 hour. After the obtained solution was concentrated, extraction and liquid separation were performed by using sodium bicarbonate water and ethyl acetate, and an organic layer was concentrated. The obtained concentrate was purified by silica gel column chromatography, thereby obtaining 1.3 g of a compound d-1-6.

(vi) Synthesis of Example Metal Complex Dye D-1-5a 1.3 g of the compound d-1-6 and 1 equivalent of a compound d-1-7 were added to 150 ml of N-methylpyrrolidone (NMP), and the resultant was stirred for 3 hours at 70° C. in a nitrogen atmosphere. Thereafter, 1 equivalent of a compound d-1-8 was added thereto, and the resultant was heated and stirred for 8 hours at 160° C. Then, 10 equivalents of ammonium thiocyanate was added thereto, and the resultant was stirred for 8 hours at 160° C. After the obtained solution was concentrated, water was added thereto, and the resultant was filtered. The filtrate was purified by silica gel column chromatography, thereby obtaining a compound d-1-9. Subsequently, the compound was added to a solvent mixture of 30 ml of acetone and 40 ml of an aqueous solution of 1 N sodium hydroxide, and the resultant was stirred for 24 hours at an external temperature of 65° C. The resultant was returned to room temperature, and the pH thereof was adjusted to be 3 by using hydrochloric acid, and the precipitate was filtered, thereby obtaining 2.5 g of a crude purified substance D-1-5a.

The substance D-1-5a and tetrabutylammonium hydroxide (TBAOH) were dissolved in a methanol solution, and the resultant was purified by using a column of Sephadex LH-20. The fraction of a main layer was collected from the resultant and concentrated, and then a 0.1 M solution of trifluoromethane sulfonic acid was added thereto so as to adjust the pH thereof to be 3. The precipitate was filtered, thereby obtaining 2.0 g of an example metal complex dye D-1-5a.

The structure of the obtained example metal complex dye D-1-5a was checked by mass spectroscopy (MS) analysis. ESI-MS m/z=832.1 (M+H)$^+$ Other example metal complex dyes can also be synthesized by combining the aforementioned synthesis method with various coupling reactions and the like. The following example metal complex dyes were synthesized in the same manner as used for the example metal complex dye D-1-5a.

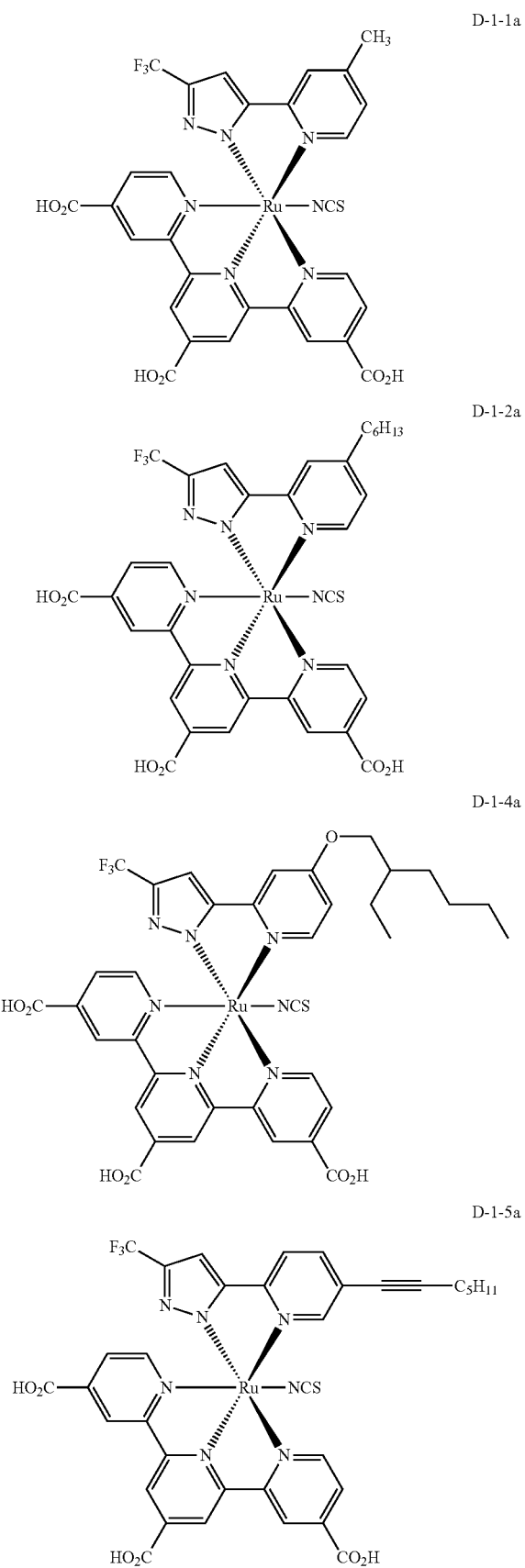

-continued
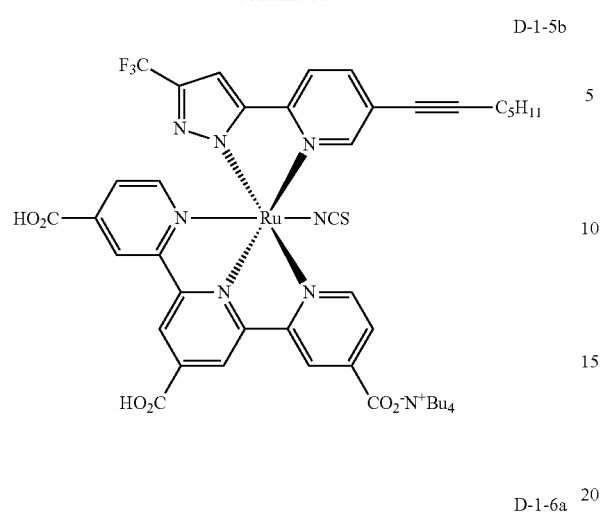
D-1-5b
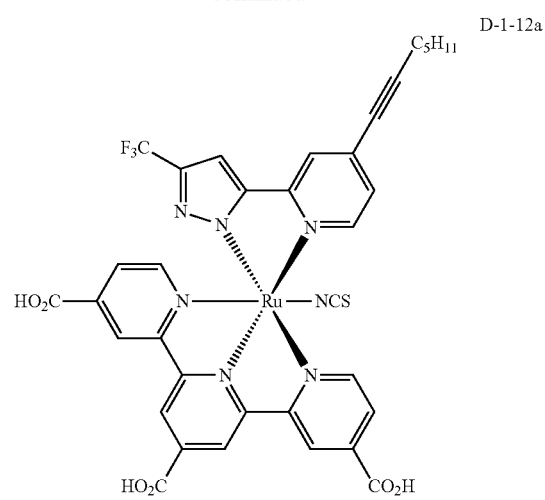
D-1-12a
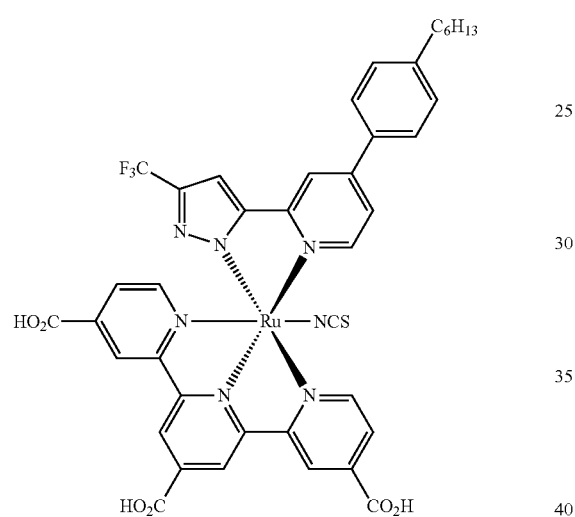
D-1-6a
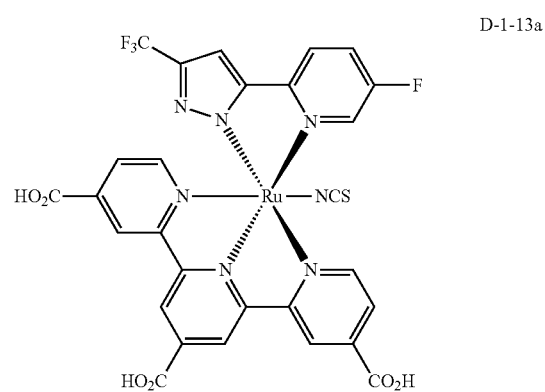
D-1-13a
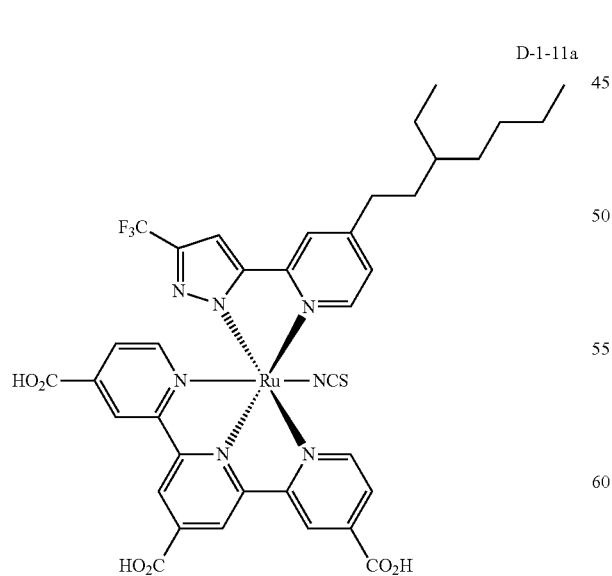
D-1-11a
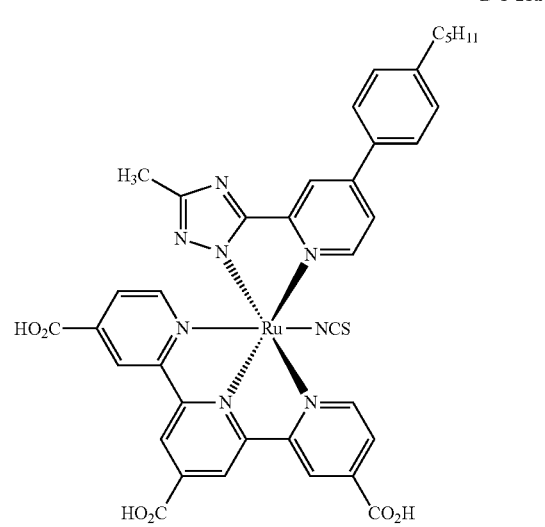
D-1-21a

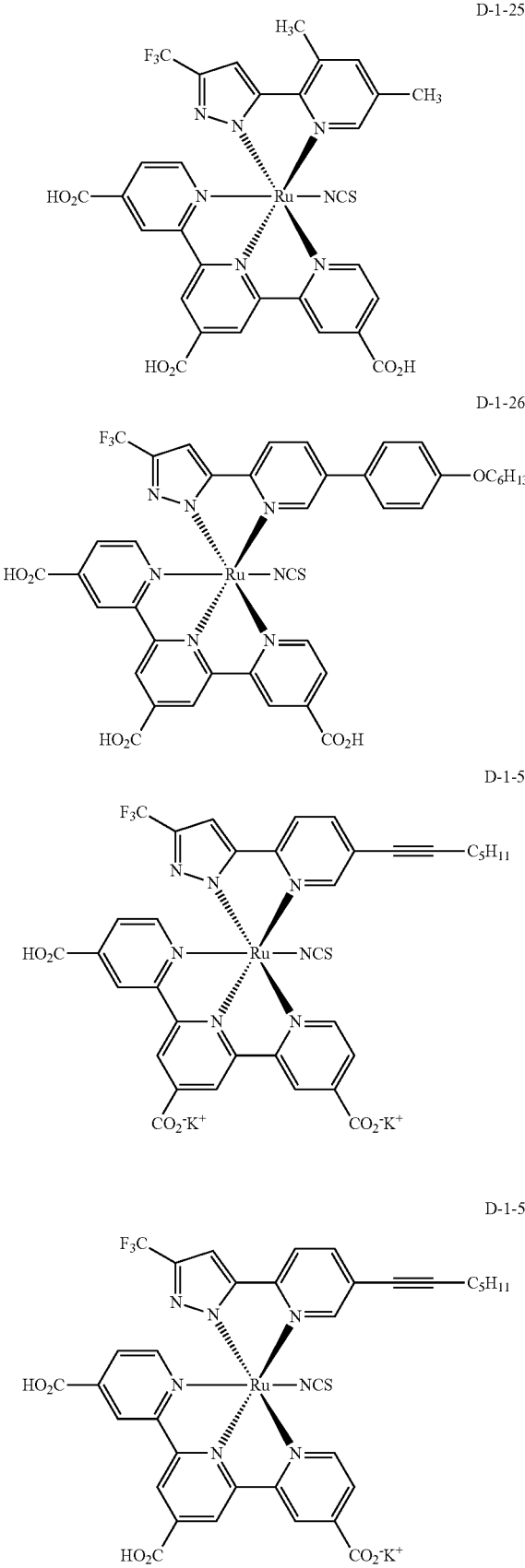

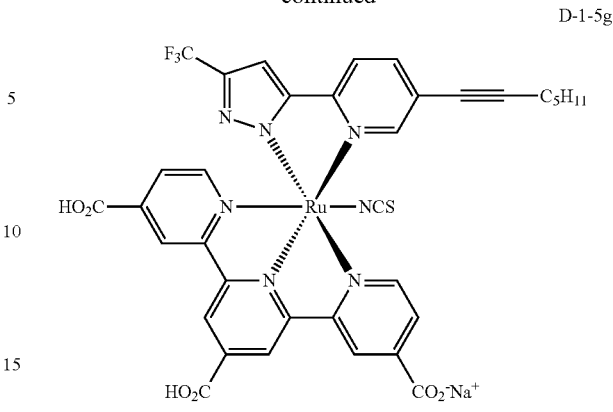

The structure of each of the metal complex dyes was checked by MS analysis and $^1$H-NMR.

The results of the MS analysis of the metal complex dyes are summarized in the following Table 3.

TABLE 3

| Metal complex dye | ESI-MS |
| --- | --- |
| D-1-1a | ESI-MS m/z = 752.0 (M + H)$^+$ |
| D-1-2a | ESI-MS m/z = 822.0 (M + H)$^+$ |
| D-1-4a | ESI-MS m/z = 866.1 (M + H)$^+$ |
| D-1-5a | ESI-MS m/z = 832.1 (M + H)$^+$ |
| D-1-5b | ESI-MS m/z = 832.1 (M + H)$^+$ |
| D-1-6a | ESI-MS m/z = 898.1 (M + H)$^+$ |
| D-1-11a | ESI-MS m/z = 864.1 (M + H)$^+$ |
| D-1-12a | ESI-MS m/z = 832.1 (M + H)$^+$ |
| D-1-13a | ESI-MS m/z = 756.0 (M + H)$^+$ |
| D-1-21a | ESI-MS m/z = 831.1 (M + H)$^+$ |
| D-1-25a | ESI-MS m/z = 766.0 (M + H)$^+$ |
| D-1-26a | ESI-MS m/z = 914.1 (M + H)$^+$ |

Example 2

(Preparation of Dye-sensitized Solar Cell)

In order to form a semiconductor layer or a light scattering layer of a semiconductor electrode constituting a photoelectrode, the following pastes were prepared. By using the pastes, dye-sensitized solar cells were prepared.

[Preparation of Paste]

(Paste A)

Spherical TiO$_2$ particles (anatase; mean particle size: 25 nm; hereinafter, referred to as "spherical TiO$_2$ particles A") were added to a nitric acid solution, and the solution was stirred, thereby preparing a titania slurry. Thereafter, as a thickener, a cellulose-based binder was added to the titania slurry, and the resultant was kneaded, thereby preparing a paste A.

(Paste 1)

The spherical TiO$_2$ particles A and spherical TiO$_2$ particles (anatase; mean particle size: 200 nm; hereinafter, referred to as "spherical TiO$_2$ particles B") were added to a nitric acid solution, and the solution was stirred, thereby preparing a titania slurry. Thereafter, as a thickener, a cellulose-based binder was added to the titania slurry, and the resultant was kneaded, thereby preparing a paste 1 (mass of TiO$_2$ particles A:mass of TiO$_2$ particles B=30:70).

(Paste 2)

The paste A was mixed with rod-like TiO$_2$ particles (anatase; diameter: 100 nm; aspect ratio: 5; hereinafter, referred to as "rod-like TiO$_2$ particles C"), thereby preparing a paste 2 (mass of rod-like TiO$_2$ particles C:mass of paste A=30:70).

[Preparation of Photoelectrode]

According to the following procedure, a photoelectrode was prepared which had the same constitution as that of the photoelectrode 12 shown in FIG. 5 described in JP2002-289274A. Furthermore, by using the photoelectrode, a 10 mm×10 mm dye-sensitized solar cell was prepared which had the same constitution as that of the dye-sensitized solar cell 20 except for the photoelectrode shown in FIG. 3 described in the same document. The specific constitution of the dye-sensitized solar cell 20 is shown in FIG. 2 included in the present application.

A fluorine-doped $SnO_2$ conductive film (film thickness: 500 nm) was formed on a glass substrate, thereby preparing a transparent electrode. Thereafter, the paste 1 was screen-printed on the $SnO_2$ conductive film and then dried. Then the resultant was fired under a condition of 450° C. in the air. In addition, the screen printing and firing were repeated by using the paste 2. In this way, a semiconductor electrode A (area of light-receiving surface: 10 mm×10 mm; layer thickness: 17 μm; thickness of the dye-adsorbed layer: 12 μm; thickness of the light scattering layer: 5 μm; amount of the rod-like $TiO_2$ particles C contained in the light-scattering layer: 30% by mass) having the same constitution as that of the semiconductor electrode 42 shown in FIG. 2 included in the present application was formed on the $SnO_2$ conductive film, thereby preparing a photoelectrode A not containing a sensitizing dye.

[Dye Adsorption]

Subsequently, in the following manner, a dye was adsorbed onto the photoelectrode A (precursor of a dye-adsorbed electrode) prepared as above. First, a mixture consisting of anhydrous butanol, which was dehydrated over magnesium ethoxide, and dimethylformamide at a ratio of 1:1 (volume ratio) was used as a solvent, and the metal complex dyes listed in the following Table 4 were dissolved in the solvent such that the concentration thereof became $3 \times 10^{-4}$ mol/L. Furthermore, as a coadsorbent, an equimolar mixture of chenodeoxycholic acid and cholic acid was added to the solution, in an amount of 20 mol with respect to 1 mol of each of the metal complex dyes, thereby preparing dye solutions. As a result of measuring the water content in the dye solutions by Karl Fischer titration, it was confirmed that the water content was less than 0.01% by mass. Thereafter, the semiconductor electrode was dipped in each of the dye solutions under conditions of 10 hours at 40° C., pulled up, and then dried at 50° C. In this way, photoelectrodes 40 were completed in which the dye was adsorbed onto the semiconductor electrode in an amount of about $2 \times 10^{-7}$ mol/cm$^2$.

[Preparation of Dye-sensitized Solar Cell]

Then, as a counter electrode, a platinum electrode (thickness of thin Pt film: 100 nm) having the same size and shape as those of the photoelectrode 40 was prepared. Furthermore, as the electrolyte E, a iodine-based redox solution containing 0.05 M of iodine, 0.01 M of lithium iodide, and 0.6 M of 1-propyl-3-methylimidazolium iodide and 4-tert-butylpyridine was prepared. In addition, a spacer S (trade name: "Surlyn") manufactured by DuPont having a shape matching the size of the semiconductor electrode was prepared. Thereafter, the photoelectrode 40 and the counter electrode CE were caused to face each other across the spacer S as shown in FIG. 3 described in JP2002-289274A, and the inside thereof was filled with the electrolyte E. In this way, a dye-sensitized solar cell (cell A) composed of the photoelectric conversion element using the photoelectrode A was completed.

1) Photoelectric Conversion Efficiency (η/%)

By performing a cell characteristic test, the photoelectric conversion efficiency (η/%) of each of the dye-sensitized solar cells was measured. During the cell characteristic test, by using a solar simulator (WXS-85H manufactured by WACOM ELECTRIC CO., LTD.), the dye-sensitized solar cell was irradiated with pseudo-solar light at 1,000 W/m$^2$ from a xenon lamp through an AM 1. filter. By using an IV tester, the current-voltage characteristics were measured, and the photoelectric conversion efficiency (η/%) was determined. In the following Table 4, initial conversion efficiency indicates the photoelectric conversion efficiency.

The photoelectric conversion efficiency ranked B or higher level is an allowable level (passing level).

Evaluation Criteria

AA: The photoelectric conversion efficiency is equal to or greater than 7.5%.

A: The photoelectric conversion efficiency is equal to or greater than 7.3% but less than 7.5%.

B: The photoelectric conversion efficiency is equal to or greater than 7.0% but less than 7.3%.

C: The photoelectric conversion efficiency is equal to or greater than 6.7% but less than 7.0%.

D: The photoelectric conversion efficiency is equal to or greater than 6.4% but less than 6.7%.

E: The photoelectric conversion efficiency is less than 6.4%.

2) Durability (after Elapse of Time at 80° C. in Dark Place)

After the photoelectric conversion efficiency of the prepared dye-sensitized solar cell was measured, the dye-sensitized solar cell was left in a dark place for 30 hours at 80° C. Thereafter, the photoelectric conversion efficiency of the dye-sensitized solar cell was measured, and a rate (%) of decrease in the photoelectric conversion efficiency was calculated as durability.

The rate (%) of decrease in the photoelectric conversion efficiency was calculated by the following equation.

$$[(\text{Initial efficiency}-\text{efficiency after elapse of time in dark place})/\text{initial efficiency}] \times 100$$

The durability ranked C or a higher level is an allowable level (passing level).

Evaluation Criteria

A: The rate of decrease in the photoelectric conversion efficiency is less than 5.5%.

B: The rate of decrease in the photoelectric conversion efficiency is equal to or greater than 5.5% but less than 7.0%.

C: The rate of decrease in the photoelectric conversion efficiency is equal to or greater than 7.0% but less than 10.0%

D: The rate of decrease in the photoelectric conversion efficiency is equal to or greater than 10.0%.

3) Amount of Dye Adsorbed

By the same method as used in dye adsorption, the dye was adsorbed onto a titanium oxide film having the same area as that of the photoelectrode 40. Thereafter, by using a base (10% tetrabutylammonium hydroxide/methanol solution), the dye was desorbed from the titanium oxide film over 20 hours at 25° C., and a state in which the dye was completely desorbed was checked. Thereafter, the solvent containing the desorbed dye was diluted with methanol, and the absorption of the solution was measured by using UV-3600 (manufactured by Shimadzu Corporation). Based on a calibration curve of solution absorption prepared in advance, the amount of the dye adsorbed was determined.

The determined amount of each of the metal complex dyes adsorbed was divided by the amount of the dye adsorbed that was determined for the comparative compound S-1, thereby obtaining a relative amount of the dye adsorbed.

4) Desorption Test

By using a solution to which water was forcedly added, an adsorption stability test was performed in the following manner.

After the desorption test was performed, the amount of the dye (amount of residual dye) remaining in the titanium oxide film was measured. Specifically, the titanium oxide film to which the dye was adsorbed was dipped in 10 ml of a solution, which was obtained by adding 1% by volume of water to acetonitrile, for 50 hours at 40° C. Thereafter, according to the same procedure as the procedure in 3) Amount of dye adsorbed, the dye was desorbed from the titanium oxide film by using a base (10% tetrabutylammonium hydroxide/methanol solution). Thereafter, the absorption of the solution was measured, and the amount of the dye adsorbed was measured and quantified. As the amount of the dye adsorbed before the desorption test, the value was used which was obtained by desorption and quantification of the dye without performing the desorption test on the titanium oxide film prepared under the same condition. Considering variation, the amount of the residual dye was measured under a condition of n=3, and the average thereof was determined. The average was evaluated based on the following criteria.

The amount of the residual dye ranked B or a higher level is an allowable level (passing level).

Evaluation Criteria (Residual Rate)
A: The residual rate is equal to or greater than 80%.
B: The residual rate is equal to or greater than 70% but less than 80%.
C: The residual rate is equal to or greater than 60% but less than 70%.
D: The residual rate is less than 60%.

5) Dependence on Iodine Concentration

An electrolyte was prepared by changing the concentration of iodine, and the dependence of voltage on the iodine concentration was evaluated.

Specifically, instead of the electrolyte E, an electrolyte was used in which the amount of each of iodine sources (iodine, lithium iodide, and 1-propyl-3-methylimidazolium iodide) was increased and became 1.5 times the amount of the iodine sources in the electrolyte E, and the voltage was measured. The voltage measured in this way was compared to the voltage of the dye-sensitized solar cell using the electrolyte E. Furthermore, a rate of decrease in the voltage was evaluated by being compared with the voltage of the dye-sensitized solar cell using the electrolyte E.

The rate of decrease in voltage ranked B or a higher level is an allowable level (passing level).

Evaluation Criteria (Rate of Decrease in Voltage)
A: The rate of decrease in voltage is less than 2%.
B: The rate of decrease in voltage is equal to or greater than 2% but less than 4%.
C: The rate of decrease in voltage is equal to or greater than 4% but less than 6%.
D: The rate of decrease in voltage is equal to or greater than 6%.

The obtained results are summarized in the following Table 4.

TABLE 4

| Sample No. | Metal complex dye | Initial conversion efficiency | Heat resistance durability | Relative amount of dye adsorbed | Desorption test | Dependence on iodine concentration | Note |
|---|---|---|---|---|---|---|---|
| 201 | D-1-1a | A | B | 1.20 | B | B | Present invention |
| 202 | D-1-2a | A | A | 1.30 | A | A | Present invention |
| 203 | D-1-4a | A | B | 1.25 | A | B | Present invention |
| 204 | D-1-5a | AA | A | 1.35 | A | A | Present invention |
| 205 | D-1-5b | AA | A | 1.30 | A | B | Present invention |
| 206 | D-1-5e | AA | A | 1.30 | A | B | Present invention |
| 207 | D-1-5f | AA | A | 1.30 | A | B | Present invention |
| 208 | D-1-5g | AA | A | 1.30 | A | B | Present invention |
| 209 | D-1-6a | AA | A | 1.30 | A | B | Present invention |
| 210 | D-1-11a | A | B | 1.20 | B | B | Present invention |
| 211 | D-1-12a | AA | A | 1.35 | A | A | Present invention |
| 212 | D-1-13a | A | B | 1.20 | B | B | Present invention |
| 213 | D-1-25a | A | B | 1.20 | B | B | Present invention |
| 214 | D-1-26a | A | A | 1.20 | B | B | Present invention |
| C11 | S-1 | D | D | 0.95 | D | D | Comparative example |
| C12 | S-2 | C | D | 0.95 | D | D | Comparative example |
| C13 | S-3 | C | D | 1.00 (Standard) | C | C | Comparative example |
| C14 | S-4 | D | D | 0.95 | C | C | Comparative example |
| C15 | S-5 | E | D | 1.00 | D | D | Comparative example |

The metal complex dyes S-1 to S-5 used in Sample Nos. C11 to C15 have the same definition as that of the metal complex dyes used in Example 1.

From Table 4, it is understood that, in the metal complex dye of the present invention, the photoelectric conversion efficiency and durability are excellent, and the dependence of voltage on the iodine concentration is small.

It is also understood that the metal complex dye of the present invention is adsorbed in a large amount onto the surface of the semiconductor particles and is hardly desorbed by a base.

1 CONDUCTIVE SUPPORT
2 PHOTORECEPTOR LAYER
21 DYE
22 SEMICONDUCTOR PARTICLES
3 CHARGE CARRIER LAYER
4 COUNTER ELECTRODE
5 LIGHT-RECEIVING ELECTRODE
6 CIRCUIT
10 PHOTOELECTRIC CONVERSION ELEMENT
100 SYSTEM USING DYE-SENSITIZED SOLAR CELL
M ELECTRIC MOTOR (ELECTRIC FAN)
20 DYE-SENSITIZED SOLAR CELL
40 PHOTOELECTRODE
41 TRANSPARENT ELECTRODE
42 SEMICONDUCTOR ELECTRODE
43 TRANSPARENT CONDUCTIVE FILM
44 SUBSTRATE
45 SEMICONDUCTOR LAYER
46 LIGHT SCATTERING LAYER
CE COUNTER ELECTRODE
E ELECTROLYTE
S SPACER

What is claimed is:

1. A photoelectric conversion element comprising:
a conductive support;
a photoreceptor layer containing an electrolyte;
a charge carrier layer containing an electrolyte; and
a counter electrode,
wherein the photoreceptor layer further contains semiconductor particles on which a metal complex dye represented by the following Formula (I) is carried, $$M^1(LA)(LD)(Z^1) \cdot CI \quad \text{Formula (I)}$$

in Formula (I), $M^1$ represents a metal atom; $Z^1$ represents a monodentate ligand; LA represents a tridentate ligand represented by the following Formula (AL-1); LD represents a bidentate ligand represented by the following Formula (DL-1); and CI represents a counterion necessary for neutralizing the charge,

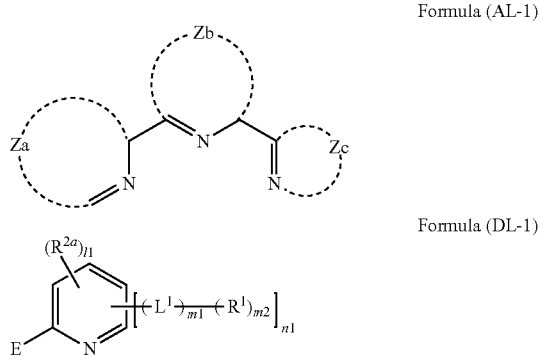

Formula (AL-1)

Formula (DL-1)

in Formula (AL-1), each of Za, Zb, and Zc represents a group of non-metal atoms necessary for forming a 5-membered ring or a 6-membered ring; here, at least one of the rings formed by Za, Zb, and Zc has an acidic group, in Formula (DL-1), m1 represents an integer of 0 to 3; m2 represents an integer of 1 to 4; n1 represents an integer of 1 to 4; $L^1$ represents an arylene group, an alkynylene group, or an alkynylenearylene group, and $R^1$ represents an amino group, an alkylamino group, an arylamino group, a heteroarylamino group, a halogen atom, an alkyl group, an alkynyl group, an alkoxy group, an aryloxy group, an alkylthio group, or an arylthio group; l1 represents an integer of 0 to 3; $R^{2a}$ represents a substituent different from $-[(L^1)m1-(R^1)m2]$, wherein the substituent represents a halogen atom, an alkyl group, an aryl group, a heterocyclic group, an alkoxy group, or an alkylthio group; and E represents a group represented by one of the following Formulae (E-1) to (E-6), (E-21), and (E-22),

Formula (E-1)

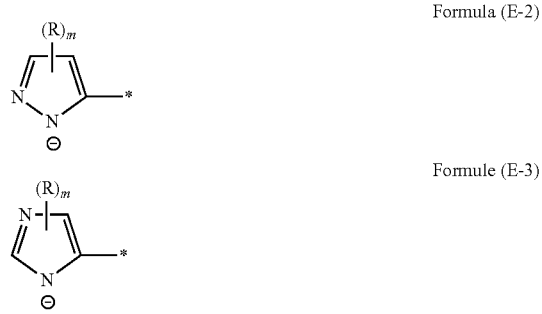

Formula (E-2)

Formule (E-3)

Formula (E-4)

Formula (E-5)

Formula (E-6)

in Formulae (E-1) to (E-6), R represents a halogen atom, an alkyl group, an alkoxy group, an aryl group, or a heteroaryl group; m represents an integer of equal to or greater than 0; herein, * represents a binding position in which the group is bonded to the 2-position of a pyridine ring,

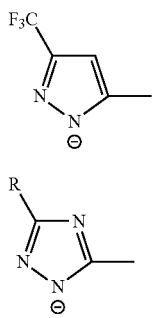

Formula (E-21)

Formula (E-22)

in Formula (E-22), R represents a hydrogen atom, an alkyl group, a phenyl group, or an aryloxy group.

2. The photoelectric conversion element according to claim 1,
wherein the bidentate ligand represented by Formula (DL-1) is represented by the following Formula (DL-2),

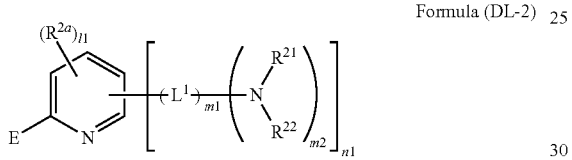

Formula (DL-2)

in Formula (DL-2), E, $L^1$, m1, m2, n1, $R^{2a}$, and 11 have the same definition as that of E, $L^1$, m1, m2, n1, $R^{2a}$, and 11 in Formula (DL-1); each of $R^{21}$ and $R^{22}$ independently represents a hydrogen atom, an alkyl group, an aryl group, or a heteroaryl group; and $R^{21}$ and $R^{22}$ may form a ring by being bonded to each other.

3. The photoelectric conversion element according to claim 1,
wherein $L^1$ represents an arylene group.

4. The photoelectric conversion element according to claim 1,
wherein the bidentate ligand represented by Formula (DL-1) is represented by the following Formula (DL-3),

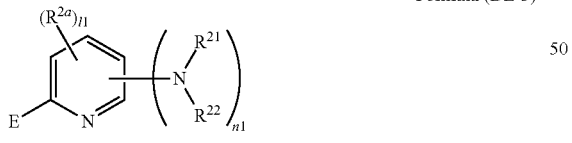

Formula (DL-3)

in Formula (DL-3), E, n1, $R^{2a}$, and 11 have the same definition as that of E, n1, $R^{2a}$, and 11 in Formula (DL-1); each of $R^{21}$ and $R^{22}$ independently represents a hydrogen atom, an alkyl group, an aryl group, or a heteroaryl group; and $R^{21}$ and $R^{22}$ may form a ring by being bonded to each other.

5. The photoelectric conversion element according to claim 1,
wherein $M^1$ represents Ru.

6. The photoelectric conversion element according to claim 1,
wherein LA is represented by the following Formula (AL-3),

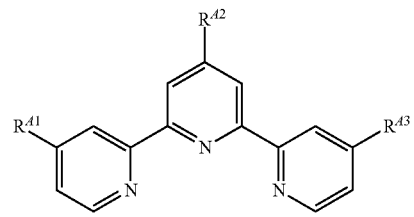

Formula (AL-3)

in Formula (AL-3), each of $R^{A1}$, $R^{A2}$, and $R^{A3}$ independently represents a hydrogen atom, an alkyl group, an aryl group, a heteroaryl group, or an acidic group; here, at least one of $R^{A1}$, $R^{A2}$, and $R^{A3}$ represents an acidic group.

7. The photoelectric conversion element according to claim 1,
wherein E is represented by Formula (E-2) or Formula (E-5).

8. The photoelectric conversion element according to claim 1,
wherein the metal complex dye is represented by the following Formula (II),

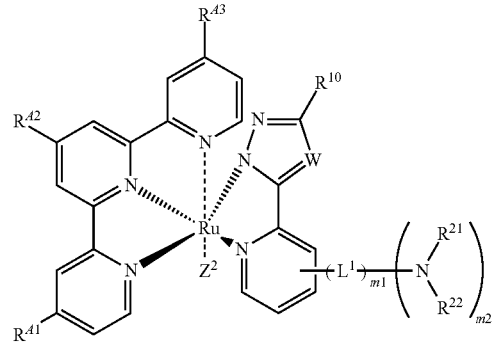

Formula (II)

in Formula (II), each of $R^{A1}$, $R^{A2}$, and $R^{A3}$ independently represents a hydrogen atom, an alkyl group, an aryl group, a heteroaryl group, or an acidic group; here, at least one of $R^{A1}$, $R^{A2}$, and $R^{A3}$ represents an acidic group,
each of $R^{21}$ and $R^{22}$ independently represents a hydrogen atom, an alkyl group, an aryl group, or a heteroaryl group; $R^{21}$ and $R^{22}$ may form a ring by being bonded to each other; $L^1$, m1, and m2 have the same definition as that of $L^1$, m1, and m2 in Formula (DL-1); W represents a nitrogen atom or CH; $R^{10}$ represents a hydrogen atom, an alkyl group, a perfluoroalkyl group, an aryl group, or a heteroaryl group; $Z^2$ represents an isothiocyanate group, an isoselenocyanate group, an isocyanate group, a halogen atom, or a cyano group.

9. The photoelectric conversion element according to claim 1,
wherein the metal complex dye is represented by the following Formula (III), Formula (III)

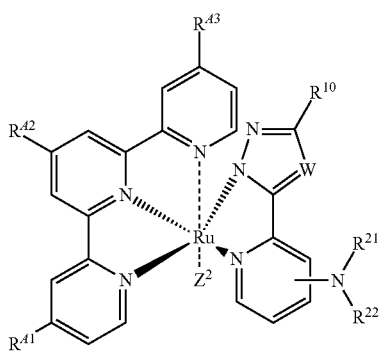

in Formula (III), each of $R^{A1}$, $R^{A2}$, and $R^{A3}$ independently represents a hydrogen atom, an alkyl group, an aryl group, a heteroaryl group, or an acidic group; W represents a nitrogen atom or CH; each of $R^{21}$ and $R^{22}$ independently represents a hydrogen atom, an alkyl group, an aryl group, or a heteroaryl group; $R^{21}$ and $R^{22}$ may form a ring by being bonded to each other; $R^{10}$ represents a hydrogen atom, an alkyl group, a perfluoroalkyl group, an aryl group, or a heteroaryl group; and $Z^2$ represents an isothiocyanate group, an isoselenocyanate group, an isocyanate group, a halogen atom, or a cyano group.

10. The photoelectric conversion element according to claim 2,
wherein each of $R^{21}$ and $R^{22}$ is selected from an alkyl group and an aryl group.

11. The photoelectric conversion element according to claim 2,
wherein $R^{21}$ represents an alkyl group or an aryl group, and $R^{22}$ represents an aryl group.

12. The photoelectric conversion element according to claim 1,
wherein Formula (DL-1) satisfies the following conditions in which in Formula (DL-1), l1 represents 0; $L^1$ represents an arylene group; $R^1$ represents a halogen atom, an alkyl group, an alkynyl group, an alkoxy group, an aryloxy group, an alkylthio group, or an arylthio group; and E represents a group represented by Formula (E-21) or (E-22).

13. The photoelectric conversion element according to claim 12,
wherein LD is represented by any of the following Formulae (DL-22) to (DL-24), Formula (DL-22)

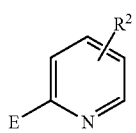

Formula (DL-23)

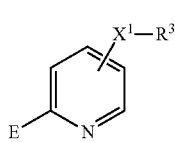

Formula (DL-24)

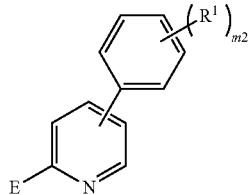

in Formulae (DL-22) to (DL-24), E, $R^1$, and m2 have the same definition as that of E, $R^1$, and m2 in Formula (DL-1); $X^1$ represents —C(Ra)(Rb)—, an ethynylene group, —S—, or —O—; each of Ra and Rb independently represents a hydrogen atom or an alkyl group; $R^2$ represents a halogen atom; when $X^1$ represents —C(Ra)(Rb)—, $R^3$ represents a hydrogen atom or an alkyl group; when $X^1$ represents an ethynylene group, $R^3$ represents a hydrogen atom, an alkyl group, an aryl group, or a heteroaryl group; when $X^1$ represents —S— or —O—, $R^3$ represents an alkyl group or an aryl group; and when m2 is equal to or greater than 2, a plurality of $R^1$s may be the same as or different from each other.

14. The photoelectric conversion element according to claim 12,
wherein LD is represented by any of the following Formulae (DL-23a) to (DL-23d) or represented by any of the following Formulae (DL-24a) to (DL-24c), Formula (DL-23a)

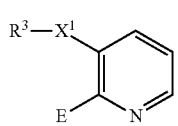

Formula (DL-23b)

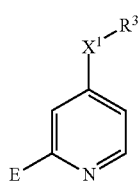

Formula (DL-23c)

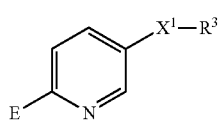

Formula (DL-23d)

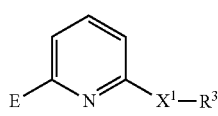

Formula (DL-24a)

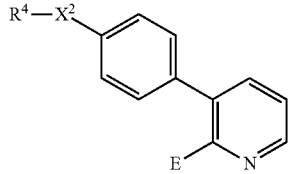

-continued

Formula (DL-24b)

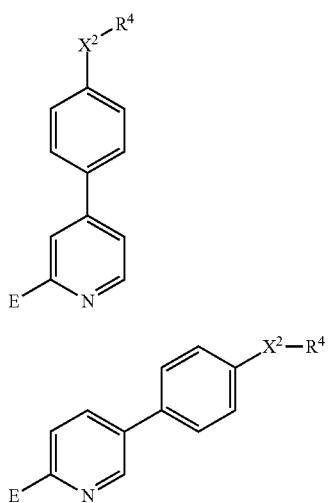

Formula (DL-24c)

Formula (XXII)

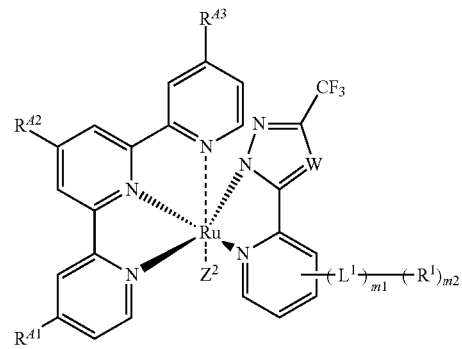

in Formulae (DL-23a) to (DL-23d) and (DL-24a) to (DL-24c), E has the same definition as that of E in Formula (DL-1); $X^1$ represents —C(Ra)(Rb)—, an ethynylene group, —S—, or —O—; each of Ra and Rb independently represents a hydrogen atom or an alkyl group; when $X^1$ represents —C(Ra)(Rb)—, $R^3$ represents a hydrogen atom or an alkyl group; when $X^1$ represents an ethynylene group, $R^3$ represents a hydrogen atom, an alkyl group, an aryl group, or a heteroaryl group; when $X^1$ represents —S— or —O—, $R^3$ represents an alkyl group or an aryl group; $X^2$ represents —C(Ra)(Rb)—, an ethynylene group, —S—, or —O—; when $X^2$ represents —C(Ra)(Rb)—, $R^4$ represents a hydrogen atom or an alkyl group; when $X^2$ represents an ethynylene group, $R^4$ represents a hydrogen atom, an alkyl group, an aryl group, or a heteroaryl group; and when $X^2$ represents —S— or —O—, $R^4$ represents an alkyl group or an aryl group.

15. The photoelectric conversion element according to claim 13,
wherein $X^1$ represents —C(Ra)(Rb)—, an ethynylene group, or —O—.

16. The photoelectric conversion element according to claim 14,
wherein $X^1$ or $X^2$ represents —C(Ra)(Rb)—, an ethynylene group, or —O—.

17. The photoelectric conversion element according to claim 13,
wherein $R^3$ represents an alkyl group having 5 or more carbon atoms.

18. The photoelectric conversion element according to claim 14,
wherein $R^3$ or $R^4$ represents an alkyl group having 5 or more carbon atoms.

19. The photoelectric conversion element according to claim 13,
wherein $R^3$ represents a linear alkyl group having 5 or more carbon atoms.

20. The photoelectric conversion element according to claim 14,
wherein $R^3$ or $R^4$ represents a linear alkyl group having 5 or more carbon atoms.

21. The photoelectric conversion element according to claim 12,
wherein the metal complex dye is represented by the following Formula (XXII), in Formula (XXII), each of $R^{A1}$, $R^{A2}$, and $R^{A3}$ independently represents a hydrogen atom, an alkyl group, an aryl group, a heteroaryl group, or an acidic group; here, at least one of $R^{A1}$, $R^{A2}$, and $R^{A3}$ represents an acidic group; $R^1$, $L^1$, m1, and m2 have the same definition as that of $R^1$, $L^1$, m1, and m2 in Formula (DL-1); W represents CH; and $Z^2$ represents an isothiocyanate group, an isoselenocyanate group, an isocyanate group, a halogen atom, or a cyano group.

22. The photoelectric conversion element according to claim 12,
wherein the metal complex dye is represented by the following Formula (XXIII), Formula (XXIII)

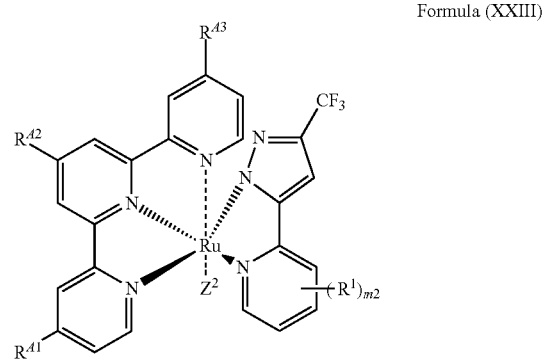

in Formula (XXIII), each of $R^{A1}$, $R^{A2}$, and $R^{A3}$ independently represents a hydrogen atom, an alkyl group, an aryl group, a heteroaryl group, or an acidic group; here, at least one of $R^{A1}$, $R^{A2}$, and $R^{A3}$ represents an acidic group; $R^1$ and m2 have the same definition as that of $R^1$ and m2 in Formula (DL-1); and $Z^2$ represents an isothiocyanate group, an isoselenocyanate group, an isocyanate group, a halogen atom, or a cyano group.

23. A dye-sensitized solar cell comprising the photoelectric conversion element according to claim 1.

24. A metal complex dye represented by the following Formula (I), $$M^1(LA)(LD)(Z^1) \cdot (CI) \qquad \text{Formula (I)}$$

in Formula (I), $M^1$ represents a metal atom; $Z^1$ represents a monodentate ligand; LA represents a tridentate ligand represented by the following Formula (AL-1); LD represents a bidentate ligand represented by the following Formula (DL-1); and CI represents a counterion necessary for neutralizing the charge, Formula (AL-1)

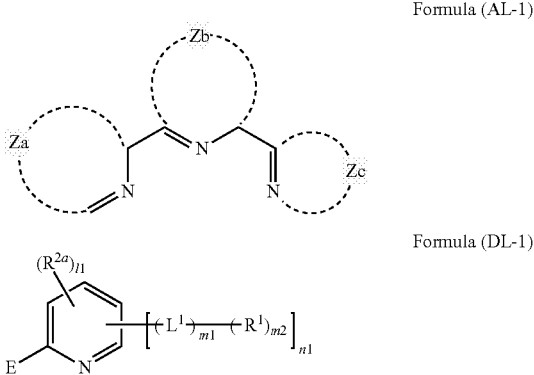

Formula (DL-1)

in Formula (AL-1), each of Za, Zb, and Zc represents a group of non-metal atoms necessary for forming a 5-membered ring or a 6-membered ring; here, at least one of the rings formed by Za, Zb, and Zc has an acidic group, in Formula (DL-1), m1 represents an integer of 0 to 3; m2 represents an integer of 1 to 4; n1 represents an integer of 1 to 4; $L^1$ represents an arylene group, an alkynylene group, or an alkynylenearylene group, and $R^1$ represents an amino group, an alkylamino group, an arylamino group, a heteroarylamino group, a halogen atom, an alkyl group, an alkynyl group, an alkoxy group, an aryloxy group, an alkylthio group, or an arylthio group; l1 represents an integer of 0 to 3; $R^{2a}$ represents a substituent different from -[($L^1$)m1-($R^1$)m2], wherein the substituent represents a halogen atom, an alkyl group, an aryl group, a heterocyclic group, an alkoxy group, or an alkylthio group; and E represents a group represented by one of the following Formulae (E-1) to (E-6), (E-21), and (E-22), Formula (E-1)

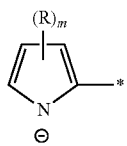

Formula (E-2)

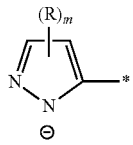

Formula (E-3)

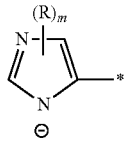

Formula (E-4)

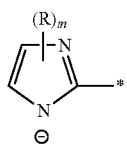

Formula (E-5)

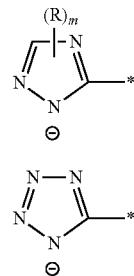

Formula (E-6)

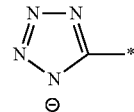

in Formulae (E-1) to (E-6), R represents a halogen atom, an alkyl group, an alkoxy group, an aryl group, or a heteroaryl group; m represents an integer of equal to or greater than 0; herein, * represents a binding position in which the group is bonded to the 2-position of a pyridine ring, Formula (E-21)

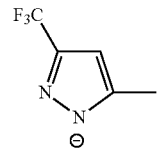

Formula (E-22)

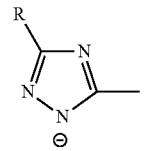

in Formula (E-22), R represents a hydrogen atom, an alkyl group, a phenyl group, or an aryloxy group.

25. The metal complex dye according to claim 24 that is represented by the following Formula (II), Formula (II)

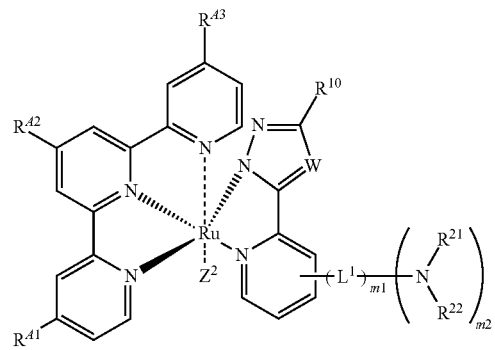

in Formula (II), each of $R^{41}$, $R^{42}$, and $R^{43}$ independently represents a hydrogen atom, an alkyl group, an aryl group, a heteroaryl group, or an acidic group; here, at least one of $R^{41}$, $R^{42}$ and $R^{43}$ represents an acidic group; each of $R^{21}$ and $R^{22}$ independently represents a hydrogen atom, an alkyl group, an aryl group, or a heteroaryl group; $R^{21}$ and $R^{22}$ may form a ring by being bonded to each other; $L^1$, m1, and m2 have the same definition as that of $L^1$, m1, and m2 in Formula (DL-1); W represents a nitrogen atom or CH; $R^{10}$ represents a hydrogen atom, an alkyl group, a perfluoroalkyl group, an aryl group, or a heteroaryl group; and $Z^2$ represents an isothiocyanate group, an isoselenocyanate group, an isocyanate group, a halogen atom, or a cyano group.

26. The metal complex dye according to claim 24 that is represented by the following Formula (III),

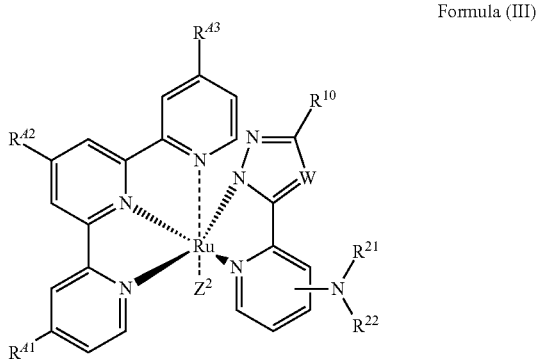

Formula (III)

in Formula (III), each of $R^{41}$, $R^{42}$, and $R^{43}$ independently represents a hydrogen atom, an alkyl group, an aryl group, a heteroaryl group, or an acidic group; here, at least one of $R^{41}$, $R^{42}$, and $R^{43}$ represents an acidic group; W represents a nitrogen atom or CH; each of $R^{21}$ and $R^{22}$ independently represents a hydrogen atom, an alkyl group, an aryl group, or a heteroaryl group; $R^{21}$ and $R^{22}$ may form a ring by being bonded to each other; $R^{10}$ represents a hydrogen atom, an alkyl group, a perfluoroalkyl group, an aryl group, or a heteroaryl group; and $Z^2$ represents an isothiocyanate group, an isoselenocyanate group, an isocyanate group, a halogen atom, or a cyano group.

27. The metal complex dye according to claim 24, wherein Formula (DL-1) satisfies the following condition in which in Formula (DL-1), l1 represents 0; $L^1$ represents an arylene group; $R^1$ represents a halogen atom, an alkyl group, an alkynyl group, an alkoxy group, an aryloxy group, an alkylthio group, or an arylthio group; and E represents a group represented by the following Formula (E-21) or (E-22),

Formula (E-21)

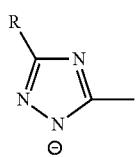

Formula (E-22)

in Formula (E-22), R represents a hydrogen atom, an alkyl group, a phenyl group, or an aryloxy group.

28. The photoelectric conversion element according to claim 1,
wherein each of Za, Zb, and Zc represents a group of non-metal atoms necessary for forming an imidazole ring, an oxazole ring, a thiazole ring, a triazole ring, a pyridine ring, a pyrimidine ring, a pyridazine ring, or a pyrazine ring.

29. The photoelectric conversion element according to claim 1,
wherein the acidic group represents a carboxy group, a phosphonyl group, a phosphoryl group, a sulfo group, or a boric acid group.

30. The photoelectric conversion element according to claim 1,
wherein CI represents a K ion, a Na ion, a Li ion, a cesium ion, an ammonium ion, or a pyridinium ion.

31. The photoelectric conversion element according to claim 1,
wherein $Z^1$ represents a monodentate ligand, which forms a coordinate bond through a group selected from the group consisting of an acyloxy group, an acylthio group, a thioacyloxy group, a thioacylthio group, an acylaminooxy group, a thiocarbamate group, a dithiocarbamate group, a thiocarbonate group, a dithiocarbonate group, a trithiocarbonate group, an acyl group, a thiocyanate group, an isothiocyanate group, a cyanate group, an isocyanate group, a selenate group, an isoselenate group, an isoselenocyanate group, a cyano group, an alkylthio group, an arylthio group, an alkoxy group, and an aryloxy group, and a monodentate ligand which is selected from the group consisting of a halogen atom, a phosphine ligand, carbonyl, dialkyl ketone, carbonamide, thiocarbonamide, and thiourea.

32. The metal complex dye according to claim 24,
wherein each of Za, Zb, and Zc represents a group of non-metal atoms necessary for forming an imidazole ring, an oxazole ring, a thiazole ring, a triazole ring, a pyridine ring, a pyrimidine ring, a pyridazine ring, or a pyrazine ring.

33. The metal complex dye according to claim 24,
wherein the acidic group represents a carboxy group, a phosphonyl group, a phosphoryl group, a sulfo group, or a boric acid group.

34. The metal complex dye according to claim 24,
wherein CI represents a K ion, a Na ion, a Li ion, a cesium ion, an ammonium ion, or a pyridinium ion.

35. The metal complex dye according to claim 24,
wherein $Z^1$ represents a monodentate ligand, which forms a coordinate bond through a group selected from the group consisting of an acyloxy group, an acylthio group, a thioacyloxy group, a thioacylthio group, an acylaminooxy group, a thiocarbamate group, a dithiocarbamate group, a thiocarbonate group, a dithiocarbonate group, a trithiocarbonate group, an acyl group, a thiocyanate group, an isothiocyanate group, a cyanate group, an isocyanate group, a selenate group, an isoselenate group, an isoselenocyanate group, a cyano group, an alkylthio group, an arylthio group, an alkoxy group, and an aryloxy group, and a monodentate ligand which is selected from the group consisting of a halogen atom, a phosphine ligand, carbonyl, dialkyl ketone, carbonamide, thiocarbonamide, and thiourea.

\* \* \* \* \*

UNITED STATES PATENT AND TRADEMARK OFFICE
CERTIFICATE OF CORRECTION

PATENT NO.         : 9,947,482 B2
APPLICATION NO.    : 14/879822
DATED              : April 17, 2018
INVENTOR(S)        : Kohsuke Watanabe et al.

Page 1 of 1

It is certified that error appears in the above-identified patent and that said Letters Patent is hereby corrected as shown below:

On the Title Page

In item (73) Assignee, please change as follows:
"FUJIFILM Corporation, Tokoyo (JP)"
To:
--FUJIFILM Corporation, Tokyo (JP)--

Signed and Sealed this
Tenth Day of July, 2018

Andrei Iancu
*Director of the United States Patent and Trademark Office*